(12) United States Patent
Hirata et al.

(10) Patent No.: US 8,172,072 B2
(45) Date of Patent: May 8, 2012

(54) CRUCIBLE FEEDER MECHANISM

(75) Inventors: Yasushi Hirata, Otsu (JP); Naoya Takei, Nara (JP); Yoshito Komada, Yamatokoriyama (JP)

(73) Assignee: Horiba, Ltd., Kyoto (JP)

( * ) Notice: Subject to any disclaimer, the term of this patent is extended or adjusted under 35 U.S.C. 154(b) by 329 days.

(21) Appl. No.: 12/485,792

(22) Filed: Jun. 16, 2009

(65) Prior Publication Data

US 2009/0321223 A1 Dec. 31, 2009

(30) Foreign Application Priority Data

| Jun. 26, 2008 | (JP) | 2008-167977 |
| Jun. 26, 2008 | (JP) | 2008-167978 |
| Jun. 26, 2008 | (JP) | 2008-167979 |
| Jun. 27, 2008 | (JP) | 2008-168233 |

(51) Int. Cl.
*B65G 47/12* (2006.01)

(52) U.S. Cl. ........ 198/562; 198/540

(58) Field of Classification Search ........ 198/562, 198/540, 481.1, 440, 532, 443; 221/222, 221/266, 277

See application file for complete search history.

(56) References Cited

U.S. PATENT DOCUMENTS

| 4,063,633 A * | 12/1977 | Hall | 198/455 |
| 4,138,941 A * | 2/1979 | McMillin et al. | 101/40 |
| 4,149,659 A * | 4/1979 | Reed et al. | 222/318 |
| 4,165,809 A * | 8/1979 | Klein et al. | 198/431 |
| 4,601,384 A * | 7/1986 | van Doren | 198/481.1 |
| 5,127,543 A * | 7/1992 | Meisels | 221/4 |
| 5,848,725 A * | 12/1998 | Saeki | 221/131 |
| 5,860,563 A * | 1/1999 | Guerra et al. | 221/172 |
| 6,112,942 A * | 9/2000 | Deacon | 221/266 |
| 6,390,328 B1 * | 5/2002 | Obermeier et al. | 221/203 |
| 6,488,174 B1 * | 12/2002 | Cho | 221/7 |
| 6,651,802 B2 * | 11/2003 | Hurst | 198/443 |
| 6,726,058 B2 * | 4/2004 | Giraud | 221/267 |

FOREIGN PATENT DOCUMENTS

| JP | 02-257062 | 10/1990 |
| JP | 2006-504070 | 2/2006 |
| WO | WO 03/079028 | 9/2003 |

* cited by examiner

*Primary Examiner* — Douglas Hess

(57) ABSTRACT

This invention is intended to make a crucible feeder mechanism simple in configuration, to realize low cost and to increase the number of accommodated crucibles while making the crucible feeder mechanism small in size. In the crucible feeder mechanism, the crucibles are mounted on an inclined mount surface 311 in parallel and a tapered guide surface guides 312b the crucibles sliding down the mount surface 311 to a crucible moving mechanism 313 provided at an outlet port of a guide member. This crucible moving mechanism includes an accommodation concave portion 3131X accommodating one of the crucibles and provided on a circumferential surface portion 3131*a* of the crucible moving mechanism. The crucible moving mechanism rotates and moves between an accommodation position at which the accommodation concave portion receives the sliding-down crucible and a feed position at which the accommodation concave portion communicates with a crucible feed port 314 and drops the sliding-down crucible.

8 Claims, 29 Drawing Sheets

CRUCIBLE FEEDER MECHANISM

BACKGROUND OF THE INVENTION

1. Field of the Invention

The present invention relates to an elemental analysis device analyzing an element such as carbon (C), nitrogen (N), hydrogen (H), sulfur (S) or oxygen (O) contained in a measurement sample such as steel, nonferrous metal or ceramics. More specifically, the present invention relates to a crucible feeder mechanism feeding crucibles.

2. Description of the Background Art

As disclosed in, for example, Japanese Patent No. 2949501, an elementary analysis device of this type has a measurement sample accommodated in a crucible sandwiched between an upper electrode and a lower electrode, heats the measurement sample in the crucible by applying voltage, analyzes gas generated by heating the sample and thereby analyzes elements of the measurement sample. Furthermore, this elementary analysis device includes a crucible feeder mechanism feeding crucibles and is configured to transport one of the crucibles fed by the crucible feeder mechanism onto the lower electrode.

As disclosed in Japanese Translation of PCT No. 2006-504070, the crucible feeder mechanism conventionally accommodates a plurality of columns of crucibles in a cylindrical accommodation space and is configured to open an opening/closing port provided in a lower portion of the accommodation space and to drop one of the columns of crucibles, thereby feeding the crucibles.

With this configuration, it is necessary to provide a holding mechanism such as an actuator for holding the crucibles other than the dropped columns of crucibles when the opening/closing port is opened to drop the crucibles. Furthermore, to drop the crucibles in another column of crucibles after feeding one column, it is also necessary to provide a rotating mechanism to rotate the accommodation space and to move another column of crucibles to an upper portion of the opening/closing port. It is also necessary to provide a sensor to detect that each column of interest is not present. If these mechanisms and the like are provided, then the crucible feeder mechanism is complicated structurally and manufacturing cost increases. Moreover, a space such as a space for installing the mechanisms occupied by components other than the crucibles becomes wide. As a result, the crucible feeder mechanism is made large in size but the number of accommodated crucibles is small.

SUMMARY OF THE INVENTION

The present invention has been made to solve all the conventional problems at a stroke. It is an initial and main object of the present invention to make a crucible feeder mechanism simple in configuration, to realize low cost and to increase the number of accommodated crucibles while making the crucible feeder mechanism small in size.

According to one aspect of the present invention, there is provided a crucible feeder mechanism used in an elementary analysis device heating a sample accommodated in a crucible, thereby extracting and analyzing an element contained in the sample as a gas component, including: an inclined mount surface on which a plurality of crucibles is mounted in parallel; a guide member having an outlet port formed downward of an inclination direction of the mount surface, and guiding one of the crucibles sliding down the mount surface by an empty weight of the crucible toward the outlet port; and a crucible moving mechanism provided to interpose between the outlet port of the guide member and a feed port for feeding the crucibles, and moving one of the crucibles sliding down to the outlet port to the feed port, wherein the crucible moving mechanism includes a crucible moving body provided at the outlet port of the guide member, an accommodation concave portion accommodating therein one of the crucibles sliding down the mount surface being formed on a circumferential surface portion of the crucible moving body; and a driving part driving the crucible moving body to move between an accommodation position at which the accommodation concave portion receives and accommodates therein one of the crucibles sliding down and a feed position at which the crucible accommodated in the accommodation concave portion is dropped to the feed port.

If the crucible feeder mechanism is constituted as stated above, the crucibles are mounted in parallel and the number of accommodated crucibles can be, therefore, increased. Furthermore, one of the crucibles sliding down the mount surface by its empty weight is guided to the outlet port by the guide member and the guided crucible slides down in the accommodation concave portion as it is and transported to the feed port. It is, therefore, possible to simplify a configuration of the crucible feeder mechanism and reduce manufacturing cost. Furthermore, by simplifying the configuration of the crucible feeder mechanism or by mounting the crucibles in parallel, the crucible feeder mechanism can be made small in size.

To make the crucible feeder mechanism simple in configuration and small in size by simplifying the configuration of the crucible moving mechanism, it is preferable that the driving part drives the crucible moving body to rotate and causes the circumferential surface portion of the crucible moving body to close the outlet port in a state in which the crucible moving body rotates from the accommodation position. This can dispense with a mechanism for interrupting the crucible sliding down from the outlet port of the guide member.

Furthermore, to prevent the crucible from clogging near the outlet port of the guide member and from not sliding down into the accommodation concave portion of the crucible moving body by a simple configuration, it is preferable that the crucible moving body includes a protrusion in contact with one of the crucibles present near the outlet port of the guide member while the crucible moving body is moving between the accommodation position and the feed position.

To appropriately prevent the crucible mounted on the mount surface from overturning and interrupting feeding of crucibles, it is preferable that the crucible feeder mechanism includes a safety structure against overturning for preventing the crucibles mounted on the mount surface from overturning, that the safety structure against overturning is formed by an opposing surface provided to oppose the mount surface, and that a distance between the mount surface and the opposing surface is smaller than a length of a longest diagonal of the crucible mounted on the mount surface.

In this way, according to the present invention, it is possible to make a crucible feeder mechanism simple in configuration, to realize low cost and to increase the number of accommodated crucibles while making the crucible feeder mechanism small in size.

DESCRIPTION OF THE PREFERRED EMBODIMENTS

First Embodiment

Figure 1:
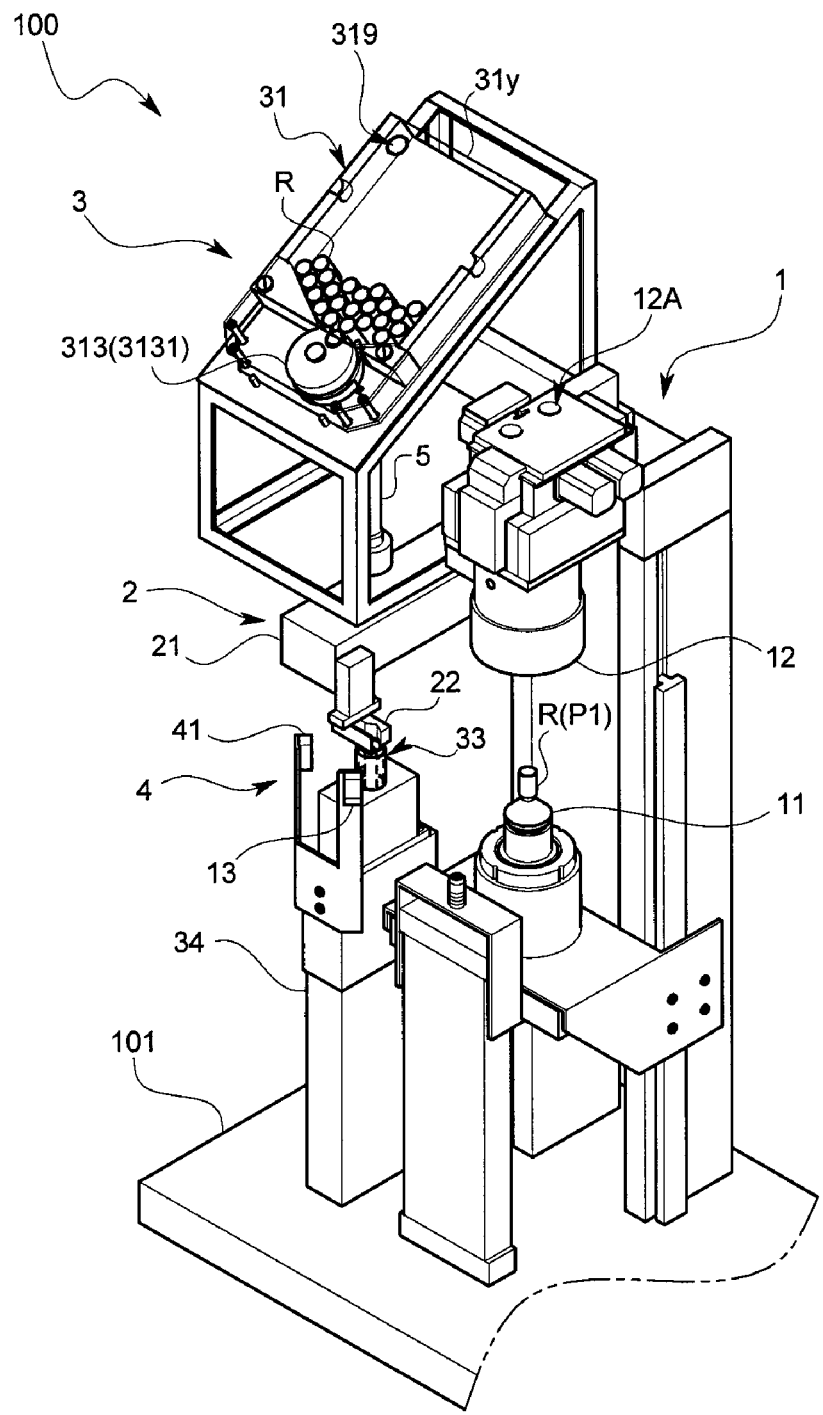
FIG. 1 is a typical configuration diagram of an elementary analysis device according to a first embodiment of the present invention.
Figure 2:
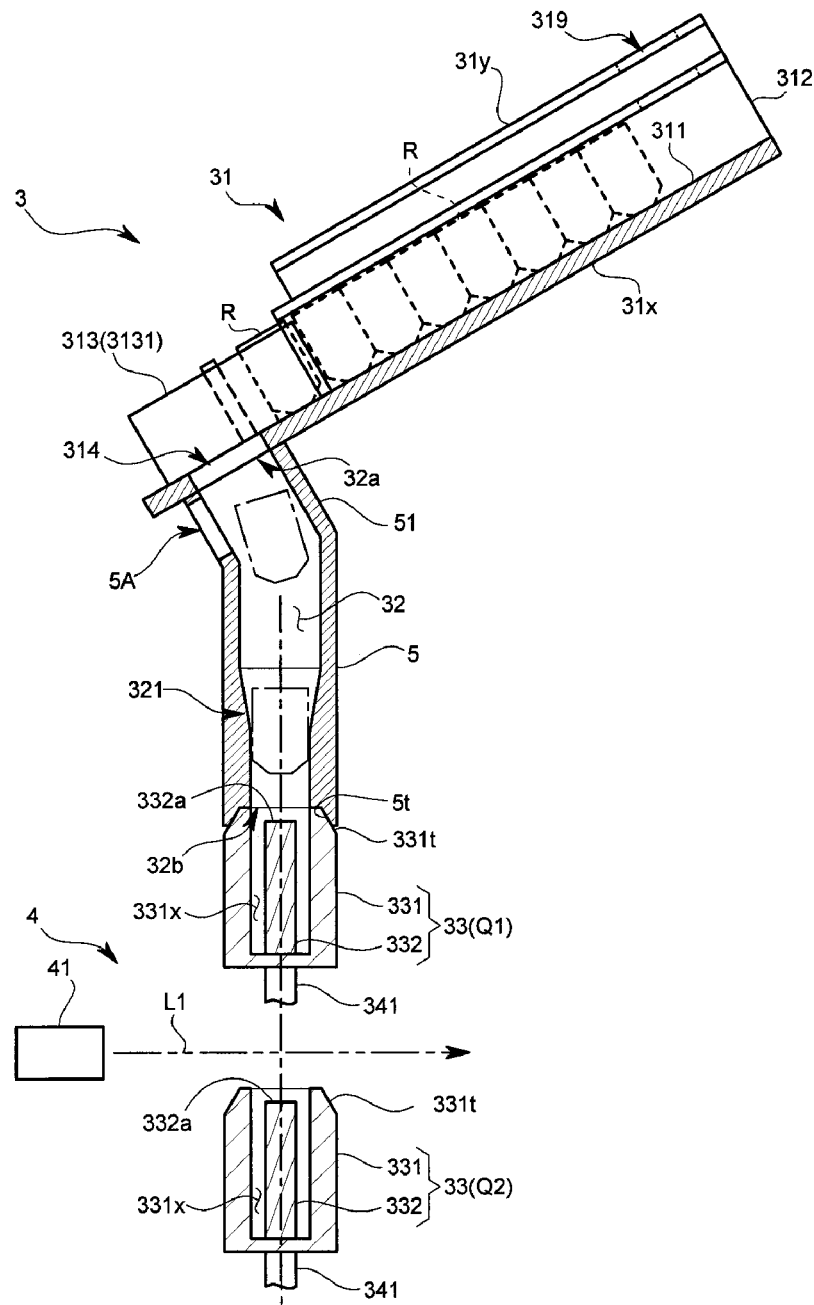
FIG. 2 is a longitudinal sectional view showing a configuration of a crucible feeder mechanism according to the first embodiment.
Figure 3:
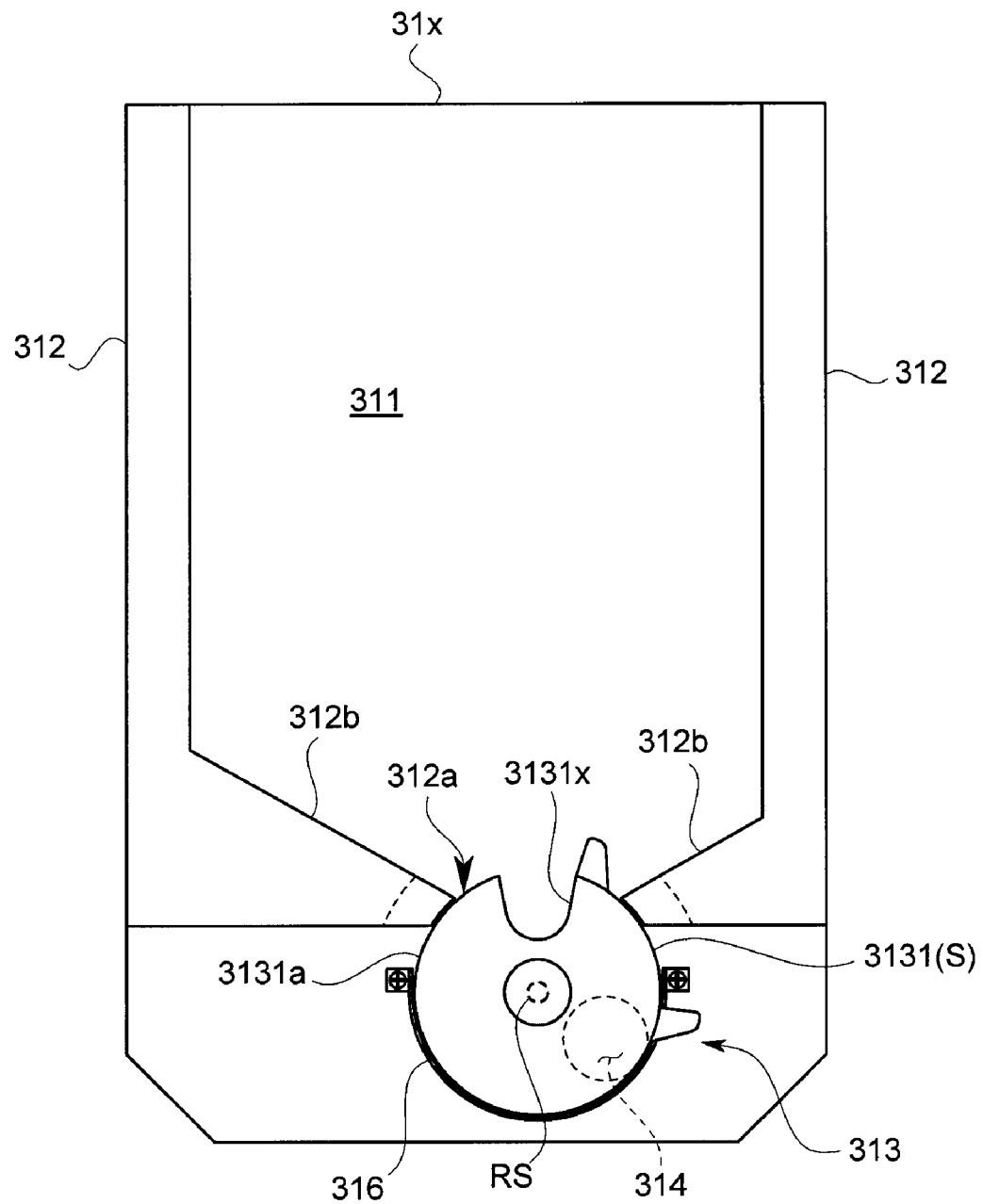
FIG. 3 is a plan view of a crucible accommodation part according to the first embodiment.
Figure 4:
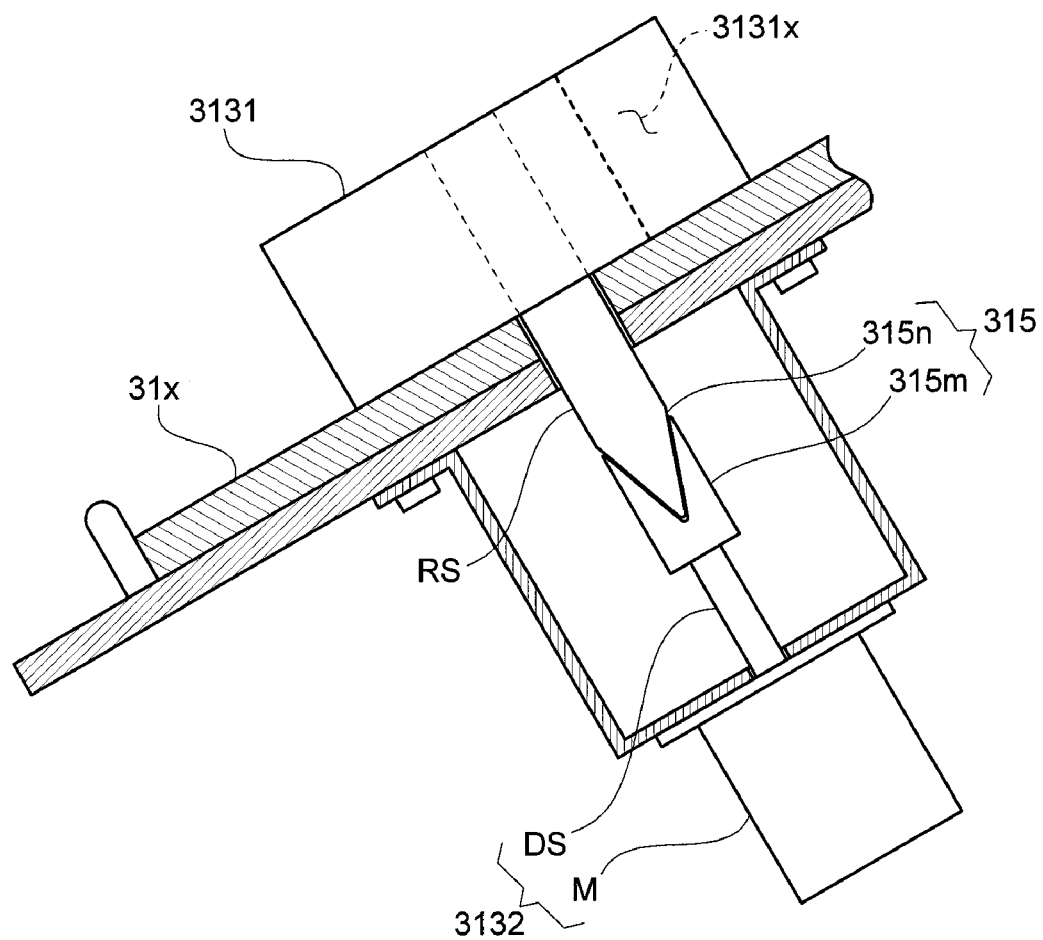
FIG. 4 is a plan view of a crucible moving body according to the first embodiment.
Figure 5:
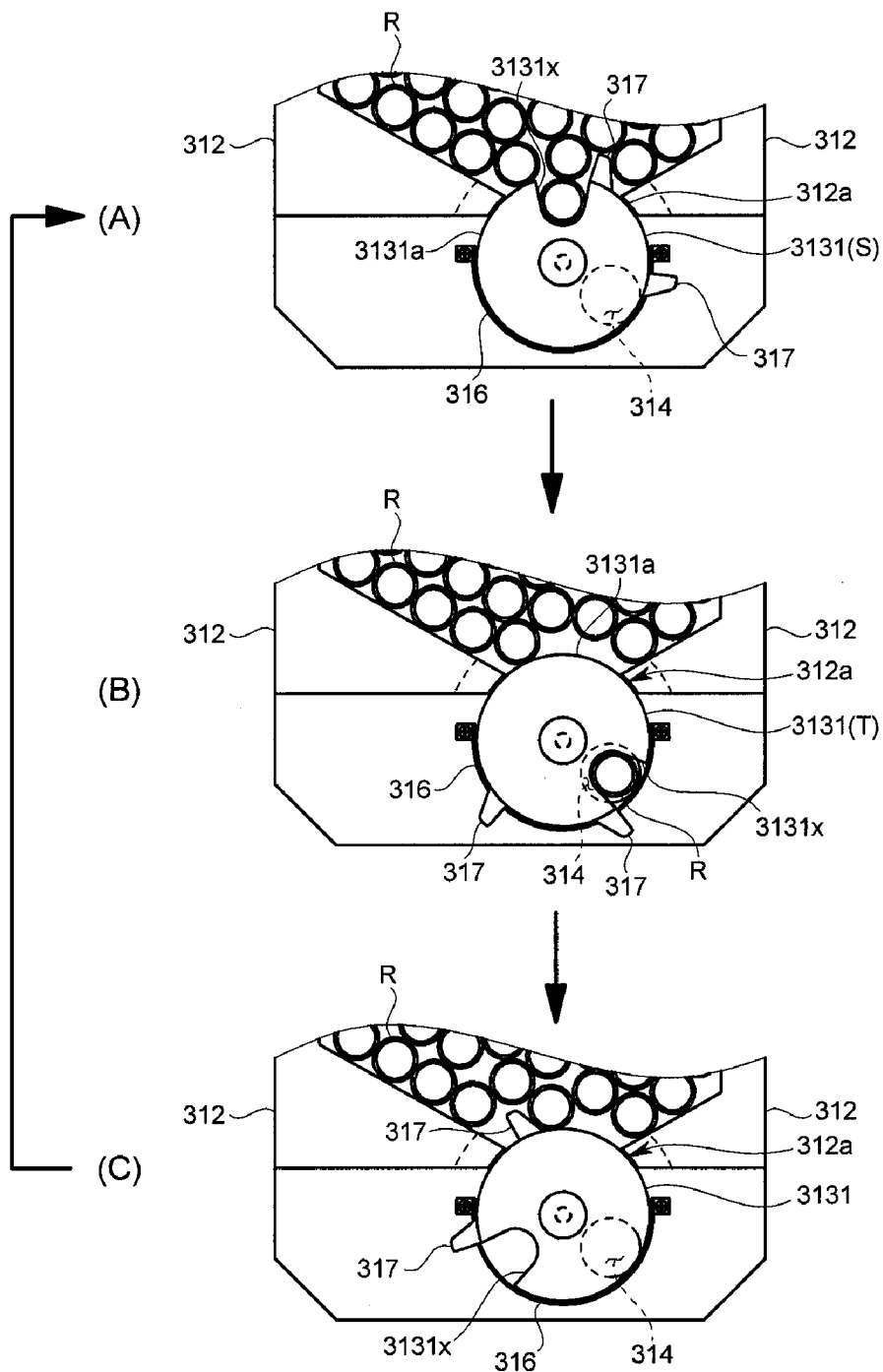
FIGS. 5A to 5C are schematic diagrams showing operation performed by the crucible moving body according to the first embodiment.
Figure 6:
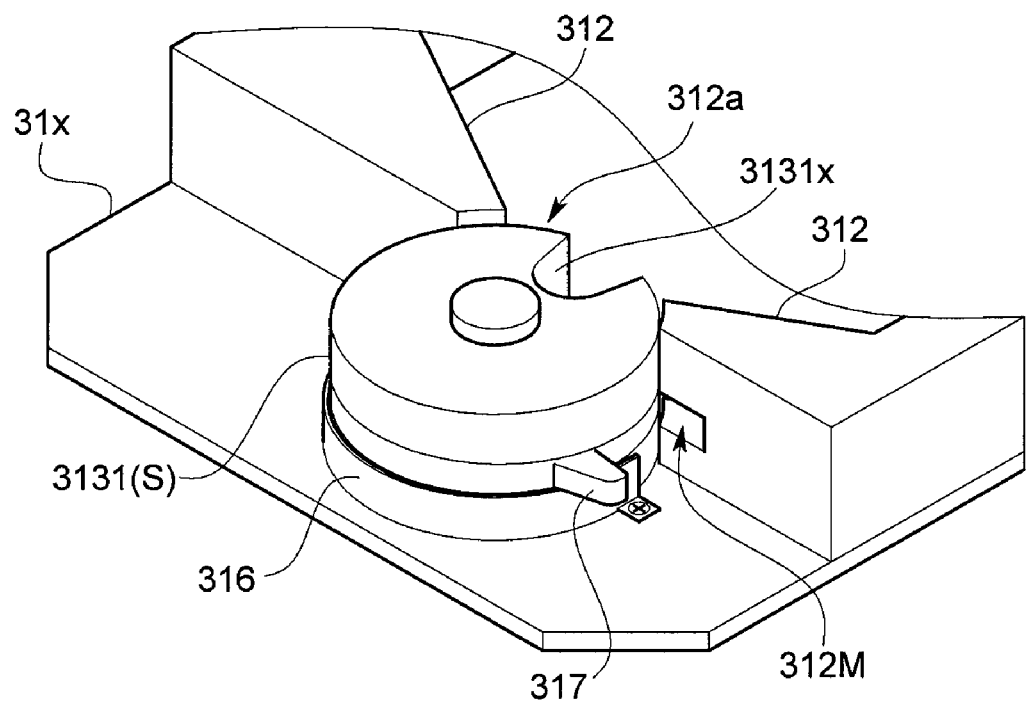
FIG. 6 is a partial perspective view mainly showing neighborhoods of the crucible moving body and an outlet port of a guide member according to the first embodiment.
Figure 7:
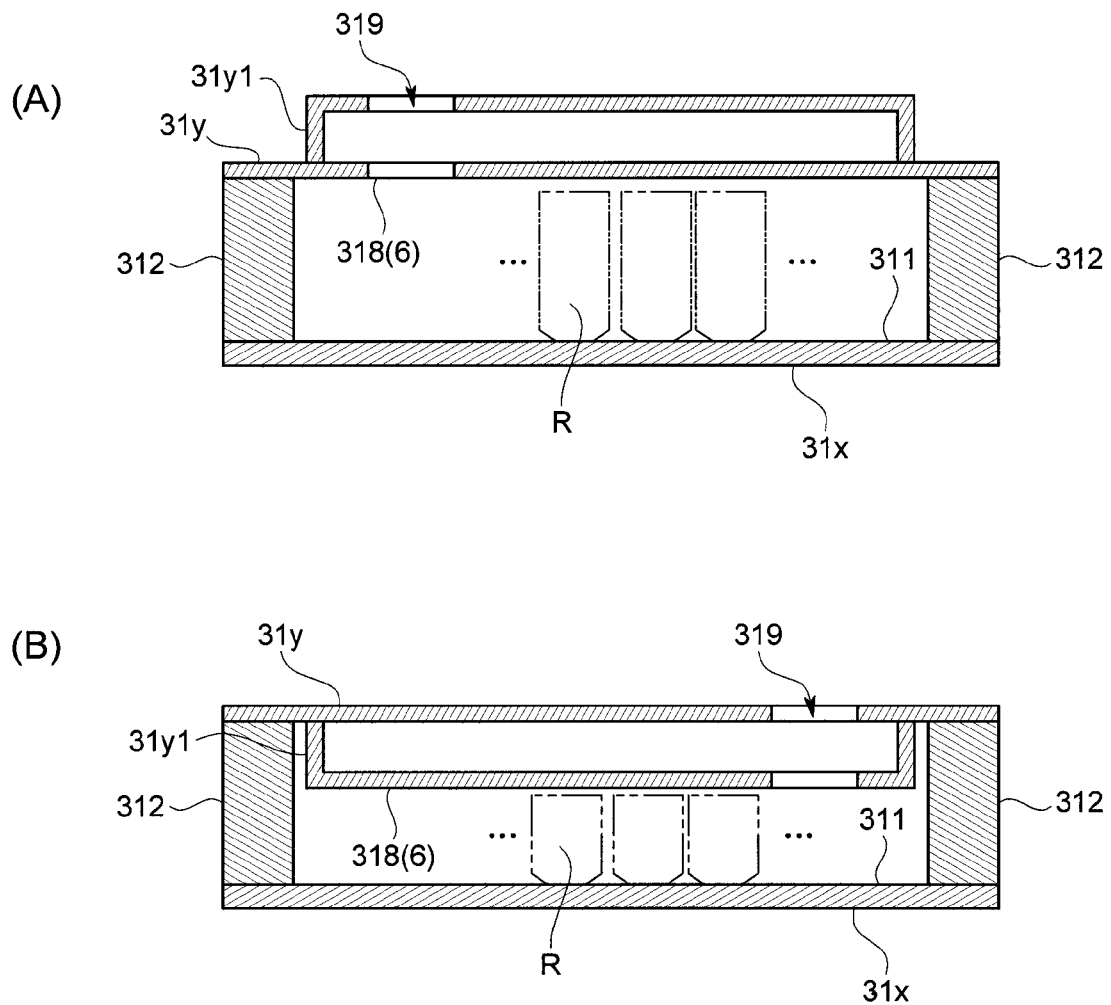
FIGS. 7A and 7B are cross-sectional views showing a safety structure against overturning according to the first embodiment.

A first embodiment of the present invention will be described referring to the drawings. FIG. 1 is a schematic configuration diagram of an elementary analysis device 100 according to the first embodiment, FIG. 2 is a typical cross-sectional view showing a configuration of a crucible feeder mechanism 3 and FIG. 3 is a front view of a crucible accommodation part 31. FIG. 4 is a cross-sectional view typically showing a crucible moving mechanism 313, and FIGS. 5A to 5C are schematic diagrams showing operation performed by a crucible moving body 3131. FIG. 6 is a partial perspective view mainly showing neighborhoods of the crucible moving body 3131 and an outlet port 312a of a guide member 312, and FIGS. 7A and 7B are cross-sectional views showing a safety structure against overturning 312.

<Device Configuration>

The elementary analysis device 100 according to the present embodiment heats a metal sample (hereinafter, also simply "sample") accommodated in each of crucibles R and analyzes components of gas generated at the time of heating, thereby measuring an element contained in the sample. The elementary analysis device 100 includes an analysis device main body 1, a crucible transport mechanism 2 transporting the crucibles R to the analysis device main body 1 and a crucible feeder mechanism 3 feeding the crucibles R transported by the crucible transport mechanism 2. The analysis device main body 1, the crucible transport mechanism 2 and the crucible feeder mechanism 3 will be described below, respectively.

<<Analysis Device Main Body 1>>

The analysis device main body 1 will be described. As shown in FIG. 1, an upper electrode 12 and a lower electrode 11 are provided on a front surface of this analysis device main body 1 to be vertically distanced from each other and the analysis device main body 1 is configured to be able to mount one of the crucibles R in which the sample is accommodated on the lower electrode 11. A position of the crucible R mounted on the lower electrode 11 shown in FIG. 1 is a heating position P1. In FIG. 1, reference symbol 13 denotes a detection sensor (such as a photoelectric sensor) detecting whether or not a crucible R is present on the lower electrode 11. Each crucible R is made of graphite, and has an open upper portion of a cylindrical shape and a tapered lower end portion. The crucible R may have an annular concave groove on an outer circumference of the lower end portion instead of having the tapered lower end portion.

During an analysis, the lower electrode 11 slides upward with respect to the crucible R located at the heating position P1 to sandwich the crucible R between the lower electrode 11 and the upper electrode 12. In this state, when a sample is input into the crucible R from a sample input port 12A provided above the upper electrode 12, then current is applied between the electrodes 11 and 12, heat is generated from the crucible R, and the sample within the crucible R is heated. Gas generated from the heated sample is supplied to an analysis part, not shown, components of the gas are measured and elements originally contained in the sample are analyzed as a result of measurement of the gas components.

To measure an amount of oxygen contained in the sample, for example, CO (carbon monoxide) that is a reaction product is generated by heating the sample, CO is measured using, for example, a non-dispersive infrared analyzer constituting the analysis part and the amount of oxygen present in the sample is measured and calculated based on a measured CO value. Furthermore, such components as hydrogen and nitrogen can be measured by setting the reaction product and the analysis part according to the reaction product. After the analysis, the crucible transport mechanism 2 disposes of the used crucible R as well as the sample.

<<Crucible Transport Mechanism 2>>

As shown in FIG. 1, the crucible transport mechanism 2 transports the crucible R installed on a crucible installation part 33, to be described later, to the heating position P1 in the analysis device main body 1. The crucible transport mechanism 2 includes an arm part 21 movable forward and backward with respect to the heating position P1 (lower electrode 11), a drive mechanism (not shown) driving the arm part 21 and a pair of grip clutches 22 attached to a tip end of the arm part 21. The crucible transport mechanism 2 is controlled by an instruction from a controller (not shown) provided separately.

A proximal end portion of the arm part 21 is connected to a rotary shaft of the drive mechanism provided on a base 101. This drive mechanism drives the arm part 21 to rotate and move forward and backward between the heating position P1 and a retreat position away from the heating position P1. The retreat position is located outward of the crucible installation part 33 with respect to the heating position P1. Further, at least one of the grip clutches 22 is, for example, generally doglegged. Each of the grip clutches 22 is held to be able to be driven to slide on the proximal end portion of the arm part 21. The crucible transport mechanism 2 is configured to be able to sandwich and grip a side circumferential surface of the crucible R between central portions of the grip clutches 22 by driving the clutches 22 to slide to narrow a distance between the clutches 22 in response to an instruction from the controller.

Operation performed by the crucible transport mechanism 2 will be described. During transport of one of the crucibles R, the arm part 2 rotates and moves from the retreat position and arrives at the crucible installation part 33. The grip clutches 21 grip the crucible R installed on the crucible installation part 33. Thereafter, the arm part 22 rotates and moves again to the heating position P1 and mounts the crucible R at the heating position P1 (onto the lower electrode 11). After mounting, the arm part 2 returns to the retreat position. Moreover, after an analysis, the arm part 21 moves from the retreat position to the heating position P1, the grip clutches 21 grip the crucible R present on the lower electrode 11 and the crucible transport mechanism 2 transports the crucible R to a disposal container, not shown, and disposes of the crucible R.

<<Crucible Feeder Mechanism 3>>

The crucible feeder mechanism 3 automatically feeds the crucible R transported by the crucible transport mechanism 2. Particularly shown in FIG. 2, the crucible feeder mechanism 3 includes the crucible accommodation part 31 in which a plurality of crucibles R can be accommodated, a guide passage 32 dropping each crucible R from the crucible accommodation part 31 by an empty weight of the crucible R and the crucible installation part 33 provided at an outlet port 32b of the guide passage 32 and receiving the dropped crucible R.

As shown in FIGS. 2 and 3, the crucible accommodation part 31 includes an inclined mount surface 311 on which a plurality of crucibles R is mounted in parallel, a guide member 312 having an outlet port 312a formed downward of an inclination direction of the mount surface 311 and guiding each crucible R sliding down the mount surface 311 by the empty weight of the crucible R, and a crucible moving mechanism 313 provided to interpose between the outlet port 312a of the guide member 312 and a feed port 314 feeding the crucible R to the guide passage 32 and moving the crucible R sliding down to the outlet port 312a to the feed port 314. The feed port 314 is provided downward of the mount surface 311 of a flat plate 31x.

As shown in FIG. 2, the mount surface 311 is inclined at such an angle that each crucible R slides down by its empty weight without falling down and formed on an upper surface of the flat plate 31x provided to be inclined with respect to a horizontal direction. This inclination angle is an angle at which the crucible R moved to the feed port 314 falls by its empty weight or, to be specific, about 30 degrees.

As shown in FIG. 3, the guide member 312 is provided to cover up surroundings of the mount surface 311 on the upper surface of the flat plate 31x. Specifically, the guide member 312 is provided to be built on left and right sides of the mount surface 311 and downward of the inclined surface so as to open an upper portion of the mount surface 311 and to open upward of the inclination direction. Furthermore, the outlet port 312a for sliding down each crucible R and introducing the crucible R to outside is formed downward of the inclination direction. The guide member 312 according to the present embodiment includes tapered guide surfaces 312b so that a width between the left and right opposing surfaces is narrower toward the outlet port 312a to introduce the crucible R that slides down to the outlet port 312. By opening the mount surface 311 upward of the inclination direction, it is possible to easily feed the crucibles R.

As shown in FIGS. 3 and 4, the crucible moving mechanism 313 includes the crucible moving body 3131 in which an accommodation concave portion 3131x accommodating therein the crucible R sliding down the mount surface 311 is formed on a circumferential surface portion 3131a and a driving part 3132 driving the crucible moving body 3131 to rotate and move between an accommodation position S at which the accommodation concave portion 3131x receives and accommodates therein the sliding-down crucible R and a feed position T at which the accommodation concave portion 3131x communicates with the feed port 314 and the crucible R present in the accommodation concave portion 3131x is dropped to the feed port 314 by the empty weight of the crucible R.

The crucible moving body 3131 is provided near the outlet port 312a of the guide member 312 on the upper surface of the flat plate 31x. The crucible moving body 3131 is generally rotating body-shaped and, in the present embodiment, generally cylindrical. Furthermore, the crucible moving body 3131 has a rotary shaft RS as a central axis and is configured to be rotatable uniaxially by this rotary shaft RS.

The accommodation concave portion 3131x is formed from an upper surface that is one end surface of the circumferential surface portion 3131a of the crucible moving body 3131 to a lower surface that is the other end surface of the circumferential surface portion 3131a. This accommodation concave portion 3131x has a size enough to accommodate therein one crucible R. In a state in which the accommodation concave portion 3131x accommodates therein one crucible R, the crucible R is located within a virtual circumcircle of the crucible moving body 3131.

The driving part 3132 is provided on a rear surface of the flat plate 31x and fixed to the device main body 1. As shown in FIG. 4, the driving part 3132 drives the crucible moving body 3131 to rotate about the rotary shaft RS and includes a motor M and a driving shaft DS transmitting rotation of the motor M to the rotary shaft RS provided in the crucible moving body 3131. It is to be noted that the rotary shaft RS of the crucible moving body 3131 penetrates a through-hole provided in the flat plate 31x, extends toward a rear surface of the flat plate 31x and is connected to the driving shaft DS of the driving part 3132.

In the present embodiment, the driving part 3132, the crucible moving body 3131 and the flat plate 31x (mount surface 311 and guide member 312) are made separable from one another. That is, a separation and connection mechanism 315 is provided between the rotary shaft RS connected to the crucible moving body 3131 and the driving shaft DS of the driving part 3132. This separation and connection mechanism 315 is configured to include a concave portion 315m provided on one of the rotary shaft RS and the driving shaft DS and a convex portion 315n provided on the other shaft. The concave portion 315m and the convex portion 315n are configured to be detachable axially and engaged with each other so as not to be rotatable relatively to each other when being connected to each other. This separation and connection mechanism 315 can facilitate detaching the crucible moving body 3131 and the flat plate 31x from the device main body 1 and cleaning, for example, the crucible moving body 3131 and the flat plate 31x.

As shown in FIGS. 5A to 5C, the driving part 3132 drives the crucible moving body 3131 to rotate in one direction so that the crucible moving body 3131 rotates and moves between the accommodation position S (FIG. 5A) at which the accommodation concave portion 3131x receives and accommodates therein the sliding-down crucible R and the feed position T (FIG. 5B) at which the accommodation concave portion 3131x communicates with the feed port 314 and drops the crucible R accommodated in the accommodation concave portion 3131x to the feed port 314 by the empty weight of the crucible R.

At the accommodation position S, the accommodation concave portion 3131x is located within the outlet port 312a of the guide member 312 and oriented upward of the inclination direction. When the accommodation concave portion 3131x is rotated about the rotary shaft RS, the feed port 314 is provided on a moving circle by as much as which the accommodation concave portion 3131x is rotated about the rotary shaft RS.

The circumferential surface portion 3131a of the crucible moving body 3131 closes the outlet port 312a of the guide member 312 until the crucible moving body 3131 reaches the accommodation position S again when the driving part 3132 drives the crucible moving body 3131 to rotate and move from the accommodation position S (see FIGS. 5A to 5C). The crucible R sliding downward from the outlet port 312a can be thereby interrupted. This can also make a mechanism closing the outlet port 312a of the guide member 312 unnecessary to provide separately.

Moreover, as shown in FIGS. 3, 5A to 5C and 6, the crucible moving body 3131 includes a protrusion 317 in contact with the crucible R present near the outlet port 312a of the guide member 312 halfway along moving between the accommodation position S and the feed position T. This protrusion 317 is provided on the circumferential surface portion 3131a of the crucible moving body 3131 or, to be specific, provided near a rotational direction of the accommodation concave portion 3131x. The protrusion 317 contacts with the crucible R near the outlet port 312a of the guide member 312 before the accommodation concave portion 3131x reaches the outlet port 312a halfway along moving of the accommodation concave portion 3131x from the feed position T to the accommodation position S, thereby making it possible to clear up clogging of the crucibles R (FIG. 5C). As shown in FIG. 6, a notch groove 312M through which the protrusion 317 passes is provided in the outlet port 312a of the guide member 312 so as not to interrupt moving of the protrusion 317.

Furthermore, the feed port 314 according to the present embodiment is provided downward of the rotary shaft RS in the inclination direction. Due to this, if the crucible moving body 3131 is rotated while holding one of the crucibles R in the accommodation concave portion 3131x, the crucible R possibly drops from the accommodation concave portion 3131x to outward of the circumferential surface portion 3131a before the crucible R moves to the feed port 314. To prevent this dropping, a safety wall against dropping 316 is provided on a circumference of the crucible moving body 3131 as shown in FIGS. 3, 5A, 5B and 6. This safety wall against dropping 316 is provided along at least a lower side surface of the crucible moving body 3131 in the inclination direction and covers up a circumferential surface portion-side opening of the accommodation concave portion 3131 when the accommodation concave portion 3131x is directed downward of the inclination direction.

Furthermore, as shown in FIGS. 7A and 7B, the crucible accommodation part 31 includes a safety structure against overturning 6 for preventing the crucibles R mounted on the mount surface 311 from overturning. This safety structure against overturning 6 is formed by an opposing surface 318 provided to oppose the mount surface 311 and provided so that a distance between the mount surface 311 and the opposing surface 318 is smaller than a length of a longest diagonal of the crucible R. Specifically, the opposing surface 318 is formed by a surface of a cover body 31y provided detachably on the guide member 312 which surface directs toward the mount surface 311. This cover body 31y can be attached to either a front or a rear surface of the guide member 312. The distance between the mount surface 311 and the opposing surface 318 is made to differ between an instance of providing a sheet-metal portion 31y1 on one of the front surface and the rear surface of the guide member 312 and attaching a rear surface of the sheet-metal portion 31y1 to the guide member 312 (FIG. 7A) and an instance of attaching a front surface of the sheet-metal portion 31y1 to the guide member 312 (FIG. 7B). The safety structure against overturning 6 can thereby fulfill its function to correspond to the crucibles R differing in size. Specifically, the safety structure against overturning 6 can fulfill the function to correspond to the crucibles R differing in size such as graphite crucibles each having the tapered lower end portion as stated above or graphite crucibles each having an annular concave groove formed in a lower end portion, having different lengths and used for hydrogen analysis.

As shown in FIGS. 1, 2 and 7A to 7B, a supply hole 319 for supplying one crucible R is provided in the cover body 31y. This supply hole 319 is a through-hole formed slightly larger in outside diameter than the crucible R. By providing this through-hole 319, the crucibles R can be supplied appropriately. Besides, even if the crucible R is added from the supply hole 319, the safety structure against overturning 6 (opposing surface 318) can prevent the supplied crucible R from overturning, thus facilitating supplying.

The guide passage 32 drops each crucible R almost vertically and guides the crucible R to the crucible installation part 33. As shown in FIG. 2, one end of the guide passage 32 is open as an introduction port 32a for introducing each crucible R and the other end thereof is open upward of the crucible installation part 33 as an outlet port 32b for discharging the crucible R. The guide passage 32 according to the present embodiment is formed almost vertically by a guide tube 5 of a generally cylindrical shape and the introduction port 32a of the guide passage 32 communicates with a discharge port 312 of the crucible accommodation part 31.

Moreover, the guide passage 32 drops the crucible R introduced from the crucible accommodation part 31 in a state in which upper and lower sides of the crucible R remain set in a right direction. The guide passage 32 has an inside diameter at which the crucible R is not installed upside down when the crucible R falls or, for example, an inside diameter smaller than a length of a longest diagonal of the crucible R.

One or a plurality of through-holes 5A of, for example, a slit shape is provided in a sidewall of the guide tube 5 for discharging foreign matters (such as fragments) other than crucible R introduced from the feed port 314 to outside of the guide tube 5 without arrival at the outlet (outlet port 32b). Specifically, one through-hole 5A is provided downward of a sidewall of a bent portion 51 of the guide tube 5 which portion is provided almost perpendicularly to the inclined mount surface 311. The fragments are thereby discharged to the outside of the guide tube 5 through the through-hole 5A by an empty weight of each fragment. Furthermore, this through-hole 5A makes it possible to confirm whether or not the crucibles R clog in the guide passage 32.

Moreover, a tapered portion 321 is formed near the outlet of the guide passage 32 for reducing a drop velocity of the crucible R. A smallest diameter of this tapered portion 321 is slightly larger than an outside diameter of the crucible R so that the crucible R can pass through the tapered portion 321. Further, a downstream side of the tapered portion 321 of the guide passage 32 has a diameter identical to the smallest diameter of the tapered portion 321. By so forming the tapered portion 321, the drop velocity of the crucible R near the outlet port 32a of the guide passage 32 can be reduced and the crucible R can be prevented from being damaged when the crucible R grounds on the crucible installation part 33. Besides, the tapered portion 321 can prevent displacement of an installation position of the crucible R on the crucible installation part 33 and the crucible R can be installed with high accuracy.

As shown in FIGS. 1 and 2, the crucible installation part 33 is provided in a tip end portion of a driving shaft 341 of an elevating mechanism 34 configured to include an air cylinder or the like and provided on the base 101. The crucible installation part 33 vertically moves between a receiving position Q1 at which the crucible installation part 33 is connected to the guide passage 32 and receives the dropped crucible R and a crucible transport position Q2 that is a distant position away from the receiving position Q1 vertically downward.

Specifically, the crucible installation part 33 includes a concave portion 331x in which one crucible R can be accommodated, a crucible receiver main body 331 receiving the crucible R and a mount protrusion 332 provided in the concave portion 331x of the crucible receiver main body 331.

The crucible receiver main body 331 has a generally bottomed cylindrical shape and an inside diameter of the concave portion 331x is larger than the outside diameter of the crucible R. Furthermore, a tapered surface 331t is formed on an outer circumferential surface of an upper end of the crucible receiver main body 331. As the crucible installation part 33 moves from the crucible transport position Q2 to the receiving position Q1, the tapered surface 331t is fitted into a tapered surface 5t provided on an outlet-side end surface of the guide tube 5 forming the guide passage 32, thereby fulfilling a positioning function of positioning the crucible receiver main body 331, the mount protrusion 332 and the guide passage 32 with respect to one another (see FIG. 2).

The mount protrusion 332 is generally cylindrical and a diameter of the mount protrusion 332 is set slightly smaller than an opening diameter of the crucible R. The mount protrusion 332 is provided coaxially with the crucible receiver main body 331 in the concave portion 331x of the crucible receiver main body 331. If the crucible R is installed with the upper and lower sides of the crucible R set in the right direction, the crucible R is mounted on an almost horizontal upper surface 332a of the mount protrusion 332. On the other hand, if the crucible R is installed upside down, the mount protrusion 33 is contained in the crucible R. By so constituting, a height position of the crucible R on the crucible installation part 33 differs between the instance of installing the crucible R with the upper and lower sides set in the right direction and the instance of installing the crucible R upside down.

A length of the mount protrusion 332 is set larger than a depth of any of various types of crucibles R to be used, thus providing a structure available irrespectively of the size of the crucible R. That is, the length of the mount protrusion 332 is set to a length at which an opening of the crucible R does not contact with a bottom of the concave portion 331x if the crucible R is installed upside down. In other words, the length of the mount protrusion 332 is set to form a space between the bottom of the concave portion 331x and an end surface of the opening of the crucible R. By so setting, even if such foreign matters as fragments of the crucible R are accumulated in the concave portion 331x, the crucible receiver main body 331 can accommodate the crucible R upside down.

As shown in FIGS. 1 and 2, this crucible feeder mechanism 3 also includes a crucible detection sensor 41 and the crucible detection sensor 41 and the crucible installation part 33 constitute an inversion detection mechanism 4.

The crucible detection sensor 41 is a sensor using light and detecting the crucible R only if the crucible R is installed on the mount protrusion 332 with the upper and lower sides thereof set in the right direction. Specifically, a photoelectric sensor is used as the crucible detection sensor 41. The photoelectric sensor 41 is configured so that an orbit of a light L1 emitted from a light emitting part of the photoelectric sensor 41 and reaching a light receiving part thereof is reflected by an outer circumferential surface of the crucible R installed on the crucible installation part 33 with the upper and lower sides thereof set in the right direction and reaches the light receiving part.

By so configuring the photoelectric sensor 41, if the crucible R is installed with the upper and lower sides thereof set in the right direction, the light L1 emitted from the light emitting part is reflected by a side surface of the crucible R and received by the light receiving part of the photoelectric sensor 41. On the other hand, if the crucible R is installed upside down, the light L1 emitted from the light emitting part is not reflected by the outer circumferential surface of the crucible R and not received by the light receiving part. In this way, the light receiving part does not receive the light L1 if the crucible R is not installed on the crucible installation part 33 or the crucible R is installed but installed upside down. Therefore, it is possible to detect whether or not the crucible R is present and whether or not the crucible R is inverted. Moreover, a detection signal of the light receiving part is output to notification means, not shown, so as to notify an operator of detection by an alarm or the like. The crucible detection sensor 41 is not limited to the reflection sensor stated above but may be a transmission sensor, a sensor using ultrasonic wave or the like.

Advantages of First Embodiment

According to the elementary analysis device 100 according to the first embodiment configured as stated above, the crucibles R are mounted in parallel and the number of accommodated crucibles R can be, therefore, increased. Further, one of the crucibles R sliding down the mount surface 311 by the empty weight of the crucible R is guided to the outlet port 312a by the guide member 312, and the guided crucible R slides down in the accommodation concave portion 3131x as it is and transported to the feed port 314. Therefore, the crucible feeder mechanism 3 can be made simple in configuration and the manufacturing cost can be reduced. Particularly in the present embodiment, the crucibles R can be accommodated one by one and fed to the feed port 314 only by rotating the crucible moving body 3131 once. Therefore, the crucible feeder mechanism 3 can be configured quite simply. In this way, the crucible feeder mechanism 3 is made simple in configuration and the crucibles R are mounted in parallel, whereby the crucible feeder mechanism 3 can be made small in size.

Modifications of First Embodiment

The present invention is not limited to the first embodiment. Modifications of the first embodiment will be described. Constituent elements corresponding to those according to the first embodiment will be denoted by the same reference symbols as those used in the first embodiment.

For example, the crucible moving body 3131 according to the first embodiment has one accommodation concave portion 3131x in the circumferential surface portion 3131a of the crucible moving body 3131. Alternatively, a plurality of accommodation concave portions 3131x may be provided on the circumferential surface portion 3131a at predetermined intervals.

Furthermore, not only the graphite crucibles but also ceramic crucibles may be used. In this alternative, the analysis device main body 1 may include a high-frequency heating furnace and may analyze carbon or sulfur present in the sample.

Figure 8:
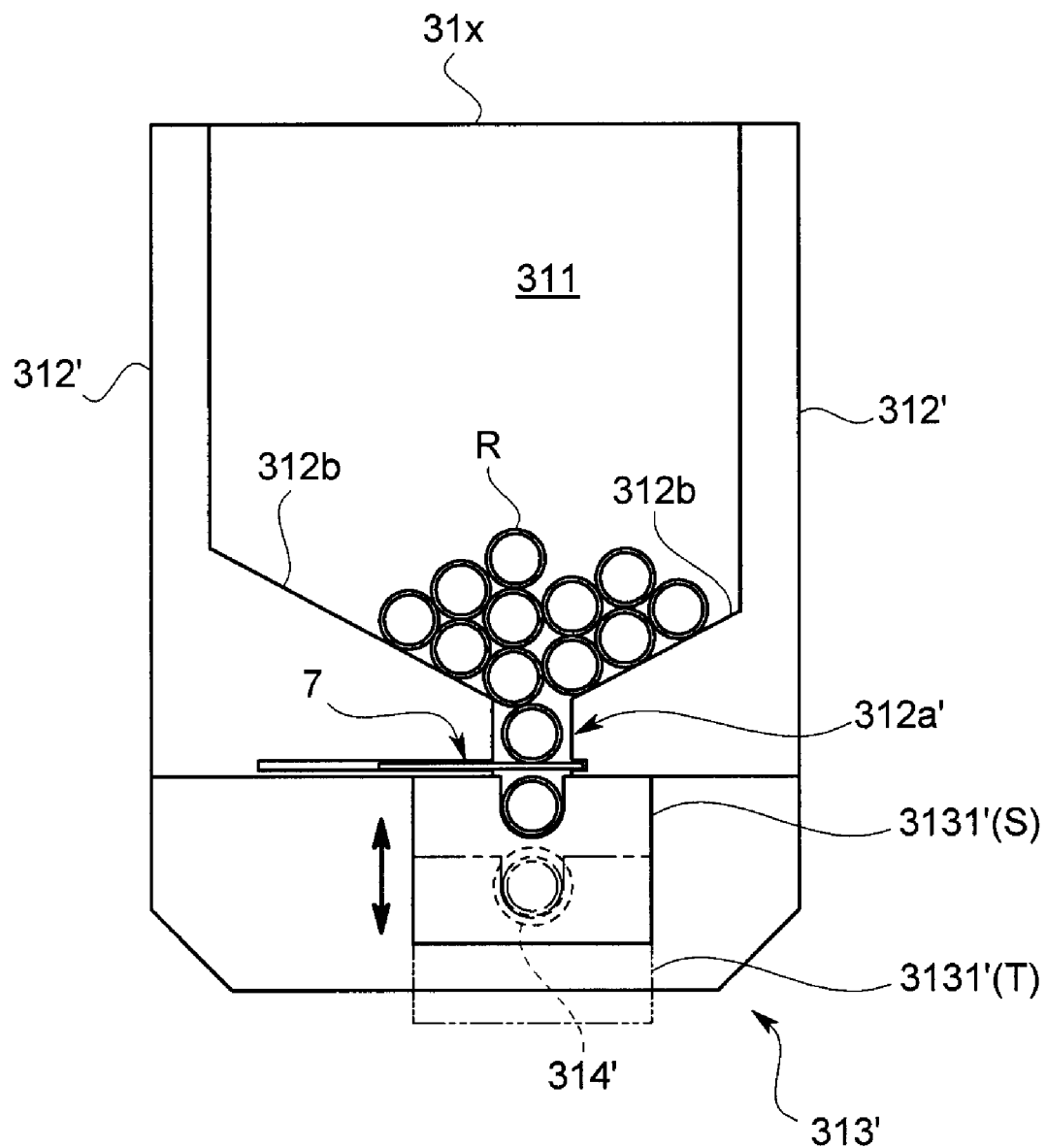
FIG. 8 is a schematic diagram showing a crucible moving mechanism according to a modification of the first embodiment of the present invention.

Moreover, the crucible moving mechanism 313 according to the first embodiment is constituted by a rotating mechanism. Alternatively, the crucible moving mechanism 313 may be constituted by a slide mechanism as shown in FIG. 8. In this alternative, the driving part 3132 drives a crucible moving body 3131' to move forward and backward in a direction along the inclination direction or in a direction perpendicular to the inclination direction with respect to an outlet port 312a' of a guide member 312', thereby moving the crucible moving body 3131' between the accommodation position S and the feed position T. Particularly if the crucible moving body 3131' is driven to move in the direction along the inclination direction with respect to the outlet portion 312a' of the guide member 312', a closing mechanism 7 may be provided at a position distanced from the accommodation position S so that the crucible R does not slide down from the outlet port 312a'.

Second Embodiment

A second embodiment of the present invention will be described. In the second embodiment, different reference symbols from those in the first embodiment are used.

As disclosed in, for example, the Japanese Patent No. 2949501, there is known a sample analysis device that has a measurement sample accommodated in a crucible sandwiched between an upper electrode and a lower electrode, heats and dissolves the measurement sample in the crucible by applying voltage, analyzes gas generated by heating and dissolving the sample and thereby analyzes elements of the measurement sample.

Furthermore, this elementary analysis device drops a crucible from a crucible accommodation part, installs the dropped crucible on a crucible installation part and transports the crucible installed on the crucible installation part onto the lower electrode.

Figure 15:
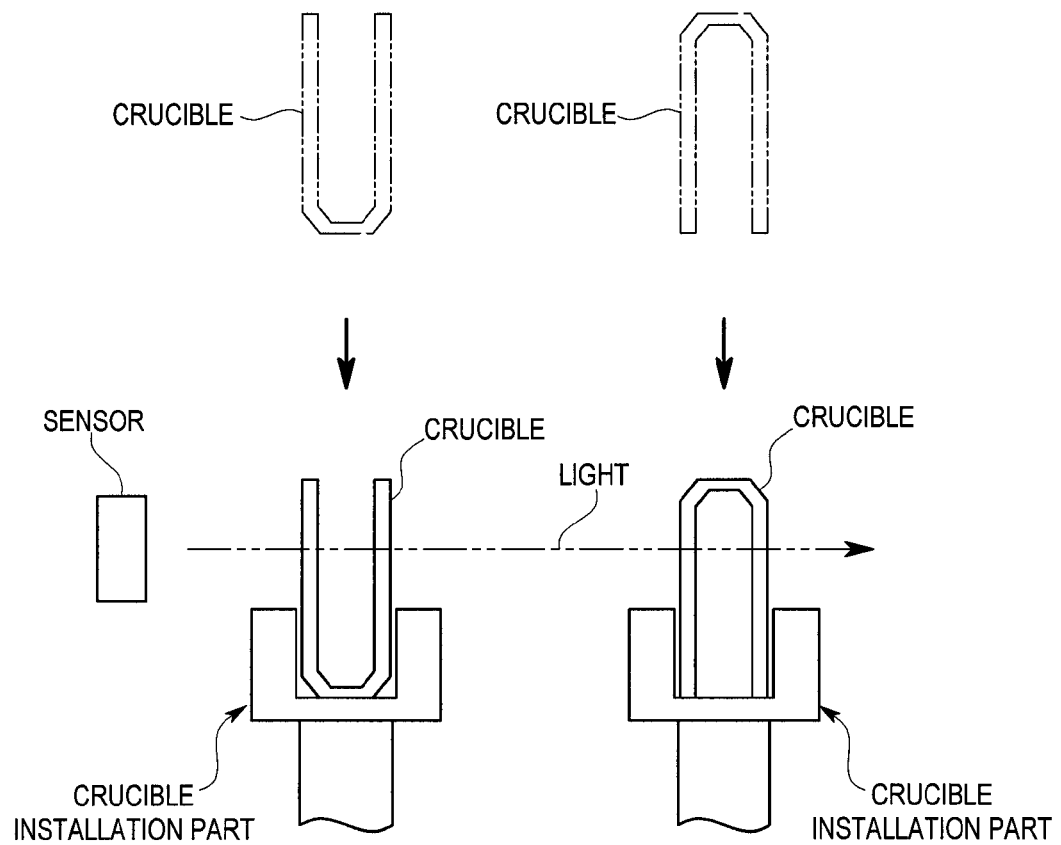
FIG. 15 is a schematic diagram showing a configuration of a conventional crucible installation part.

Conventionally, as shown in FIG. 15, the crucible installation part has a cup shape having an open upper portion and the crucible is mounted on a bottom of a concave portion of the crucible installation part. A photoelectric sensor detects whether or not a crucible is present on the crucible installation part. Specifically, a light emitted from a light emitting part of the photoelectric sensor is reflected by a side surface of the crucible present on the crucible installation part and it is determined whether or not a light receiving part of the photoelectric sensor detects a reflected light, thereby detecting whether or not the crucible is present.

However, the conventional elementary analysis device has the following problems. With this configuration, even if the crucible is installed upside down, the light emitted from the photoelectric sensor is irradiated onto the crucible and reflected by the crucible. Due to this, it can be detected that the crucible is installed but it cannot be detected that the crucible is installed upside down.

Moreover, it is necessary to separately provide a sensor detecting that a crucible is installed upside down so as to detect that the crucible is installed upside down. As a result, such problems occur that it is necessary to secure an installation location of the sensor, manufacturing cost increases and a device configuration is made complicated.

The present invention has been made to solve the problems stated above at a stroke. It is an initial and main object of the present invention to make it possible to determine whether or not a sample container in which such a sample as a crucible is contained is installed upside down while making a crucible feeder mechanism simple in configuration low in cost.

Namely, a sample analysis device according to the present invention includes a container installation part having an open upper portion and installing thereon a sample container containing therein a sample, and analyzing the sample contained in the sample container, wherein the container installation part includes a mount protrusion on which the sample container is mounted if the sample container is installed with upper and lower sides of the sample container set in a right direction, and which is accommodated in the sample container if the sample container is installed upside down.

If the sample analysis device is constituted as stated above, a height position of the sample container on the container installation part differs between an instance of installing the sample container with the upper and lower sides thereof in a right direction and an instance of installing the sample container upside down. Specifically, the height position for the instance of installing the sample container upside down is lower than that for the instance of installing the sample container with the upper and lower sides thereof set in the right direction. Therefore, it is possible to easily determine whether or not the sample container is installed upside down although the sample analysis device is simple in configuration that only the mount protrusion is provided on the sample installation part and low in cost. That is, an operator can visually determine whether or not the sample container is installed upside down based on the height position of the sample container. Further, if it is determined whether or not the sample container is present and whether or not the sample container is installed upside down using a sensor, the sensor is arranged at such a position at which the sensor can detect whether or not the sample container is present if the sensor is installed in a right direction. It is thereby possible to determine both whether or not the sample container is present and whether or not the sample container is installed upside down by using only one sensor.

To appropriately prevent the sample container from overturning if the sample container is installed on the mount protrusion with the upper and lower sides of the sample container set in the right direction, it is preferable that the container installation part includes a safety surface against overturning provided on a side peripheral of the mount protrusion and preventing the sample container from overturning if the sample container is mounted on the mount protrusion with the upper and lower sides of the sample container set in the right direction.

To make it possible to automatically detect whether or not the sample container is present and installed upside down on the container installation part, it is preferable to further include a container detection sensor detecting the sample container only if the sample container is installed on the mount protrusion with the upper and lower sides thereof set in the right direction, and preferable that the container installation part and the container detection sensor constitute an inversion detection mechanism.

In this way, according to the present invention, it is possible to determine whether or not a sample container such as a crucible is installed upside down although the sample analysis device is simple in configuration and low in cost.

Figure 9:
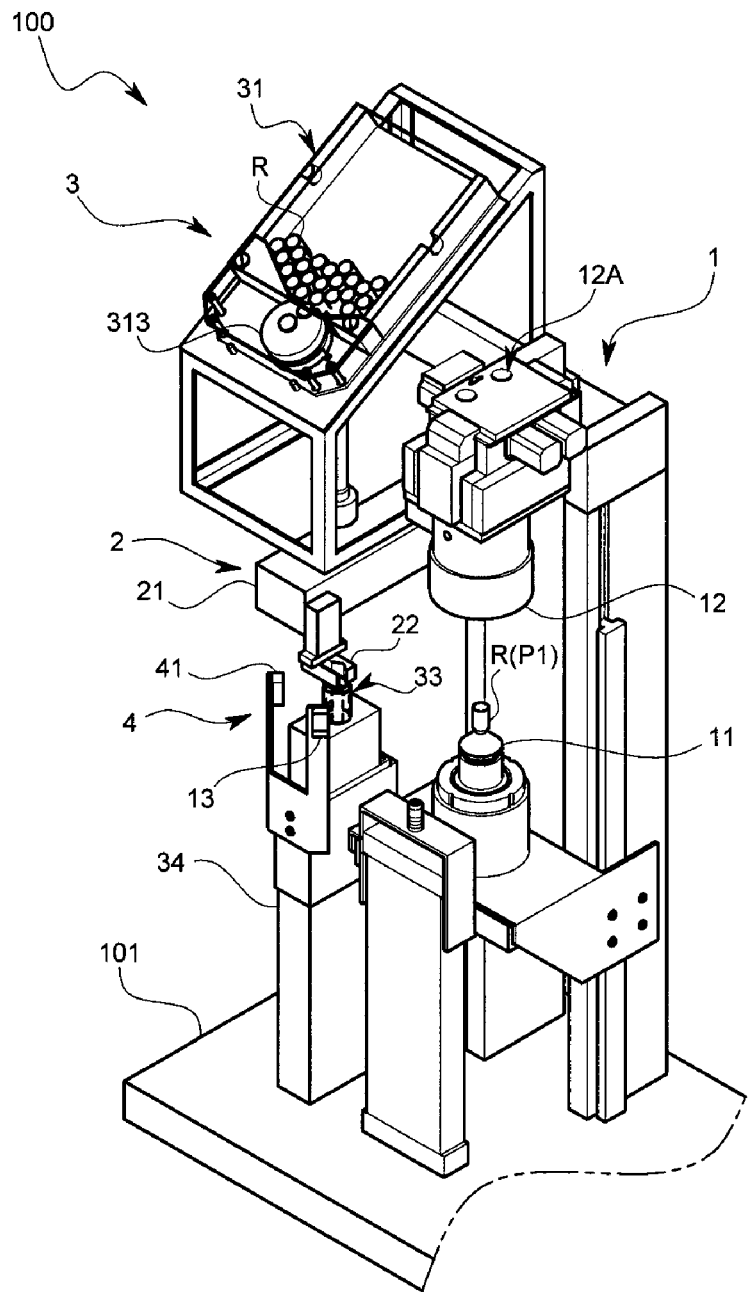
FIG. 9 is a typical configuration diagram of a sample analysis device according to a second embodiment of the present invention.
Figure 10:
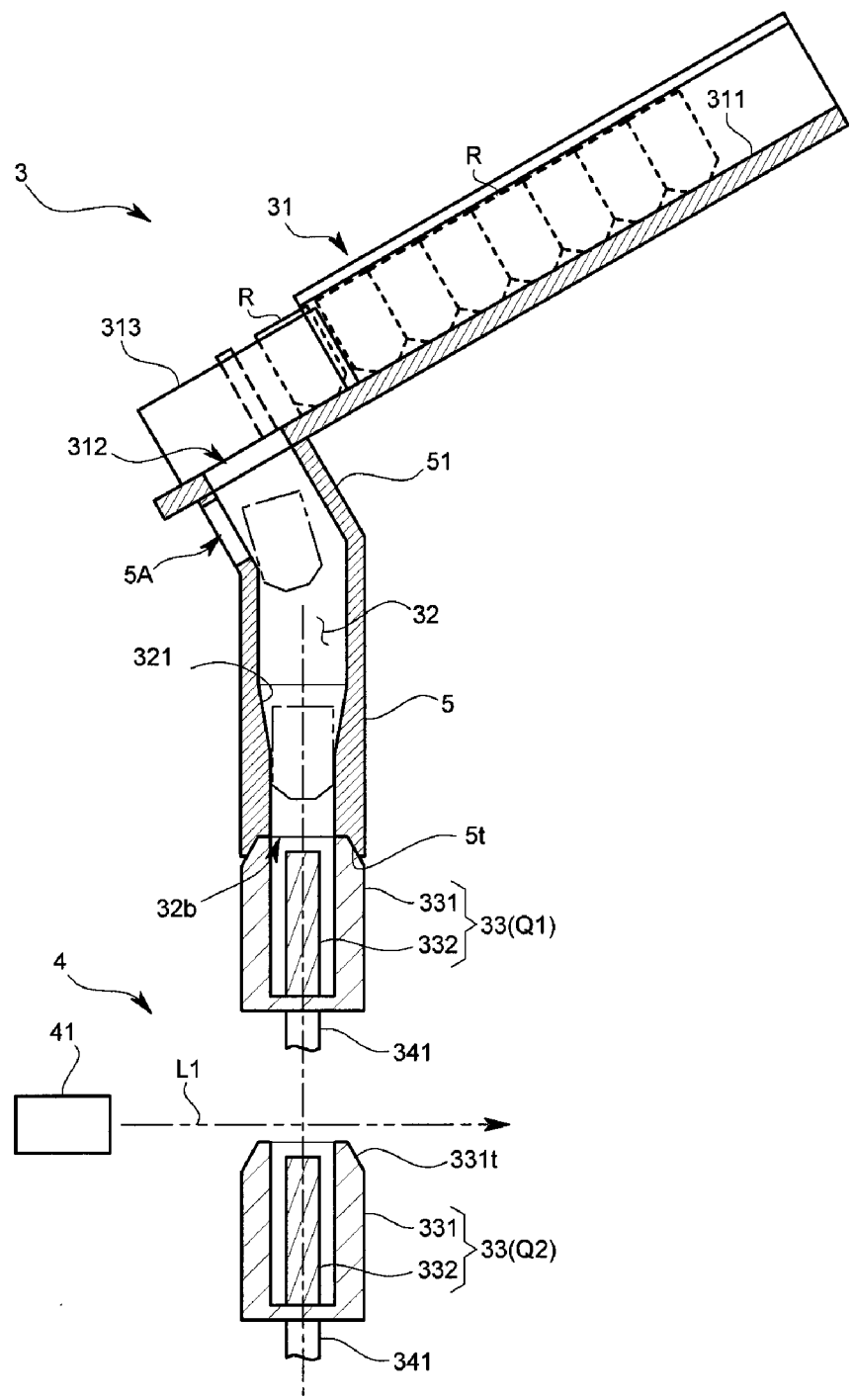
FIG. 10 is a typical configuration diagram of a crucible feeder mechanism according to the second embodiment.
Figure 11:
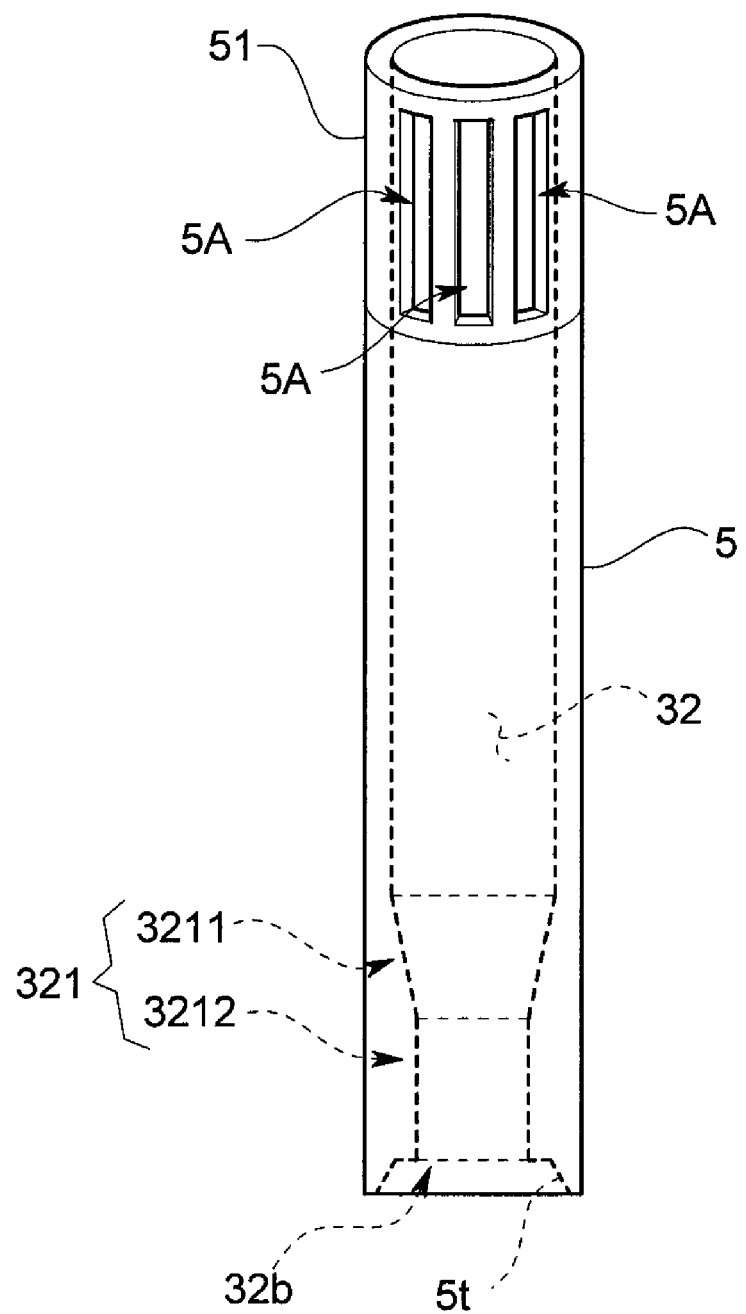
FIG. 11 is a front view of a guide tube according to the second embodiment.
Figure 12:
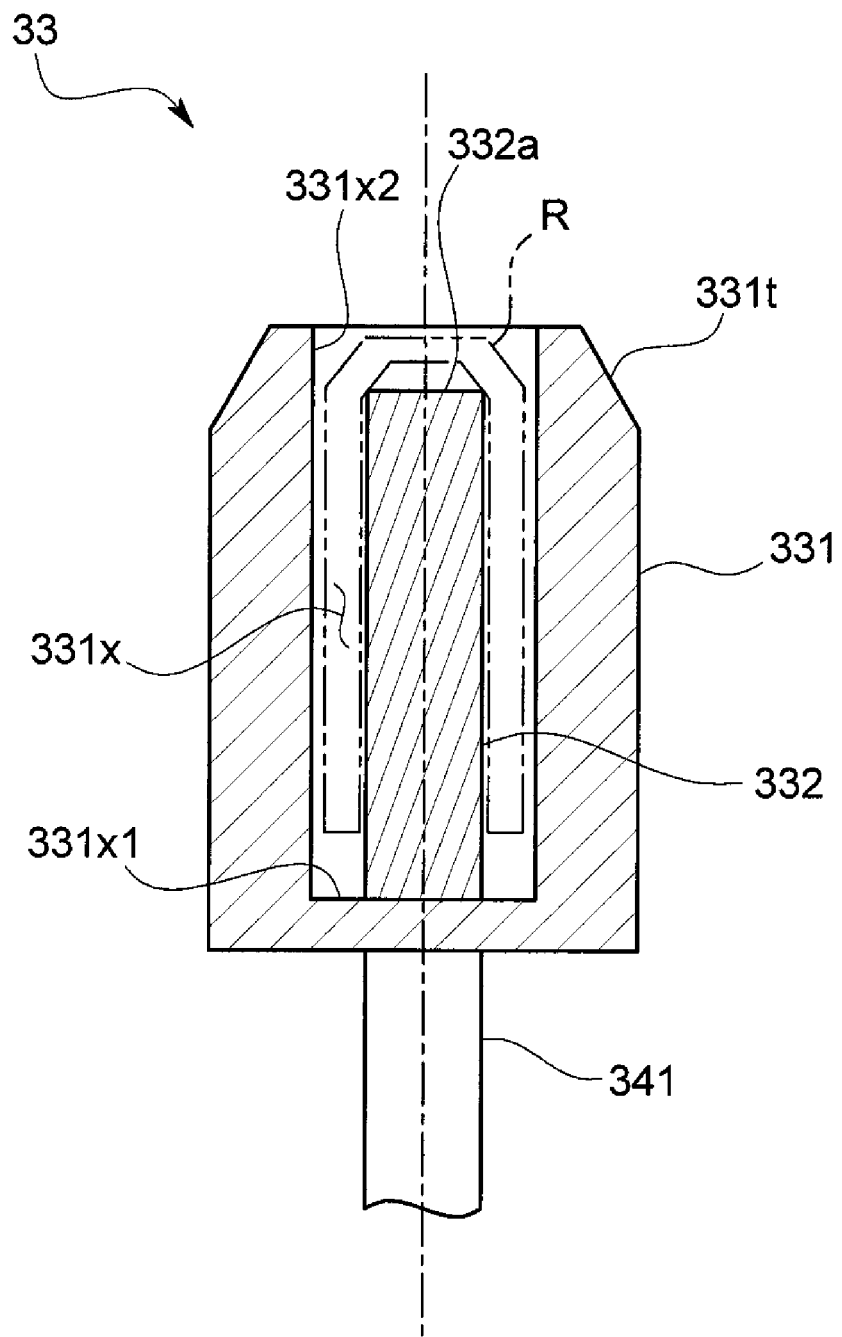
FIG. 12 is an enlarged cross-sectional view showing a configuration of a crucible installation part.
Figure 13:
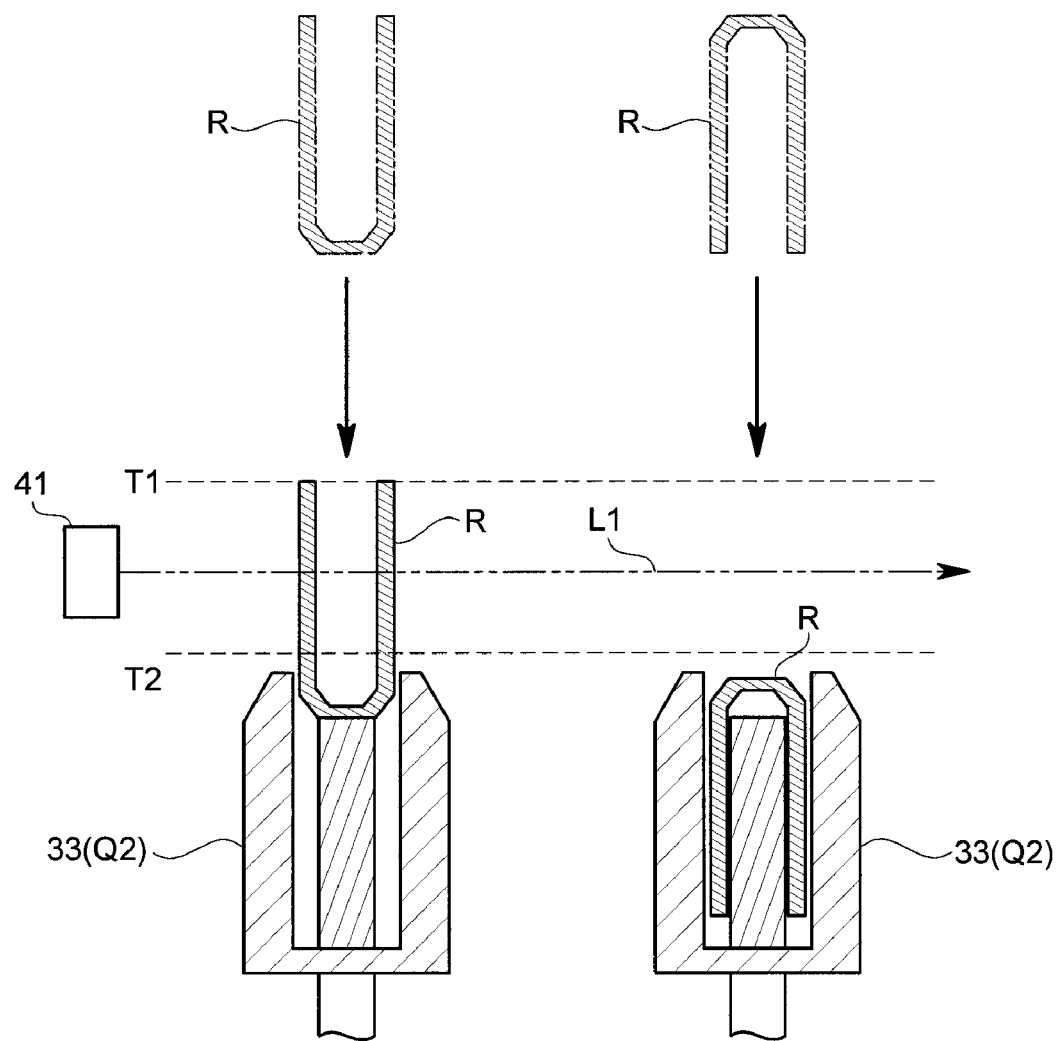
FIG. 13 is a schematic diagram showing an inversion detection mechanism and an inversion detection method.

The second embodiment of the present invention will be described referring to the drawings. FIG. 9 is a schematic configuration diagram of a sample analysis device 100 according to the second embodiment, and FIG. 10 is a typical cross-sectional view showing a configuration of a crucible feeder mechanism 3. FIG. 11 is a front view of a guide tube, FIG. 12 is an enlarged cross-sectional view showing a configuration of a crucible installation part 33 and FIG. 13 is a schematic diagram showing an inversion detection mechanism 4 and an inversion detection method.

<Device Configuration>

The sample analysis device 100 according to the second embodiment heats and dissolves a metal sample (hereinafter, also simply "sample") accommodated in each of crucibles R and analyzes components of gas generated at the time of heating and dissolving, thereby measuring an element contained in the sample. The sample analysis device 100 includes an analysis device main body 1, a crucible transport mechanism 2 transporting the crucibles R to the analysis device main body 1 and a crucible feeder mechanism 3 feeding the crucibles R transported by the crucible transport mechanism 2.

<<Analysis Device Main Body 1>>

The analysis device main body 1 will be described. As shown in FIG. 9, an upper electrode 12 and a lower electrode 11 are provided on a front surface of this analysis device main body 1 to be vertically distanced from each other and the analysis device main body 1 is configured to be able to mount one of the crucibles R in which the sample is accommodated on the lower electrode 11. A position of the crucible R mounted on the lower electrode 11 shown in FIG. 9 is a heating position P1. In FIG. 9, reference symbol 13 denotes a detection sensor (such as a photoelectric sensor) detecting whether or not a crucible R is present on the lower electrode 11. Each crucible R is made of graphite, and has an open upper portion of a cylindrical shape and a tapered lower end portion. The crucible R may have an annular concave groove on an outer circumference of the lower end portion instead of having the tapered lower end portion.

During an analysis, the lower electrode 11 slides upward with respect to the crucible R located at the heating position P1 to sandwich the crucible R between the lower electrode 11 and the upper electrode 12. In this state, when a sample is input into the crucible R from a sample input port 12A provided above the upper electrode 12, then current is applied between the electrodes 11 and 12, heat is generated from the crucible R, and the sample within the crucible R is heated and dissolved. Gas generated from the heated sample is supplied to an analysis part, not shown, components of the gas are measured and elements originally contained in the sample are analyzed as a result of measurement of the gas components.

To measure an amount of oxygen contained in the sample, for example, CO (carbon monoxide) that is a reaction product is generated by heating the sample, CO is measured using, for example, a non-dispersive infrared analyzer constituting the analysis part and the amount of oxygen present in the sample is measured and calculated based on a measured CO value. Furthermore, such components as hydrogen and nitrogen can be measured by setting the reaction product and the analysis part according to the reaction product. After the analysis, the crucible transport mechanism 2 disposes of the used crucible R as well as the sample.

<<Crucible Transport Mechanism 2>>

As shown in FIG. 9, the crucible transport mechanism 2 transports the crucible R installed on a crucible installation part 33, to be described later, to the heating position P1 in the analysis device main body 1. The crucible transport mechanism 2 includes an arm part 21 movable forward and backward with respect to the heating position P1 (lower electrode 11), a drive mechanism (not shown) driving the arm part 21 and a pair of grip clutches 22 attached to a tip end of the arm part 21. The crucible transport mechanism 2 is controlled by an instruction from a controller (not shown) provided separately.

A proximal end portion of the arm part 21 is connected to a rotary shaft of the drive mechanism provided on a base 101. This drive mechanism drives the arm part 21 to rotate and move forward and backward between the heating position P1 and a retreat position away from the heating position P1. The retreat position is located outward of the crucible installation part 33 with respect to the heating position P1. Further, at least one of the grip clutches 22 is, for example, generally doglegged. Each of the grip clutches 22 is held to be able to be driven to slide on the proximal end portion of the arm part 21. The crucible transport mechanism 2 is configured to be able to sandwich and grip a side circumferential surface of the crucible R between central portions of the grip clutches 22 by driving the clutches 22 to slide to narrow a distance between the clutches 22 in response to an instruction from the controller.

Operation performed by the crucible transport mechanism 2 will be described. During transport of one of the crucibles R, the arm part 2 rotates and moves from the retreat position and arrives at the crucible installation part 33. The grip clutches 21 grip the crucible R installed on the crucible installation part 33. Thereafter, the arm part 22 rotates and moves again to the heating position P1 and mounts the crucible R at the heating position P1 (onto the lower electrode 11). After mounting, the arm part 2 returns to the retreat position. Moreover, after an analysis, the arm part 21 moves from the retreat position to the heating position P1, the grip clutches 21 grip the crucible R present on the lower electrode 11 and the crucible transport mechanism 2 transports the crucible R to a disposal container, not shown, and disposes the crucible R.

<<Crucible Feeder Mechanism 3>>

The crucible feeder mechanism 3 automatically feeds the crucible R transported by the crucible transport mechanism 2. Particularly shown in FIG. 10, the crucible feeder mechanism 3 includes a crucible accommodation part 31 in which a plurality of crucibles R can be accommodated, a guide passage 32 dropping each crucible R from the crucible accommodation part 31 by an empty weight of the crucible R and the crucible installation part 33 provided at an outlet port 32b of the guide passage 32 and receiving the dropped crucible R.

The crucible accommodation part 31 includes an inclined surface 311 on which a plurality of crucibles R is mounted in parallel, a discharge port 312 provided downward of the inclined surface 311 and a crucible discharge mechanism 313 holding one of the crucibles R sliding downward of the inclined surface 311 and moving the crucible R to the discharge port 312. The discharge mechanism 313 is configured to include, for example, a rotating body (see FIG. 9) having a concave portion formed on a side surface, accommodating therein the crucible R and rotating uniaxially about a shaft and a driving part (not shown) driving the rotating body to rotate, and to move the crucible R to the discharge port 312 by rotating the crucible R accommodated in the concave portion. The crucible discharge mechanism 313 drops and discharges the crucible R moved to an upper portion of the discharge port 312 from the discharge port 312 by the empty weight of the crucible R. With this configuration, since the crucibles R are accommodated in parallel, the crucibles R can be accommodated as many as possible. Furthermore, since the crucibles R are discharged using the empty weight of each crucible R, the discharge mechanism 313 can be made simple in structure.

The guide passage 32 drops each crucible R almost vertically and guides the crucible R to the crucible installation part 33. As shown in FIG. 10, the guide passage 32 communicates with the discharge port 312 of the crucible accommodation part 31 and is formed almost vertically.

Moreover, the guide passage 32 drops the crucible R introduced from the crucible accommodation part 31 in a state in which upper and lower sides of the crucible R remain set in a right direction. The guide passage 32 has an inside diameter at which the crucible R is not installed upside down when the crucible R falls or, for example, an inside diameter smaller than a length of a longest diagonal of the crucible R.

One or a plurality of (three in FIG. 11) through-holes 5A of, for example, a slit shape is provided in a sidewall of the guide tube 5 for discharging foreign matters (such as fragments of the crucible R) other than the crucible R introduced from the feed port 312 to outside of the guide tube 5 without arrival at the outlet (outlet port 32b). Specifically, the through-holes 5A are provided downward of a sidewall of a bent portion 51 of the guide tube 5 which portion is provided almost perpendicularly to the inclined surface 311. The fragments are thereby discharged to the outside of the guide tube 5 through the through-holes 5A by an empty weight of each fragment. Furthermore, these through-holes 5A make it possible to confirm whether or not the crucibles R clog in the guide passage 32.

Moreover, a tapered portion 321 is formed near the outlet of the guide passage 32 for reducing a drop velocity of the crucible R. A smallest diameter of this tapered portion 321 is slightly larger than an outside diameter of the crucible R so that the crucible R can pass through the tapered portion 321. Further, a downstream side of the tapered portion 321 of the guide passage 32 has a diameter identical to the smallest diameter of the tapered portion 321. By so forming the tapered portion 321, the drop velocity of the crucible R near the outlet port 32a of the guide passage 32 can be reduced and the crucible R can be prevented from being damaged when the crucible R grounds on the crucible installation part 33. Besides, the tapered portion 321 can prevent displacement of an installation position of the crucible R on the crucible installation part 33 and the crucible R can be installed with high accuracy.

As shown in FIGS. 9 and 10, the crucible installation part 33 is provided in a tip end portion of a driving shaft 341 of an elevating mechanism 34 configured to include an air cylinder or the like and provided on a base 101. The crucible installation part 33 vertically moves between a receiving position Q1 at which the crucible installation part 33 is connected to the guide passage 32 and receives the dropped crucible R and a crucible transport position Q2 that is a distant position away from the receiving position Q1 vertically downward. The crucible installation part 33 will be described later in detail.

<<Inversion Detection Mechanism 4>>

Moreover, as shown in FIGS. 9 and 10, the crucible feeder mechanism 3 according to the present embodiment includes the inversion detection mechanism 4 for detecting whether a crucible R is turned upside down. The crucible installation part 33 and a crucible detection sensor 41 constitute this inversion detection mechanism 4.

Specifically, as shown in FIG. 12, the crucible installation part 33 includes a concave portion 331x in which one crucible R can be accommodated, a crucible receiver main body 331 receiving the crucible R and a mount protrusion 332 provided in the concave portion 331x of the crucible receiver main body 331.

The crucible receiver main body 331 has a generally bottomed cylindrical shape and an interior made of visually recognizable transparent resin. An inside diameter of the concave portion 331x is larger than an outside diameter of the crucible R. Furthermore, a tapered surface 331t is formed on an outer circumferential surface of an upper end of the crucible receiver main body 331. As the crucible installation part 33 moves from the crucible transport position Q2 to the receiving position Q1, the tapered surface 331t is fitted into a tapered surface 5t provided on an outlet-side end surface of the guide tube 5 forming the guide passage 32, thereby fulfilling a positioning function of positioning the crucible receiver main body 331, the mount protrusion 332 and the guide passage 32 with respect to one another (see FIG. 10).

The mount protrusion 332 is provided coaxially in the concave portion 331x of the crucible receiver main body 331. If the crucible R is installed with the upper and lower sides of the crucible R set in the right direction, the crucible R is mounted on an almost horizontal upper surface 332a of the mount protrusion 332. On the other hand, if the crucible R is installed upside down, the mount protrusion 33 is contained in the crucible R. By so configuring, a height position of the crucible R on the crucible installation part 33 differs between an instance of installing the crucible R with the upper and lower sides set in the right direction and the instance of installing the crucible R upside down.

The mount protrusion 332 according to the present embodiment is fixed to a bottom 331x1 of the concave portion 331x of the crucible receiver main body 331. Alternatively, the mount protrusion 332 may be fixed to a driving shaft 341 of the elevating mechanism 34 while passing through a through-hole provided almost in a central portion of the crucible receiver main body 331.

Specifically, the mount protrusion 332 is generally cylindrical and a diameter of the mount protrusion 332 is set slightly smaller than an opening diameter of the crucible R. More specifically, the diameter of the mount protrusion 332 is set as large as possible in a range smaller than the opening diameter of the crucible so as to stably mount the crucible R with the upper and lower sides thereof set in the right direction, and so as to fit the crucible R into the mount protrusion 332 by the empty weight of the crucible R when the crucible R is installed upside down.

A length of the mount protrusion 332 is set larger than a depth of any of various types of crucibles R to be used, thus providing a structure available irrespectively of the size of the crucible R. That is, the length of the mount protrusion 332 is set to a length at which an opening of the crucible R does not contact with the bottom 331x1 of the concave portion if the crucible R is installed upside down. In other words, the length of the mount protrusion 332 is set to form a space between the bottom 331x1 of the concave portion and an end surface of the opening of the crucible R. By so setting, even if such foreign matters as fragments of the crucible R are accumulated in the concave portion 331x, the crucible receiver main body 331 can accommodate the crucible R upside down.

Moreover, the mount protrusion 332 has the length enough to be accommodated in the concave portion 331x of the crucible receiver main body 331. An inner peripheral surface 331x2 of the concave portion 331x of the crucible receiver main body 331 is thereby provided around the mount protrusion 332 equidistantly from an outer peripheral surface thereof in an upper portion of the mount protrusion 332. In this case, if the crucible R is installed on the mount protrusion 332 with the upper and lower sides thereof set in the right direction, the inner peripheral surface 331x2 of the concave portion 331x functions as a safety surface against overturning for preventing the crucible R from overturning.

The crucible detection sensor 41 is a sensor using light and detecting the crucible R only if the crucible R is installed on the mount protrusion 332 with the upper and lower sides thereof set in the right direction. Specifically, a photoelectric sensor is used as the crucible detection sensor 41. The photoelectric sensor 41 is configured so that an orbit of a light L1 emitted from a light emitting part of the photoelectric sensor 41 and reaching a light receiving part thereof is reflected by an outer circumferential surface of the crucible R installed on the crucible installation part 33 with the upper and lower sides thereof set in the right direction and reaches the light receiving part.

Specifically, the crucible detection sensor 41 is installed at a position lateral to the crucible transport position Q2 of the crucible installation part 33 as shown in FIG. 13. More specifically, the crucible detection sensor 41 is provided so that a height position of the light L1 emitted from the light emitting part of the crucible detection sensor 41 is located between a height position T1 for the instance of installing the crucible R with the upper and lower sides thereof set in the right direction and a height position T2 for the instance of installing the crucible R upside down. In this case, the height positions T1 and T2 refer to height positions of an uppermost end of the crucible R in respective installation states. For example, the height position T1 for the instance in which the crucible R is installed with the upper and lower sides thereof set in the right direction corresponds to a height position of an upper surface in which an opening of the crucible R is provided. The height position T2 for the instance in which the crucible R is installed upside down corresponds to a height position of a bottom of the crucible R. In the present embodiment, if the crucible R is installed upside down, the crucible R is accommodated and hidden from the sight in the crucible receiver main body 331 in a side view. Due to this, the height position T2 is set higher than that of an uppermost end of the crucible receiver main body 331.

By so configuring the photoelectric sensor 41, if the crucible R is installed with the upper and lower sides thereof set in the right direction, the light L1 emitted from the light emitting part is reflected by a side surface of the crucible R and received by the light receiving part of the photoelectric sensor 41. On the other hand, if the crucible R is installed upside down, the light L1 emitted from the light emitting part is not reflected by the outer circumferential surface of the crucible R and not received by the light receiving part. In this way, the light receiving part does not receive the light L1 if the crucible R is not installed on the crucible installation part 33 or the crucible R is installed but installed upside down. Therefore, it is possible to detect whether or not the crucible R is present and whether or not the crucible R is inverted. Moreover, a detection signal of the light receiving part is output to notification means, not shown, so as to notify an operator of detection by an alarm or the like. The crucible detection sensor 41 is not limited to the reflection sensor stated above but may be a transmission sensor, a sensor using ultrasonic wave or the like.

Advantages of Second Embodiment

According to the sample analysis device 1 according to the second embodiment configured as stated above, the height position of the crucible R on the crucible installation part 33 differs between the instance of installing the crucible R on the crucible installation part 3 with the upper and lower sides thereof set in the right direction and the instance of installing the crucible R thereon upside down. Specifically, the height position of the crucible R for the instance of installing the crucible R upside down is lower than that for the instance of installing the crucible R with the upper and lower sides thereof set in the right direction. Furthermore, since the crucible R is arranged at the height at which the crucible R can be detected only if the sensor is installed in a right direction, it is possible to determine both whether or not the sample container is present and whether or not the sample container is installed upside down by using only one sensor. Further, the crucible R can be stably installed on the crucible installation part 33 only by dropping such foreign matters as fragments of the crucible R to surroundings of the mount protrusion 332, thus facilitating cleaning the crucible installation part 33.

Modifications of Second Embodiment

The present invention is not limited to the second embodiment. Modifications of the second embodiment will be described. Constituent elements corresponding to those according to the second embodiment will be denoted by the same reference symbols as those used in the second embodiment.

Figure 14:
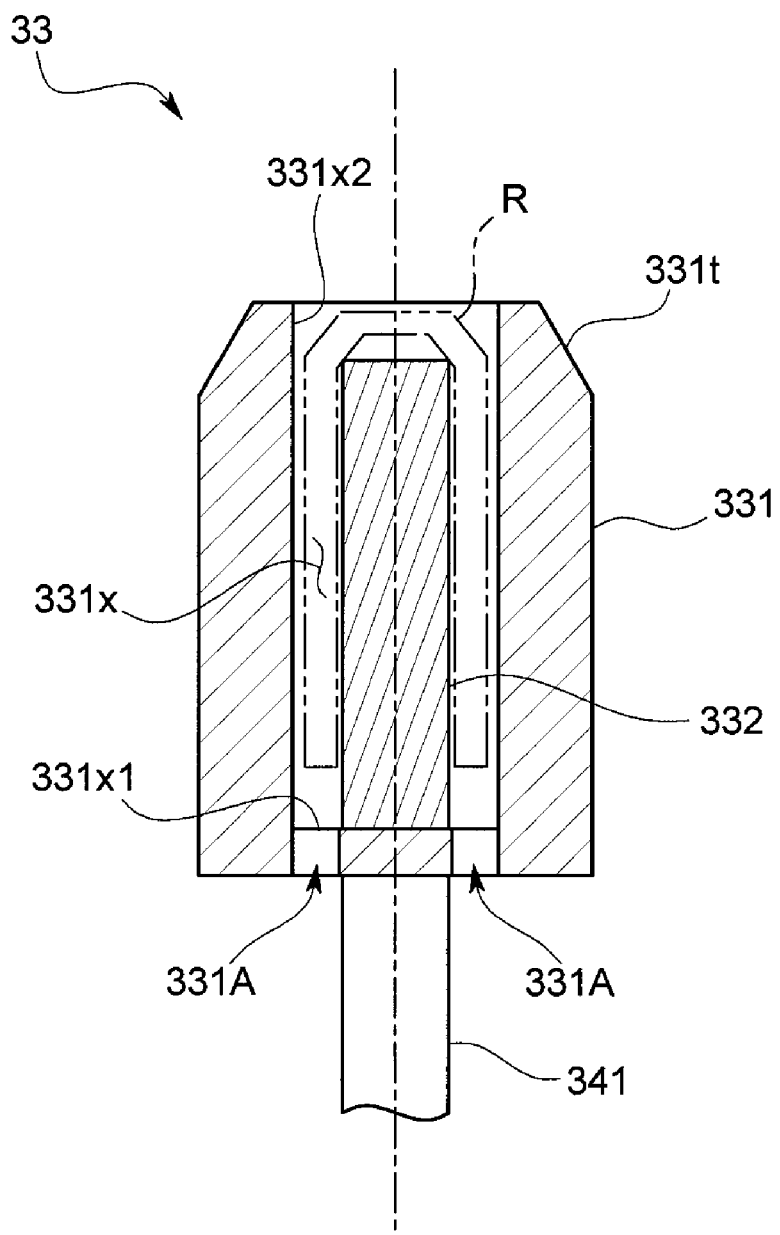
FIG. 14 is a cross-sectional view of a crucible installation part according to a modification of the second embodiment.

For example, as shown in FIG. 14, a discharge port 331A for dropping and discharging such foreign matters as fragments of the crucible R from the crucible receiver main body 331 may be provided in a bottom wall of the crucible receiver main body 331. If the discharge port 331A is provided, such foreign matters as fragments of the crucible R are not accumulated in the crucible receiver main body 331. If the crucible R is installed upside down, it is possible to ensure fitting the crucible R into the mount protrusion 332 without causing the foreign matters to obstruct the crucible R.

Moreover, the mount protrusion according to the second embodiment is cylindrical and the diameter of the mount protrusion is smaller than the opening diameter of the crucible. However, a shape of the mount protrusion is not limited to a cylindrical shape and is not limited to a specific shape as long as the mount protrusion can be accommodated in the crucible R if the crucible R is installed upside down. For example, the mount protrusion may be prismatic.

Furthermore, the length of the mount protrusion is not limited to that according to the second embodiment but can be set according to the length of the crucible (depth of the concave portion). For example, if the crucible is installed upside down, the length of the mount protrusion may be a length at which the opening of the crucible R contacts with the bottom of the concave portion. According to this modification, similarly to the second embodiment, the height position of the crucible on the crucible installation part differs between the instance of installing the crucible with the upper and lower sides thereof set in the right direction and the instance of installing the crucible upside down. Therefore, it is possible to detect both whether or not the crucible is present and whether or not the crucible is turned upside down.

In the second embodiment, the crucible is installed in the crucible installation part from the crucible accommodation part via the guide passage. Alternatively, an operator may install the crucible manually using, for example, tweezers.

Furthermore, not only the graphite crucibles but also ceramic crucibles may be used. In this alternative, the analysis device main body 1 may include a high-frequency heating furnace and may analyze carbon or sulfur present in the sample.

Third Embodiment

A third embodiment of the present invention will be described. In the third embodiment, different reference symbols from those in the first and second embodiments are used.

As disclosed in, for example, the Japanese Patent No. 2949501, an elementary analysis device that has a measurement sample accommodated in a crucible sandwiched between an upper electrode and a lower electrode, heats the measurement sample in the crucible by applying voltage, analyzes gas generated by heating the sample and thereby analyzes elements of the measurement sample. Further, this elementary analysis device includes a crucible feeder mechanism feeding crucibles. A crucible transport mechanism transports each of the crucibles fed by the crucible feeder mechanism onto the lower electrode.

Conventionally, the crucible feeder mechanism drops each of crucibles from a crucible accommodation part accommodating therein a plurality of crucibles via a guide passage and installs the crucible on a crucible installation part provided in a lower portion of the guide passage. Further, the guide passage is set larger in outside diameter than one crucible so as to smoothly drop the crucible without clogging and formed out of a cylindrical member of a uniform sectional shape such as an acrylic pipe. Namely, the guide passage has an equal cross-sectional area until an outlet of the guide passage.

However, the conventional elementary analysis device stated above has the following problems. With such a configuration, a drop velocity of the crucible increases as the crucible drops and the crucible is damaged and broken by an impact generated when the crucible grounds on the crucible installation part.

Moreover, a grounding position of the crucible differs in a range of the cross-sectional area of the guide passage and is possibly displaced from a desired installation position. Further, if the transport mechanism then transports the crucible, the transport mechanism cannot ensure gripping the crucible.

The present invention has been made to solve the problems stated above at a stroke. It is an initial and main object of the present invention to feed crucibles without damaging or breaking the crucibles and to prevent displacement of an installation position of each of the crucibles on a crucible installation part while making a crucible feeder mechanism simple in configuration.

That is, a crucible feeder mechanism according to the present invention is a crucible feeder mechanism used in an elementary analysis device extracting an element contained in a sample accommodated in a crucible as a gas component and analyzing the element by heating the sample, including a crucible installation part in which each of the crucibles is installed so as to transport the crucible to a predetermined heating position; and a guide passage having one end open as an introduction port for introducing each of the crucibles and the other end open upward of the crucible installation part, dropping each of the crucibles, and guiding the crucible to the crucible installation part, wherein a throttle structure decreasing a cross-sectional area of the guide passage and narrowing a passing region of each of the crucibles is provided on an outlet port-side of the guide passage.

If the crucible feeder mechanism is configured as stated above, then each crucible contacts with the throttle structure and a drop velocity of the crucible can be reduced by decreasing the cross-sectional area of the guide passage and narrowing the passing region of the crucible although the crucible feeder mechanism is simple in configuration that the throttle structure is provided on the outlet port-side of the guide passage. Further, since the throttle passing region is narrowed on the outlet port side of the guide passage, it is possible to prevent displacement of the position of the crucible from the desired installation position of the crucible.

To make a configuration of the throttle structure simpler and to ensure smoothly dropping each crucible, it is preferable that the throttle structure includes a tapered portion narrower toward the outlet port of the guide passage.

To make it difficult to accelerate again the crucible reduced by the tapered portion and further to accurately set the crucible grounding position, it is preferable that the throttle structure is continuously provided on a downstream side of the tapered portion and includes a small-diameter portion having a uniform cross section and identical in diameter to a smallest diameter of the tapered portion.

To make adjustable the drop velocity of the crucible in the small-diameter portion, it is preferable to provide an air hole formed in the small-diameter portion and communicating an interior and an exterior of the guide passage with each other. If the air hole is provided, the drop velocity of the crucible can be made adjustable by controlling an amount of the air discharged from the air hole or an amount of the air introduced into the air hole.

If the crucible installation part vertically moves between a receiving position at which the crucible installation part is connected to the guide passage and receives the dropped crucible and a distant position away from the receiving position vertically downward, it is preferable that the crucible installation part includes a positioning mechanism positioning an outlet port of the guide passage and the crucible installation part at the receiving position. It is also preferable that the positioning mechanism includes a concave portion provided on one of the crucible installation part and a member forming the guide passage and a concave portion provided on the other one of the crucible installation part and the member forming the guide passage and fitted into the convex portion.

In this way, according to the present invention, it is possible to feed crucibles without damaging or breaking the crucibles and prevent displacement of a position of each of the crucibles on the crucible installation position while the crucible feeder mechanism is simple in configuration.

Figure 16:
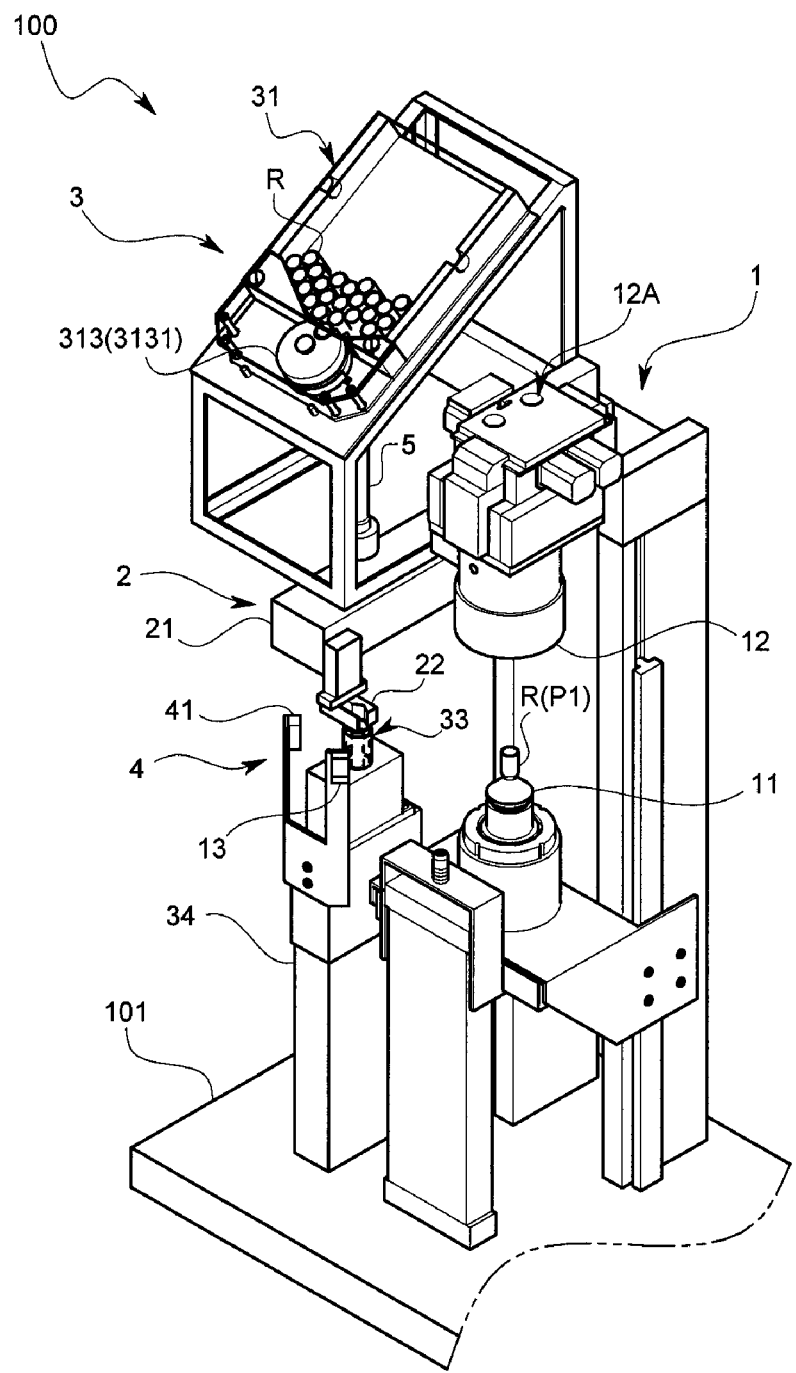
FIG. 16 is a typical configuration diagram of an elementary analysis device according to a third embodiment of the present invention.
Figure 17:
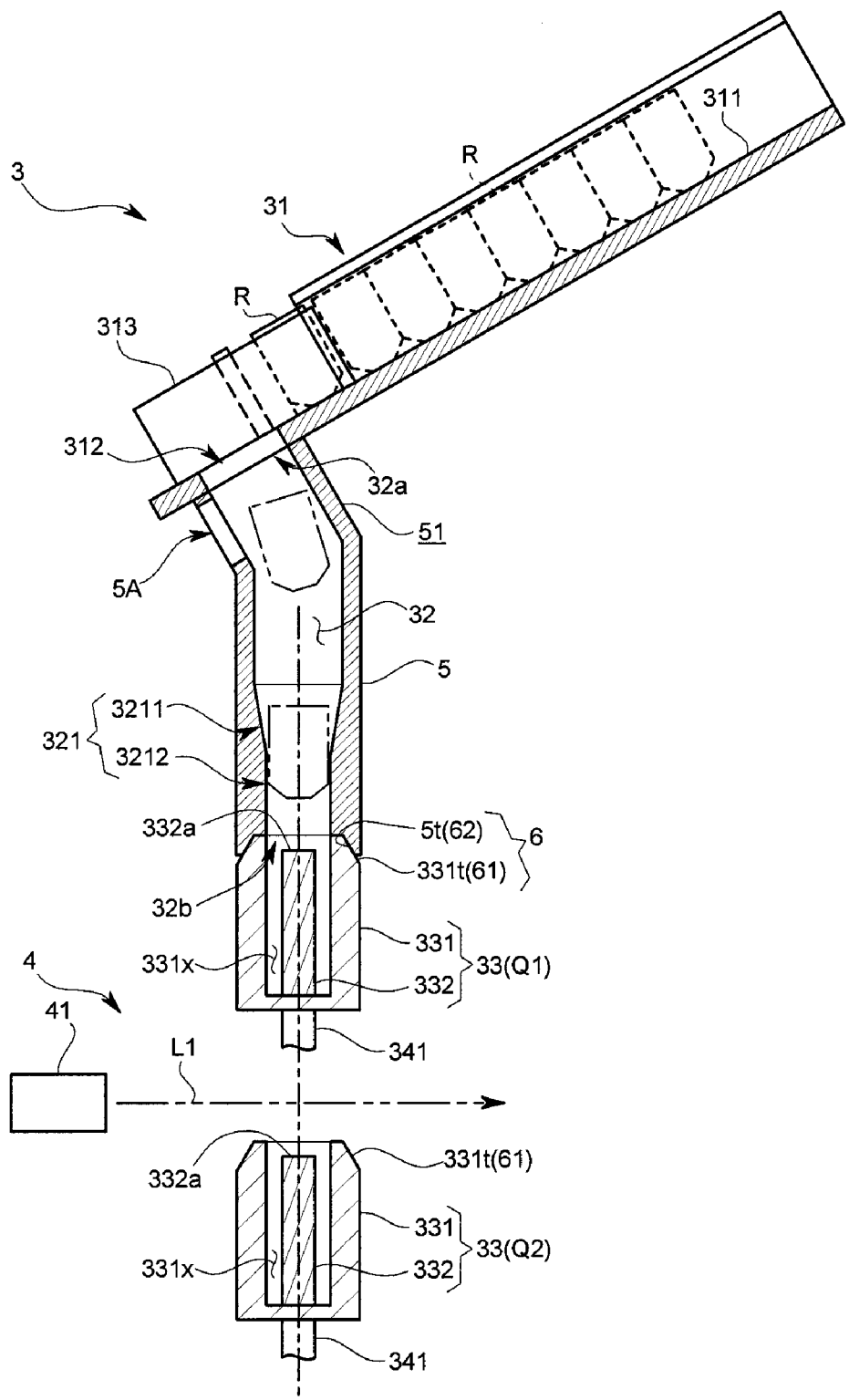
FIG. 17 is a longitudinal sectional view showing a configuration of a crucible feeder mechanism according to the third embodiment.
Figure 18:
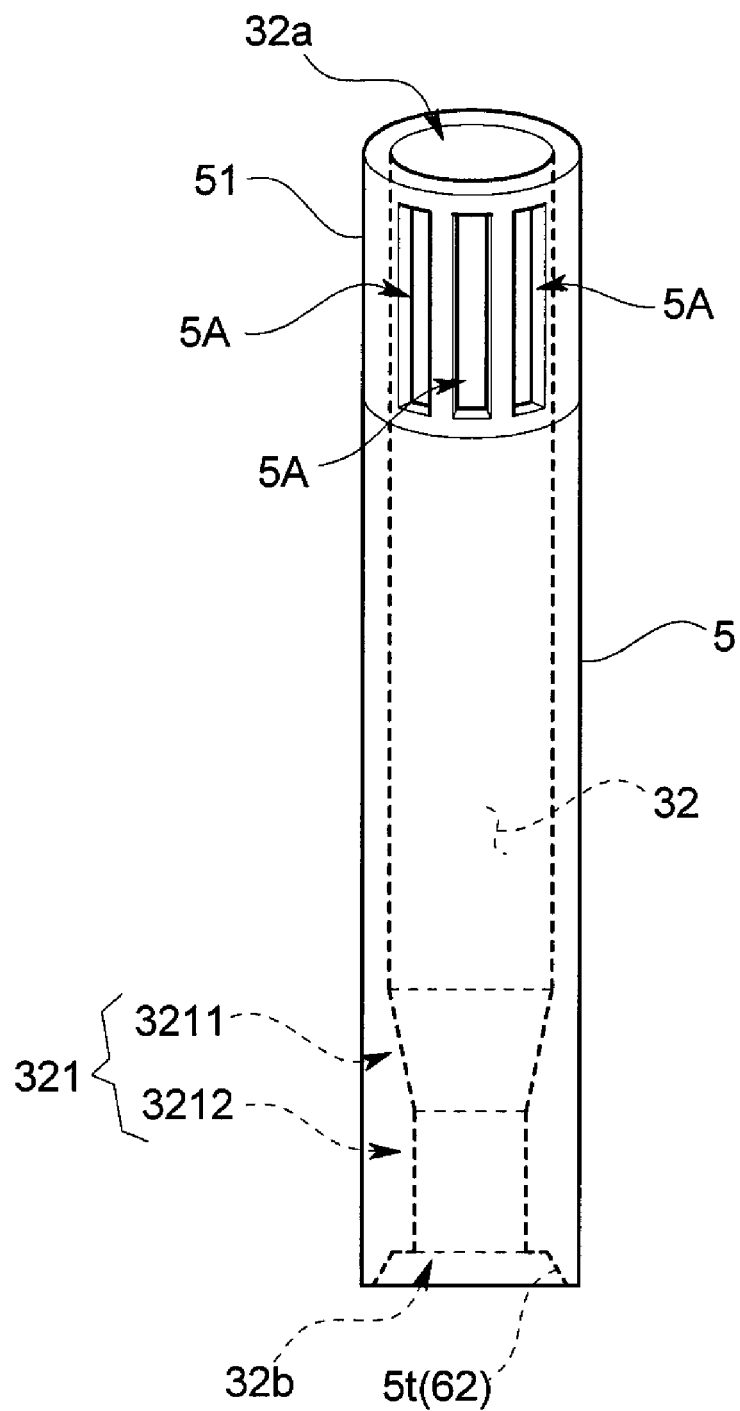
FIG. 18 is a front view of a guide tube according to the third embodiment.

The third embodiment of the present invention will be described referring to the drawings. FIG. 16 is a schematic configuration diagram of an elementary analysis device 100 according to the third embodiment, FIG. 17 is a typical cross-sectional view showing a configuration of a crucible feeder mechanism 3, and FIG. 18 is a front view of a guide tube 5.

<Device Configuration>

The elementary analysis device 100 according to the third embodiment heats a metal sample (hereinafter, also simply "sample") accommodated in each of crucibles R and analyzes components of gas generated at the time of heating, thereby measuring an element contained in the sample. The elementary analysis device 100 includes an analysis device main body 1, a crucible transport mechanism 2 transporting the crucibles R to the analysis device main body 1 and a crucible feeder mechanism 3 feeding the crucibles R transported by the crucible transport mechanism 2. The analysis device main body 1, the crucible transport mechanism 2 and the crucible feeder mechanism 3 will be described, respectively.

<<Analysis Device Main Body 1>>

The analysis device main body 1 will be described. As shown in FIG. 16, an upper electrode 12 and a lower electrode 11 are provided on a front surface of this analysis device main body 1 to be vertically distanced from each other and the analysis device main body 1 is configured to be able to mount one of the crucibles R in which the sample is accommodated on the lower electrode 11. A position of the crucible R mounted on the lower electrode 11 shown in FIG. 16 is a heating position P1. In FIG. 16, reference symbol 13 denotes a detection sensor (such as a photoelectric sensor) detecting whether or not a crucible R is present on the lower electrode 11. Each crucible R is made of graphite, and has an open upper portion of a cylindrical shape and a tapered lower end portion. The crucible R may have an annular concave groove on an outer circumference of the lower end portion instead of having the tapered lower end portion.

During an analysis, the lower electrode 11 slides upward with respect to the crucible R located at the heating position P1 to sandwich the crucible R between the lower electrode 11 and the upper electrode 12. In this state, when a sample is input into the crucible R from a sample input port 12A provided above the upper electrode 12, then current is applied between the electrodes 11 and 12, heat is generated from the crucible R, and the sample within the crucible R is heated. Gas generated from the heated sample is supplied to an analysis part, not shown, components of the gas are measured and elements originally contained in the sample are analyzed as a result of measurement of the gas components.

To measure an amount of oxygen contained in the sample, for example, CO (carbon monoxide) that is a reaction product is generated by heating the sample, CO is measured using, for example, a non-dispersive infrared analyzer constituting the analysis part and the amount of oxygen present in the sample is measured and calculated based on a measured CO value. Furthermore, such components as hydrogen and nitrogen can be measured by setting the reaction product and the analysis part according to the reaction product. After the analysis, the crucible transport mechanism 2 disposes of the used crucible R as well as the sample.

<<Crucible Transport Mechanism 2>>

As shown in FIG. 16, the crucible transport mechanism 2 transports the crucible R installed on a crucible installation part 33, to be described later, to the heating position P1 in the analysis device main body 1. The crucible transport mechanism 2 includes an arm part 21 movable forward and backward with respect to the heating position P1 (lower electrode 11), a drive mechanism (not shown) driving the arm part 21 and a pair of grip clutches 22 attached to a tip end of the arm part 21. The crucible transport mechanism 2 is controlled by an instruction from a controller (not shown) provided separately.

A proximal end portion of the arm part 21 is connected to a rotary shaft of the drive mechanism provided on a base 101. This drive mechanism drives the arm part 21 to rotate and move forward and backward between the heating position P1 and a retreat position away from the heating position P1. The retreat position is located outward of the crucible installation part 33 with respect to the heating position P1. Further, at least one of the grip clutches 22 is, for example, generally doglegged. Each of the grip clutches 22 is held to be able to be driven to slide on the proximal end portion of the arm part 21. The crucible transport mechanism 2 is configured to be able to sandwich and grip a side circumferential surface of the crucible R between central portions of the grip clutches 22 by driving the clutches 22 to slide to narrow a distance between the clutches 22 in response to an instruction from the controller.

Operation performed by the crucible transport mechanism 2 will be described. During transport of one of the crucibles R, the arm part 2 rotates and moves from the retreat position and arrives at the crucible installation part 33. The grip clutches 21 grip the crucible R installed on the crucible installation part 33. Thereafter, the arm part 22 rotates and moves again to the heating position P1 and mounts the crucible R at the heating position P1 (onto the lower electrode 11). After mounting, the arm part 2 returns to the retreat position. Moreover, after an analysis, the arm part 21 moves from the retreat position to the heating position P1, the grip clutches 21 grip the crucible R present on the lower electrode 11 and the crucible transport mechanism 2 transports the crucible R to a disposal container, not shown, and disposes of the crucible R.

<<Crucible Feeder Mechanism 3>>

The crucible feeder mechanism 3 automatically feeds the crucible R transported by the crucible transport mechanism 2. Particularly shown in FIG. 17, the crucible feeder mechanism 3 includes a crucible accommodation part 31 in which a plurality of crucibles R can be accommodated, a guide passage 32 dropping each crucible R from the crucible accommodation part 31 by an empty weight of the crucible R and the crucible installation part 33 provided at an outlet port 32b (an outlet) of the guide passage 32 and receiving the dropped crucible R.

The crucible accommodation part 31 includes an inclined surface 311 on which a plurality of crucibles R is mounted in parallel, a discharge port 312 provided downward of the inclined surface 311 and a crucible discharge mechanism 313 holding one of the crucibles R sliding downward of the inclined surface 311 and moving the crucible R to the discharge port 312. The discharge mechanism 313 is configured to include, for example, a rotating body 3131 (see FIG. 16) having a concave portion formed on a side surface, accommodating therein the crucible R and rotating uniaxially about a shaft and a driving part (not shown) driving the rotating body 3131 to rotate, and to move the crucible R to the discharge port 312 by rotating the crucible R accommodated in the concave portion. The crucible discharge mechanism 313 drops and discharges the crucible R moved to an upper portion of the discharge port 312 from the discharge port 312 by the empty weight of the crucible R. With this configuration, since the crucibles R are accommodated in parallel, the crucibles R can be accommodated as many as possible. Furthermore, since the crucibles R are discharged using the empty weight of each crucible R, the discharge mechanism 313 can be made simple in structure.

The guide passage 32 drops each crucible R almost vertically and guides the crucible R to the crucible installation part 33. As shown in FIGS. 17 and 18, the guide passage 32 has one end open as an introduction port 32a for introducing each crucible R and the other end open upward of the crucible installation part 33 as an outlet port 32b for discharging the crucible R. The guide passage 32 according to the present embodiment is formed by a guide tube 5 of a generally cylindrical shape almost vertically and the introduction port 32a of the guide passage 32 communicates with the discharge port 312 of the crucible accommodation part 31.

Moreover, the guide passage 32 drops the crucible R introduced from the crucible accommodation part 31 in a state in which upper and lower sides of the crucible R remain set in a right direction. The guide passage 32 has an inside diameter at which the crucible R is not installed upside down when the crucible R falls or, for example, an inside diameter smaller than a length of a longest diagonal of the crucible R.

One or a plurality of (three in FIG. 18) through-holes 5A of, for example, a slit shape is provided in a sidewall of the guide tube 5 for discharging foreign matters (such as fragments of the crucible R) other than the crucible R introduced from the feed port 312 to outside of the guide tube 5 without arrival at the outlet (outlet port 32b). Specifically, the through-holes 5A are provided downward of a sidewall of a bent portion 51 of the guide tube 5 which portion is provided almost perpendicularly to the inclined surface 311. The fragments are thereby discharged to the outside of the guide tube 5 through the through-holes 5A by an empty weight of each fragment. Furthermore, these through-holes 5A make it possible to confirm whether or not the crucibles R clog in the guide passage 32.

Moreover, a throttle structure 321 that fulfils a drop velocity reduction function of reducing a drop velocity of the crucible R and a displacement prevention function of preventing displacement of an installation position of the crucible R on the crucible installation part 33 is provided on the guide passage 32. This throttle structure 321 is provided on the outlet port 32b-side of the guide passage 32. More specifically, the throttle structure 321 is provided at such a position that the throttle structure 321 can fulfill the drop velocity reduction function and the displacement prevention function. In the present embodiment, the throttle structure 321 is provided to be continuous to the outlet port 32b.

The throttle structure 321 is intended to reduce a cross-sectional area of the guide passage 32 and to narrow a passing region of the crucible R. Specifically, the throttle structure 321 includes a tapered portion 3211 provided near the outlet port 32b of the guide passage 32 and gradually tapered toward the outlet port 32b, and a small-diameter portion 3212 of a uniform cross section provided continuously to an outlet port-side end portion of the tapered portion 3211 and having a diameter identical to a smallest diameter of the tapered portion 3211.

The smallest diameter of this tapered portion 3211 (an inside diameter of the small-diameter portion 3212) is a diameter that is slightly larger than an outside diameter of the crucible R and that makes it possible for the crucible R to pass through by the empty weight of the crucible R. Further, the small-diameter portion 3212 is formed to range from the outlet port-side end portion of the tapered portion 3211 to the outlet port 32b of the guide passage 32. The crucible R passing through the small-diameter portion 3212 thereby drops while keeping an attitude of being installed on the crucible installation part 3 (that is, an attitude in which a central axis of the crucible R is almost in the vertical direction).

This throttle structure 321 causes the crucible R to contact with the tapered portion 3211 halfway along dropping and to contact with an inner circumferential surface of the small-diameter portion 3212. A contact resistance generated during the contact of the crucible R with the tapered portion 3211 and the inner circumferential surface of the small-diameter portion 3212 can reduce the drop velocity of the crucible R at the outlet port 32b of the guide passage 32. It is, therefore, possible to prevent the crucible R from being damaged or broken when the crucible R grounds on the crucible installation part 33. Further, since the small-diameter portion 3212 has the inside diameter slightly larger than the outside diameter of the crucible R, it is possible to prevent a grounding position of the crucible R on the crucible installation part 33 from differing, prevent displacement of the installation position of the crucible R on the crucible installation part 33 and to install the crucible R with high accuracy.

As shown in FIGS. 16 and 17, the crucible installation part 33 is provided in a tip end portion of a driving shaft 341 of an elevating mechanism 34 configured to include an air cylinder or the like and provided on a base 101. The crucible installation part 33 vertically moves between a receiving position Q1 at which the crucible installation part 33 is connected to the guide passage 32 and receives the dropped crucible R and a crucible transport position Q2 that is a distant position away from the receiving position Q1 vertically downward.

Specifically, as shown in FIG. 17, the crucible installation part 33 includes a concave portion 331x in which one crucible R can be accommodated, a crucible receiver main body 331 receiving the crucible R and a mount protrusion 332 provided in the concave portion 331x of the crucible receiver main body 331.

The crucible receiver main body 331 has a generally bottomed cylindrical shape and an interior made of visually recognizable transparent resin. An inside diameter of the concave portion 331x is larger than an outside diameter of the crucible R.

The mount protrusion 332 is generally cylindrical and a diameter of the mount protrusion 332 is set slightly smaller than an opening diameter of the crucible R. The mount protrusion 332 is provided coaxially in the concave portion 331x of the crucible receiver main body 331. If the crucible R is installed with upper and lower sides of the crucible R set in a right direction, the crucible R is mounted on an almost horizontal upper surface 332a of the mount protrusion 332. On the other hand, if the crucible R is installed upside down, the mount protrusion 33 is contained in the crucible R. By so configuring, a height position of the crucible R on the crucible installation part 33 differs between an instance of installing the crucible R with the upper and lower sides set in the right direction and the instance of installing the crucible R upside down.

A length of the mount protrusion 332 is set larger than a depth of any of various types of crucibles R to be used, thus providing a structure available irrespectively of the size of the crucible R. That is, the length of the mount protrusion 332 is set to a length at which an opening of the crucible R does not contact with a bottom of the concave portion if the crucible R is installed upside down. In other words, the length of the mount protrusion 332 is set to form a space between the bottom of the concave portion and an end surface of the opening of the crucible R. By so setting, even if such foreign matters as fragments of the crucible R are accumulated in the concave portion 331x, the crucible receiver main body 331 can accommodate the crucible R upside down.

As shown in FIGS. 16 and 17, this crucible feeder mechanism 3 also includes a crucible detection sensor 41 and the crucible detection sensor 41 and the crucible installation part 33 constitute an inversion detection mechanism 4.

The crucible detection sensor 41 is a sensor using light and detecting the crucible R only if the crucible R is installed on the mount protrusion 332 with the upper and lower sides thereof set in the right direction. Specifically, a photoelectric sensor is used as the crucible detection sensor 41. The photoelectric sensor 41 is configured so that an orbit of a light L1 emitted from a light emitting part of the photoelectric sensor 41 and reaching a light receiving part thereof is reflected by an outer circumferential surface of the crucible R installed on the crucible installation part 33 with the upper and lower sides thereof set in the right direction and reaches the light receiving part.

By so configuring the photoelectric sensor 41, if the crucible R is installed with the upper and lower sides thereof set in the right direction, the light L1 emitted from the light emitting part is reflected by a side surface of the crucible R and received by the light receiving part of the photoelectric sensor 41. On the other hand, if the crucible R is installed upside down, the light L1 emitted from the light emitting part is not reflected by the outer circumferential surface of the crucible R and not received by the light receiving part. In this way, the light receiving part does not receive the light L1 if the crucible R is not installed on the crucible installation part 33 or the crucible R is installed but installed upside down. Therefore, it is possible to detect whether or not the crucible R is present and whether or not the crucible R is inverted. Moreover, a detection signal of the light receiving part is output to notification means, not shown, so as to notify an operator of detection by an alarm or the like. The crucible detection sensor 41 is not limited to the reflection sensor stated above but may be a transmission sensor, a sensor using ultrasonic wave or the like.

<<Positioning Mechanism 6>>

As shown in FIG. 17, the crucible feeder mechanism 3 according to the present embodiment further includes a positioning mechanism 6 positioning the outlet port 32b of the guide passage 32 and the crucible installation part 33 with respect to each other.

This positioning mechanism 6 is configured to include a convex portion 61 provided on one of the crucible installation part 33 and the guide tube 5 and a concave portion 62 provided on the other part or tube and fitted into the convex portion 61. In a state in which the concave portion 62 is fitted into the convex portion 61, a central axis of the throttle structure 321 provided near the outlet port 32b of the guide passage 32 is made to coincide with a central axis of the crucible receiver main body 331 (mount protrusion 332).

Specifically, the convex portion 61 according to the present embodiment is tapered to have a smaller diameter toward a tip end thereof and constituted by a tapered portion 331t formed on an upper end portion of a side circumferential wall of the crucible receiver main body 331. Further, the concave portion 62 is tapered to have a larger diameter toward a tip end thereof and constituted by a tapered portion 5t formed around the outlet port 32b of the guide tube 5.

As the crucible installation part 33 moves from the crucible transport position Q2 to the receiving position Q1, the tapered portion 331t of the crucible receiver main body 331 is fitted into and positioned with respect to the tapered portion 5t of the guide tube 5. In a state in which the crucible installation part 33 reaches the receiving position Q1, the central axis of the throttle structure 321 or, to be specific, a central axis of the small-diameter portion 3212 coincides with that of the crucible receiver main body 331 (mount protrusion 332). It is to be noted that an actuator having low positioning accuracy such as an air cylinder can be used as the elevating mechanism 34 by interposing an elastic body such as a spring between the crucible receiver main body 331 and the driving shaft 341.

Moreover, since the crucible R drops almost coaxially with the small-diameter portion 3212 of the throttle structure 321, then the central axis of the crucible R almost coincides with that of the crucible receiver main body 331 (mount protrusion 332), and positioning accuracy for installing the crucible R on the crucible installation part 33 can be made quite high.

Advantages of Third Embodiment

According to the elementary analysis device 100 according to the third embodiment configured as stated above, the cross-sectional area of the guide passage 32 is decreased and the passing region is narrowed, whereby the crucible R contacts with the throttle structure 321 and the drop velocity of the crucible R can be reduced despite the simple configuration that the throttle structure 321 is provided on the outlet port 32b-side of the guide passage 32. Further, since the passing region of the crucible R is narrowed, it is possible to prevent displacement of the grounding position of the crucible R and install the crucible R on the crucible installation part 33 with high accuracy.

Moreover, since the tapered portion 3211 and the small-diameter portion 3212 constitute the throttle structure 321, the throttle structure 321 can be made simple in configuration and it is possible to ensure smoothly dropping the crucible R. In addition, it is possible to make it difficult to re-accelerate the drop velocity of the crucible R reduced by the tapered portion 3211 and the grounding position of the crucible R can be set with higher accuracy.

Modifications of Third Embodiment

The present invention is not limited to the third embodiment. Modifications of the third embodiment will be described. Constituent elements corresponding to those according to the third embodiment will be denoted by the same reference symbols as those used in the second embodiment.

Figure 19:
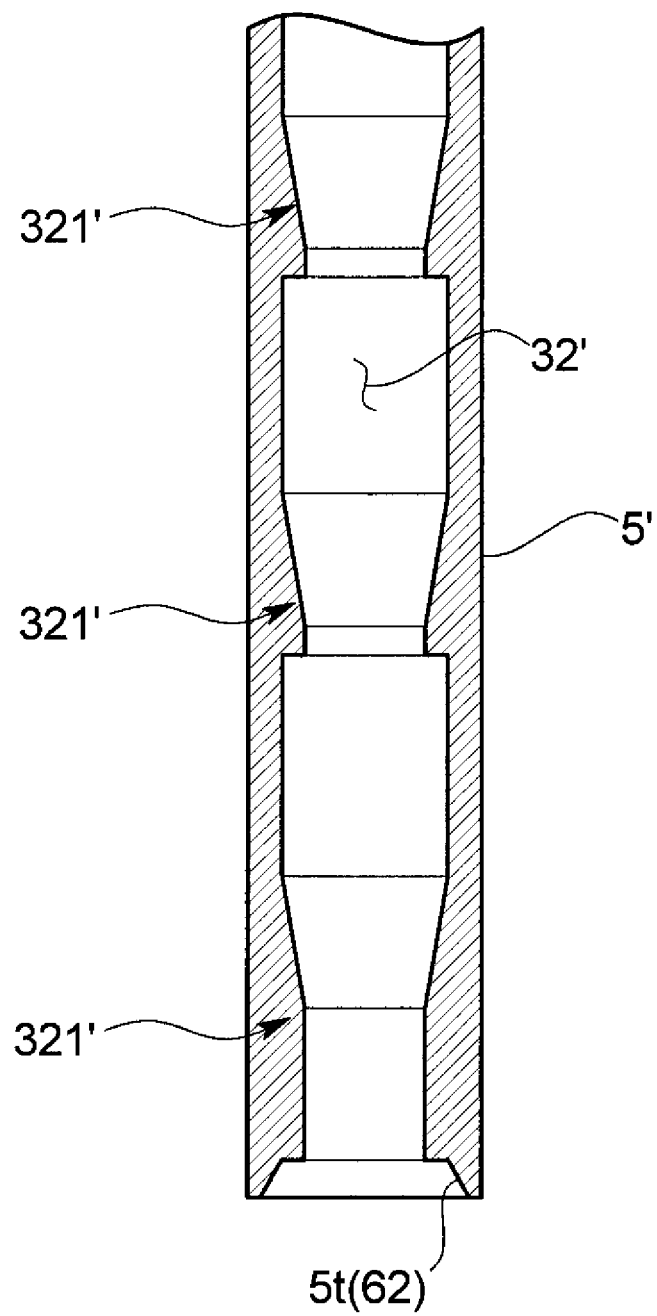
FIG. 19 is a cross-sectional view showing a throttle structure according to the modification of the third embodiment.

For example, only one throttle structure 321 according to the third embodiment is provided on the outlet port 32b-side of the guide passage 32. Alternatively, as shown in FIG. 19, a plurality of (three in FIG. 19) throttle structures 321' may be provided on a guide passage 32'. In this case, it is unnecessary for each of the throttle structures 321' other than that provided to be closest to the outlet port to include a small-diameter portion and each of the throttle structures 321' other than that provided to be closest to the outlet port may include only a tapered portion. If a plurality of throttle structures 321' is provided, a drop velocity of each crucible R is reduced whenever passing through each throttle structure 321'. It is, therefore, possible to prevent the crucible R from being damaged or broken at the time of grounding on a crucible installation part 33. Besides, when the crucible is dropped in the guide passage 32', it is possible to prevent the crucible R from striking against an inner circumferential surface of a guide tube 5' constituting the guide passage 32' and from being damaged and broken.

Figure 20:
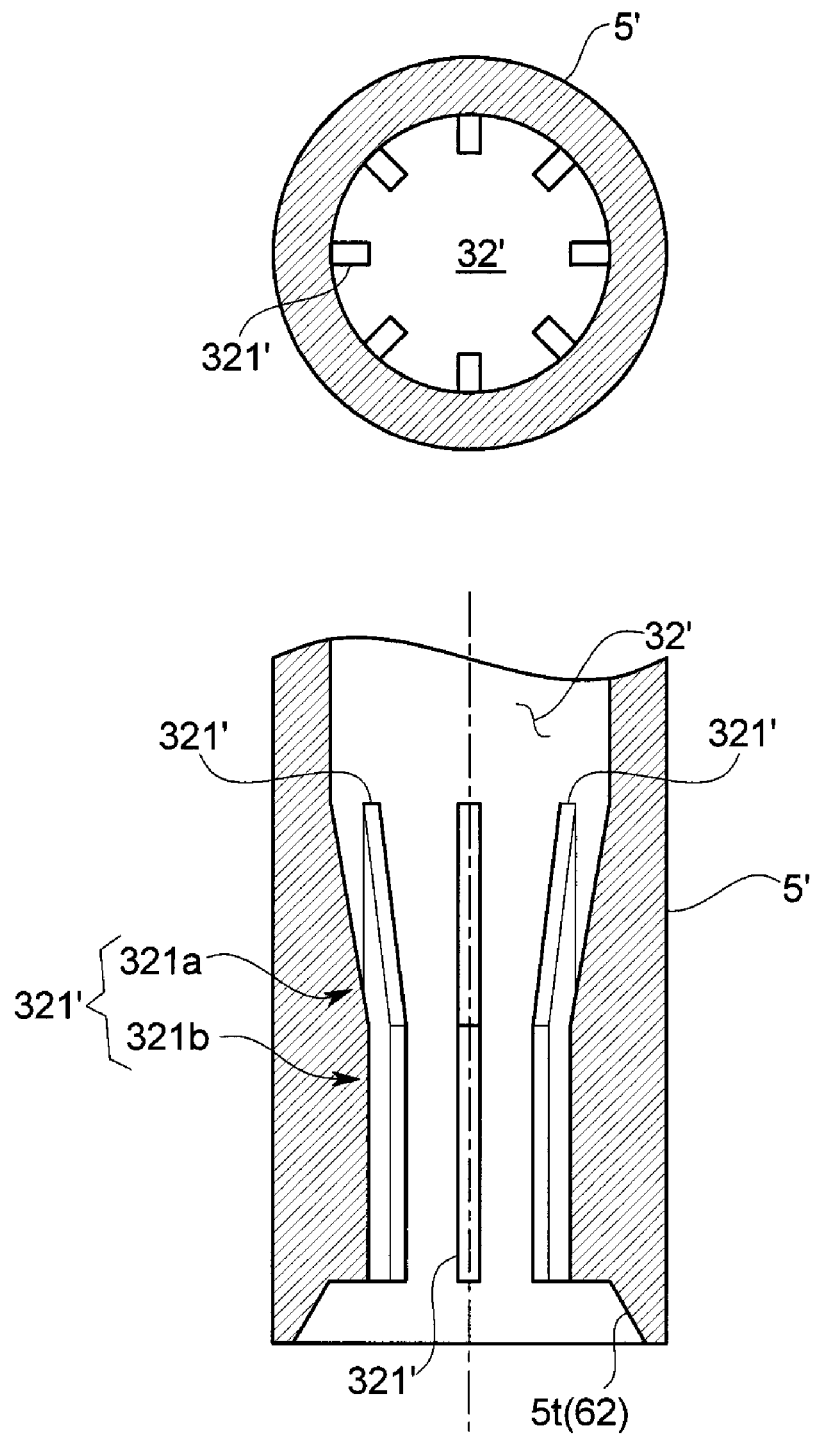
FIG. 20 is a longitudinal sectional view and a cross-sectional view showing a modification of the throttle structure shown in FIG. 19.

Furthermore, as shown in FIG. 20, each of the throttle structures 321' may include a plurality of protrusions extending in a passage direction and provided on the inner circumferential surface of the guide tube 5', for example, radially. In this case, each of the protrusions is configured to include an inclined portion 321a that is generally doglegged and a height of which is gradually larger toward the outlet port, and a constant-height portion 321*b* provided to be continuous to an outlet port-side end portion of the inclined portion 321*a* and having a height almost identical to that of the outlet port-side end portion thereof.

Alternatively, the throttle structure may have an inclined flat surface instead of a tapered surface.

Moreover, the throttle structure according to the third embodiment includes the tapered portion and the small-diameter portion. Alternatively, the throttle structure may include only the tapered portion.

Besides, the crucible installation part in the crucible feeder mechanism according to the third embodiment vertically moves. Alternatively, the outlet of the guide tube (the outlet port of the guide passage) may vertically move.

Figure 21:
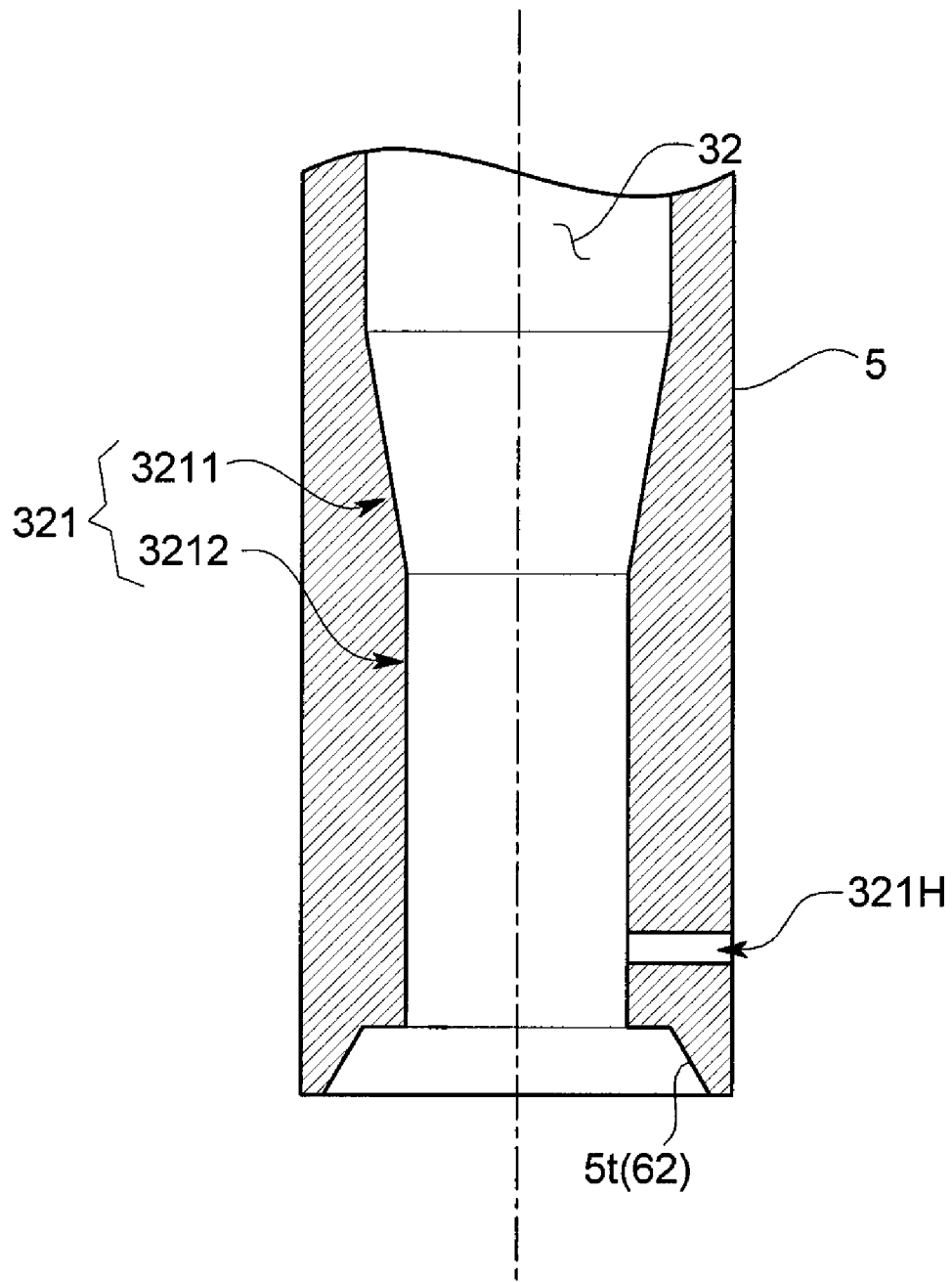
FIG. 21 is a longitudinal sectional view showing a modification of the throttle structure shown in FIG. 19.

Moreover, as shown in FIG. 21, an air hole formed in the small-diameter portion 3212 and communicating an interior and an exterior of the guide passage 32 with each other may be provided. The air hole functions as an air escape when one crucible R passes through the guide passage, thereby making it possible to smoothly dropping the crucible R. Further, if a flow controller such as a needle valve is connected to the air hole and the flow controller controls an amount of the air discharged from or introduced into the air hole, the drop velocity of the crucible R can be made adjustable.

Furthermore, the guide passage 32 according to the third embodiment has a circular cross section. Alternatively, the guide passage 32 may have, for example, a longitudinal cross section.

Furthermore, not only the graphite crucibles but also ceramic crucibles may be used. In this case, the analysis device main body 1 may include a high-frequency heating furnace and may analyze carbon or sulfur present in the sample.

Fourth Embodiment

A fourth embodiment of the present invention will be described. In the fourth embodiment, different reference symbols from those used in the first, second and third embodiments are used.

As disclosed in, for example, the Japanese Patent No. 2949501, an elementary analysis device that has a measurement sample accommodated in a crucible sandwiched between an upper electrode and a lower electrode, heats and dissolves the measurement sample in the crucible by applying voltage, analyzes gas generated by heating and dissolving the sample and thereby analyzes elements of the measurement sample.

In this way, the upper electrode and the lower electrode contact with graphite crucibles and part of the dissolved measurement samples, flux or the like scatters and adheres to the upper and lower electrodes. Due to this, the upper and lower electrodes are stained. Further, if electrode surfaces are stained, stains act as electric resistance. If one crucible is sandwiched between the upper and lower electrodes, then it is difficult to apply current to the crucible and the measurement sample is insufficiently heated, resulting in such problems as deterioration in performance of extracting analysis target gas.

It is, therefore, necessary to clean the upper and lower electrodes after the analysis target gas is extracted.

As a device cleaning the upper and lower electrodes, there is conventionally known an automatic cleaning device disclosed in Japanese Examined Patent Publication No. S58-23886.

The automatic cleaning device disclosed in Japanese Examined Patent Publication No. S58-23886 is configured so that an air cylinder drives a cleaning unit including a rotary brush for cleaning an upper electrode and a rotary brush for cleaning a lower electrode to move straight along a horizontal guide bar and to move forward and backward between an opposing position at which the upper and lower electrodes oppose to each other and a retreat position away from the opposing position. This automatic cleaning device also includes a crucible holder (used crucible removal means). The crucible holder attracts the crucible present on the lower electrode halfway along horizontal movement of the cleaning unit to the opposing position, thereby removing the crucible.

When the cleaning unit reaches the opposing position, the lower electrode is raised, thereby raising the cleaning unit. After the rotary brushes are caused to pressure-contact with the upper and lower electrodes, respectively, the rotary brushes are rotated and the electrodes are cleaned.

However, the conventional automatic cleaning device has the following problems. If the automatic cleaning device is designed to cause the cleaning unit to move straight horizontally, then the guide bar and the air cylinder are made larger in size as a distance between the opposing position and the retreat position is longer, an automatic cleaning mechanism becomes enlarged, and the elementary analysis device becomes enlarged accordingly.

Furthermore, in the conventional elementary analysis device, the crucible is mounted on the lower electrode using tweezers or the like and this mounting operation is quite cumbersome and becomes a factor for obstructing analysis automation. Moreover, there is proposed providing a transport unit separately. However, if the transport unit is provided separately from the cleaning unit, there is no avoiding increasing manufacturing cost of the elementary analysis device and enlarging the elementary analysis device.

The present invention has been made to solve all the problems stated above at a stroke. It is an initial and main object of the present invention to change a conventional method of driving a cleaning unit, to add a transport function to the cleaning unit and to automate supply of a crucible to a lower electrode, disposal of the crucible from the lower electrode and cleaning of the lower electrode or an upper electrode by a simple mechanism, and to make it possible to make an elementary analysis device small in size.

Namely, an elementary analysis device according to the present invention sandwiching a crucible containing a sample between an upper electrode and a lower electrode, heating the crucible by applying voltage to the upper and lower electrodes, and analyzing an element of the sample from gas generated by heating the crucible, including a transport and cleaning unit transporting the crucible from a crucible installation part in which the crucible is installed onto the lower electrode, and cleaning the upper electrode or the lower electrode, wherein the transport and cleaning unit includes a cleaning body cleaning the upper electrode or the lower electrode; an arm part including a grip clutch gripping the crucible installed on the crucible installation part; and a rotation drive mechanism supporting the arm part by a rotary shaft and driving the arm part to rotate and move to and stop at each of an opposing position at which the cleaning body opposes the upper electrode or the lower electrode, a mount position at which the crucible gripped by the grip clutch on the lower electrode, and a retreat position away from the opposing position and the mount position.

In the elementary analysis device configured as stated above, the cleaning body for cleaning the upper electrode or the lower electrode and the arm part including the grip clutch clutching the crucible are rotated and driven to move to each of the opposing position, the mount position and the retreat position. Therefore, transport of the crucible, disposal of the crucible and cleaning of the electrodes can be automated by a simple mechanism and the elementary analysis device can be made small in size.

If the crucible is mounted onto the lower electrode by the transport unit and the crumble is mounted at the same position for every analysis, then same parts of the upper electrode and the lower electrode between which the crucible is sandwiched are worn away, and service lives of the upper electrode and the lower electrode are disadvantageously shortened. To solve this problem and make it possible to lengthen the service lives, it is preferable that the mount position differs whenever the rotation drive mechanism drives the arm part to move to the mount position so that a position of the crucible on the lower electrode differs whenever the crucible is mounted on the lower electrode.

In this way, according to the present invention, a transport mechanism for transporting one crucible onto the lower electrode and a cleaning unit for cleaning the lower electrode are integrated with each other, supply of the crucible to the lower electrode, disposal of the crucible from the lower electrode and cleaning of the lower electrode or the upper electrode are automated by a simple mechanism, the elementary analysis device can be made small in size and manufacturing cost of the elementary analysis device can be reduced.

Figure 22:
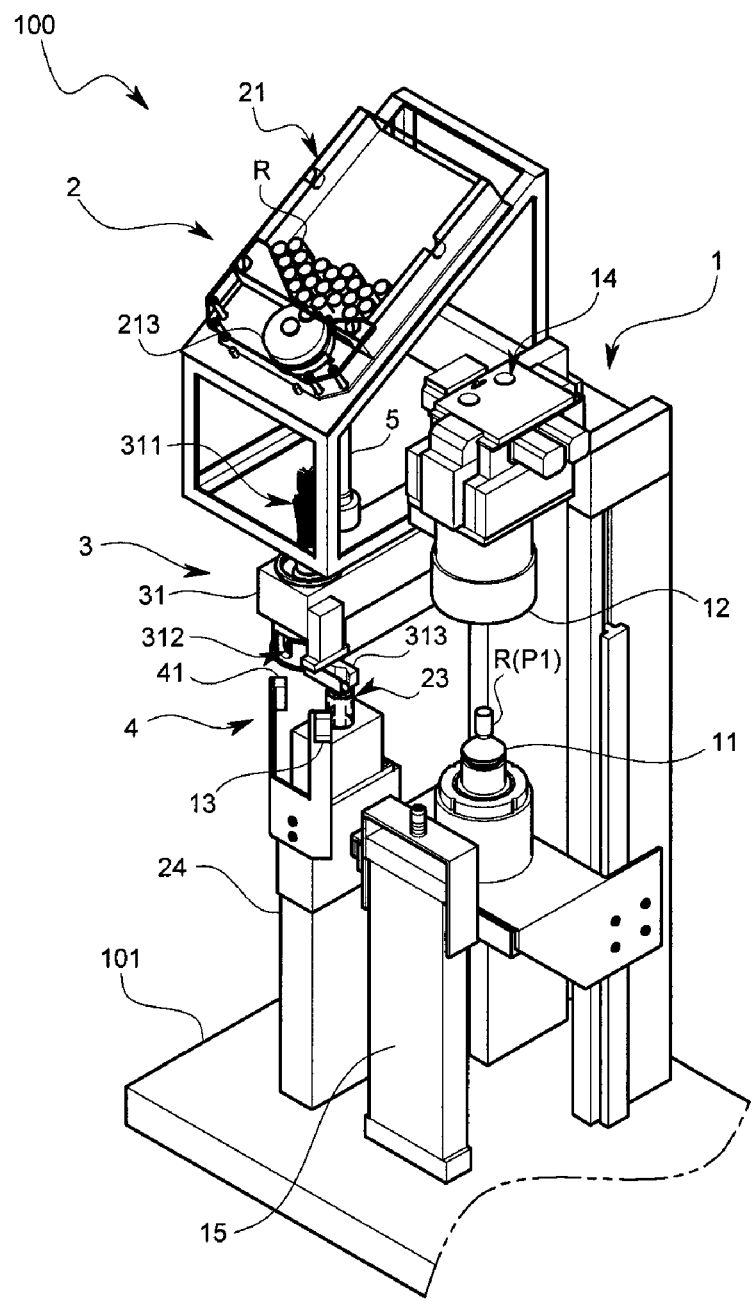
FIG. 22 is a typical configuration diagram of an elementary analysis device according to a fourth embodiment of the present invention.
Figure 23:
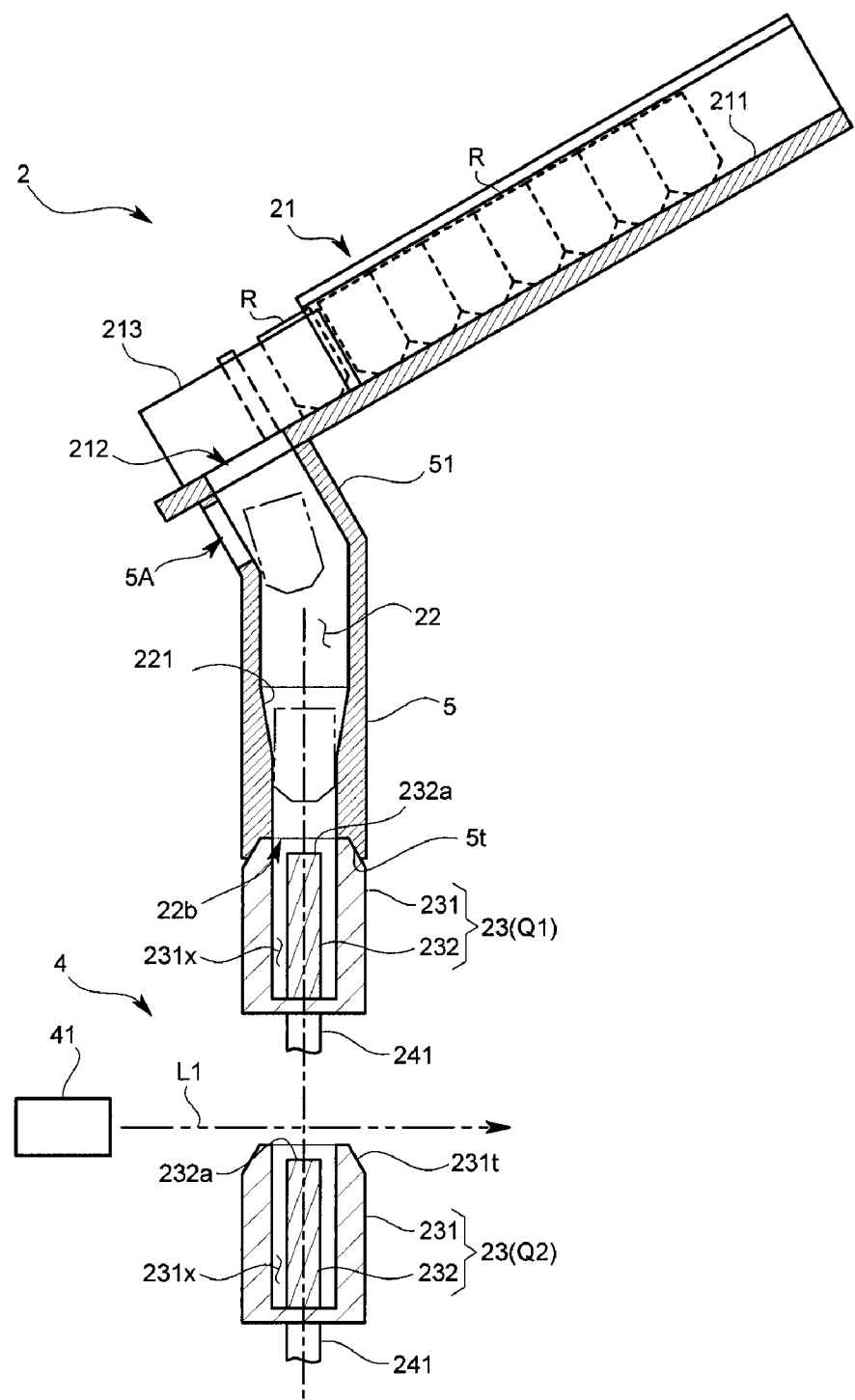
FIG. 23 is a typical configuration diagram of a crucible feeder mechanism according to the fourth embodiment.
Figure 24:
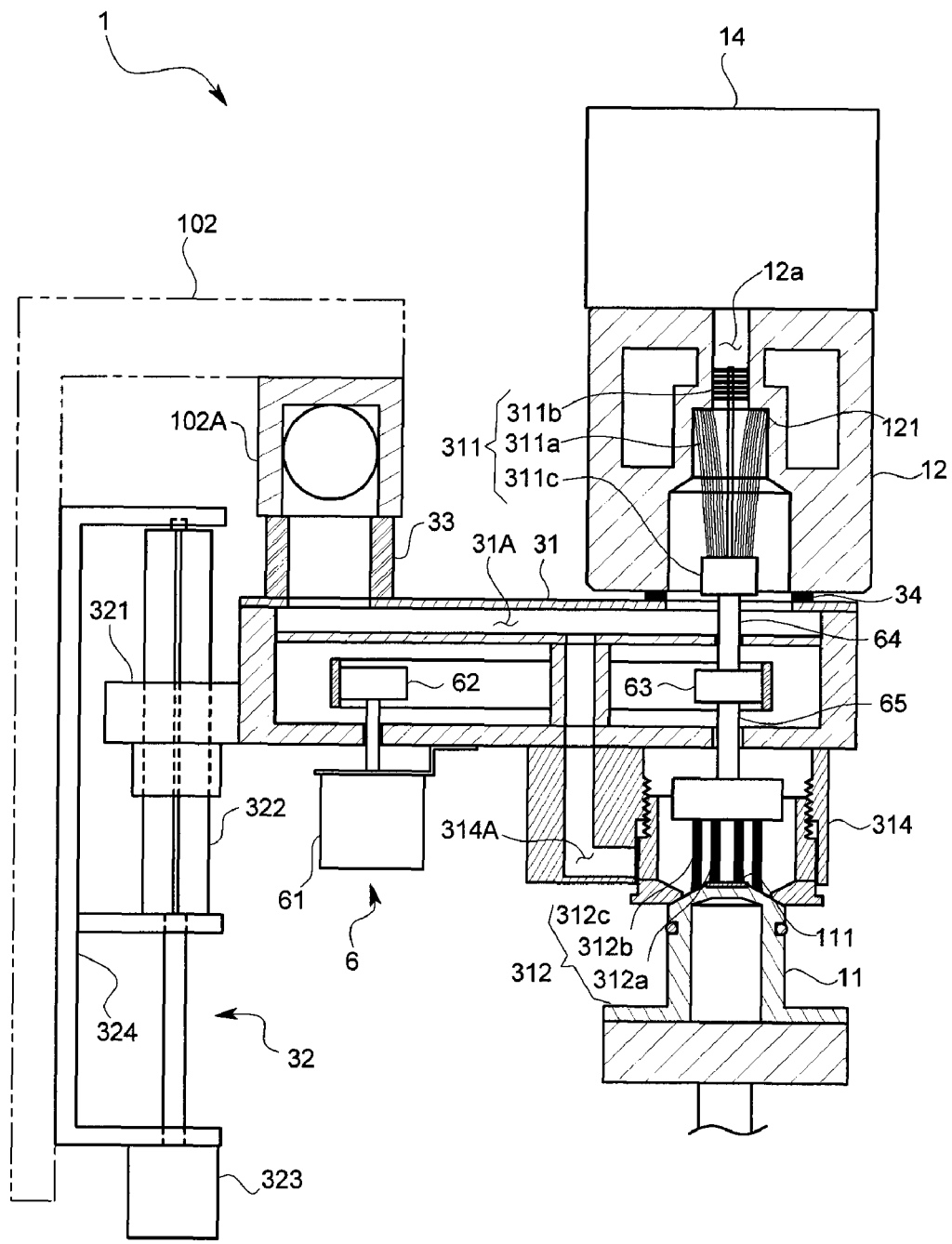
FIG. 24 is a cross-sectional view mainly showing an electrode part and a transport and cleaning unit according to the fourth embodiment.
Figure 25:
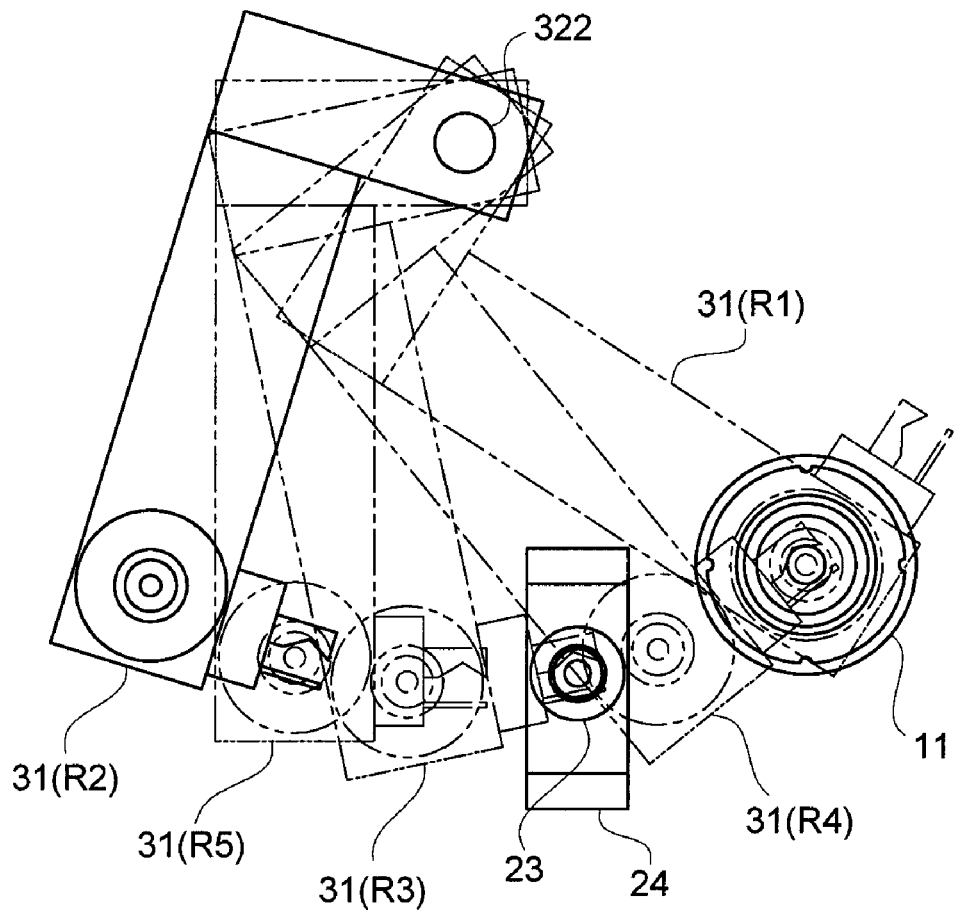
FIG. 25 is a schematic diagram showing stop positions of an arm part according to the fourth embodiment.
Figure 26:
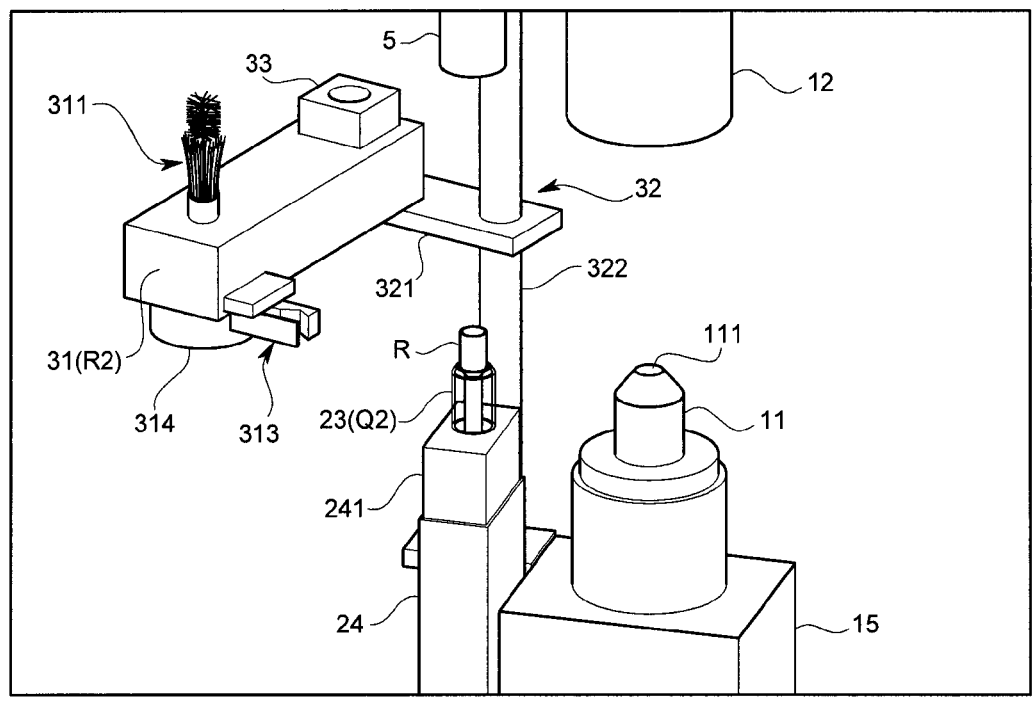
FIG. 26 is a typical view showing a retreat position R2 of the arm part according to the fourth embodiment.
Figure 27:
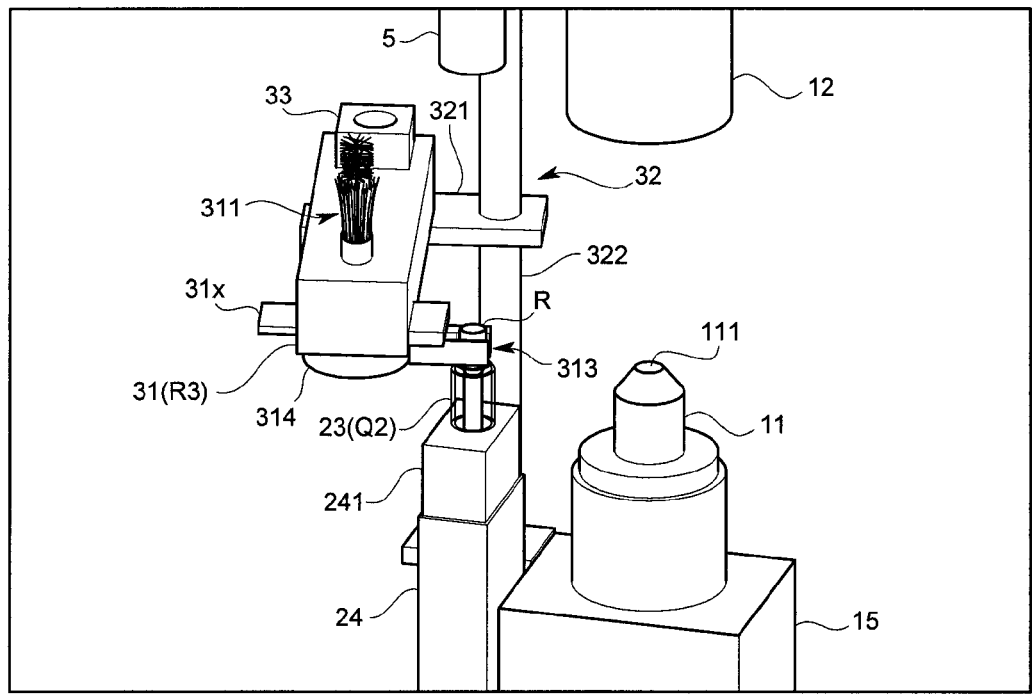
FIG. 27 is a typical view showing a grip position R3 of the arm part according to the fourth embodiment.
Figure 28:
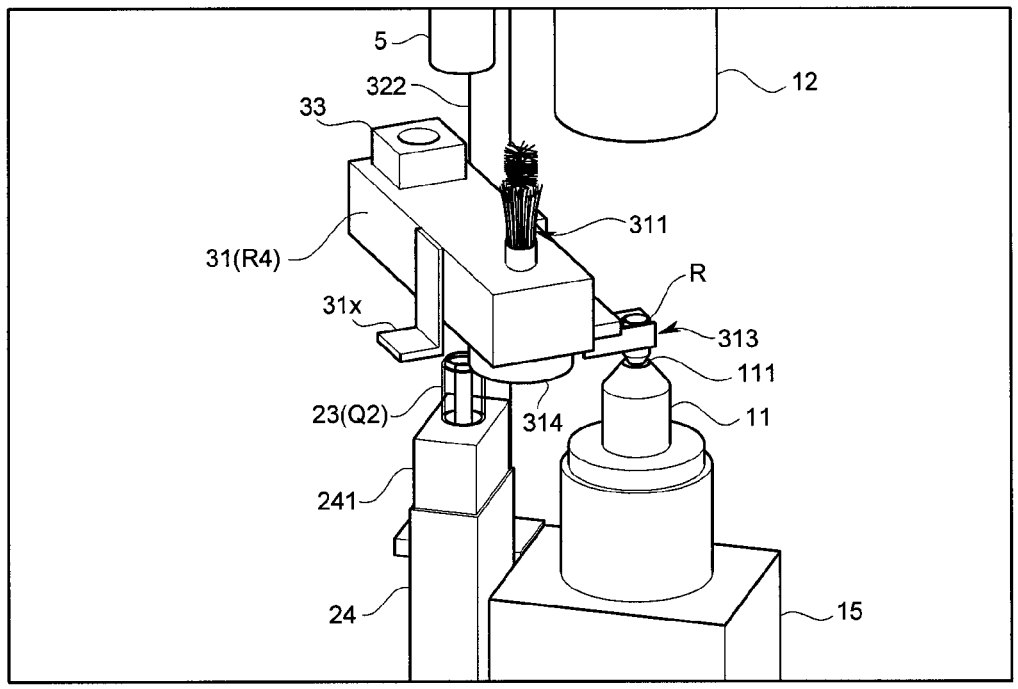
FIG. 28 is a typical view showing a mount position R4 of the arm part according to the fourth embodiment.
Figure 29:
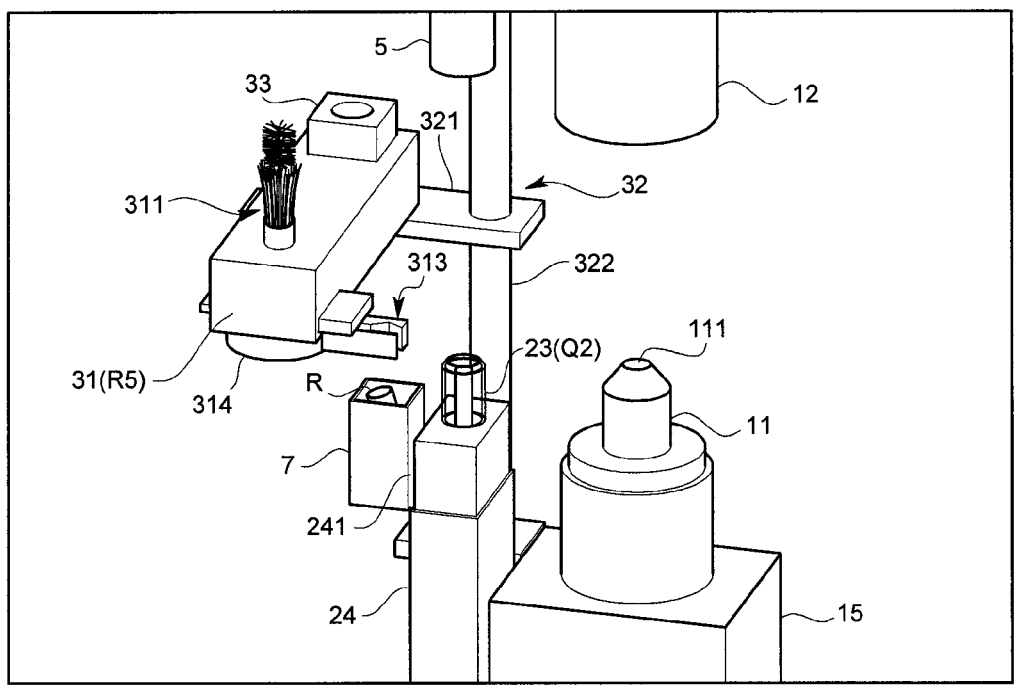
FIG. 29 is a typical view showing a disposal position R5 of the arm part according to the fourth embodiment.
Figure 30:
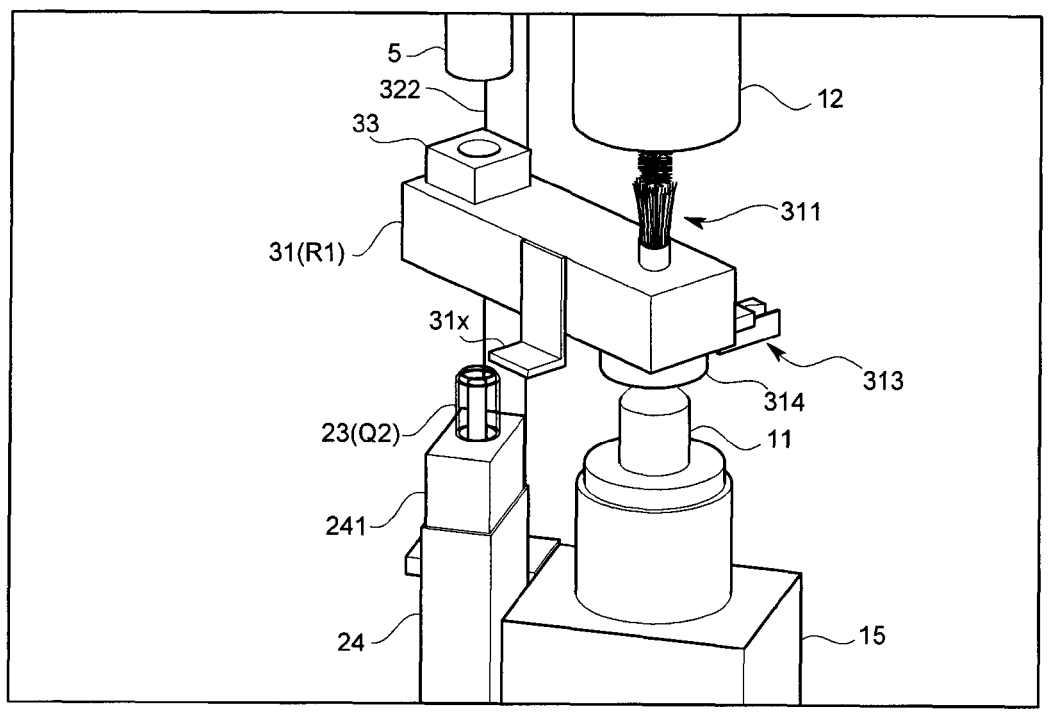
FIG. 30 is a typical view showing an opposing position R1 of the arm part according to the fourth embodiment.

The fourth embodiment of the present invention will be described referring to the drawings. FIG. 22 is a schematic configuration diagram of an elementary analysis device 100 according to the fourth embodiment, and FIG. 23 is a typical cross-sectional view showing a configuration of a crucible feeder mechanism 2. FIG. 24 is a cross-sectional view mainly showing an electrode part and a transport and cleaning unit 3 of the elementary analysis device. FIG. 25 is a schematic diagram showing stop positions of an arm part. FIG. 26 shows a retreat position R2, FIG. 27 shows a grip position R3, FIG. 28 shows a mount position R4, FIG. 29 shows a disposal position R5, FIG. 30 shows an opposing position R1 and FIG. 33 is a schematic diagram showing cleaning stages.

<Device Configuration>

The elementary analysis device 100 according to the fourth embodiment heats and dissolves a metal sample (hereinafter, also simply "sample") accommodated in each of crucibles R and analyzes components of gas generated at the time of heating and dissolving, thereby measuring an element contained in the sample. The elementary analysis device 100 includes an analysis device main body 1, a crucible feeder mechanism 2 feeding a transported crucible R to the device main body 1 and a transport and cleaning unit 3 transporting the crucible R fed by the crucible feeder mechanism 2 to the analysis device main body 1 and cleaning the analysis device main body 1. The analysis device main body 1, the crucible feeder mechanism 2 and the transport and cleaning unit 3 will be described, respectively.

<<Analysis Device Main Body 1>>

The analysis device main body 1 will first be described. As shown in FIG. 22, an upper electrode 12 and a lower electrode 11 are provided on a front surface of this analysis device main body 1 to be vertically distanced from each other and the analysis device main body 1 is configured to be able to mount one of the crucibles R in which the sample is accommodated on the lower electrode 11. A position of the crucible R mounted on the lower electrode 11 shown in FIG. 22 is a heating position P1. In FIG. 22, reference symbol 13 denotes a detection sensor (such as a photoelectric sensor) detecting whether or not a crucible R is present on the lower electrode 11. Each crucible R is made of graphite, and has an open upper portion of a cylindrical shape and a tapered lower end portion. The crucible R may have an annular concave groove on an outer circumference of the lower end portion instead of having the tapered lower end portion.

During an analysis, the lower electrode 11 slides upward with respect to the crucible R located at the heating position P1 to sandwich the crucible R between the lower electrode 11 and the upper electrode 12. In this state, when a sample is input into the crucible R from a sample input port 12A provided above the upper electrode 12, then current is applied between the electrodes 11 and 12, heat is generated from the crucible R, and the sample within the crucible R is heated and dissolved. Gas generated from the heated sample is supplied to an analysis part, not shown, components of the gas are measured and elements originally contained in the sample are analyzed as a result of measurement of the gas components.

To measure an amount of oxygen contained in the sample, for example, CO (carbon monoxide) that is a reaction product is generated by heating the sample, CO is measured using, for example, a non-dispersive infrared analyzer constituting the analysis part and the amount of oxygen present in the sample is measured and calculated based on a measured CO value. Furthermore, such components as hydrogen and nitrogen can be measured by setting the reaction product and the analysis part according to the reaction product. After the analysis, the transport and cleaning unit 2 disposes of the used crucible R as well as the sample.

<<Crucible Feeder Mechanism 2>>

The crucible feeder mechanism 2 automatically feeds the crucible R transported by the transport and cleaning unit 3 to be described later. Particularly shown in FIG. 23, the crucible feeder mechanism 2 includes a crucible accommodation part 21 in which a plurality of crucibles R can be accommodated, a guide passage 32 dropping each crucible R from the crucible accommodation part 21 by an empty weight of the crucible R and a crucible installation part 23 provided at an outlet port 22b of the guide passage 22 and receiving the dropped crucible R.

The crucible accommodation part 21 includes an inclined surface 211 on which a plurality of crucibles R is mounted in parallel, a discharge port 212 provided downward of the inclined surface 211 and a crucible discharge mechanism 213 holding one of the crucibles R sliding downward of the inclined surface 211 and moving the crucible R to the discharge port 212. The discharge mechanism 213 is configured to include, for example, a rotating body (see FIG. 22) having a concave portion formed on a side surface, accommodating therein the crucible R and rotating uniaxially about a shaft and a driving part (not shown) driving the rotating body to rotate, and to move the crucible R to the discharge port 212 by rotating the crucible R accommodated in the concave portion. The crucible discharge mechanism 213 drops and discharges the crucible R moved to an upper portion of the discharge port 212 from the discharge port 212 by the empty weight of the crucible R. With this configuration, since the crucibles R are accommodated in parallel, the crucibles R can be accommodated as many as possible. Furthermore, since the crucibles R are discharged using the empty weight of each crucible R, the discharge mechanism 213 can be made simple in structure.

The guide passage 22 drops each crucible R almost vertically and guides the crucible R to the crucible installation part 23. As shown in FIG. 23, the guide passage 22 communicates with a feed port 214 of the crucible accommodation part 21 and is formed almost vertically.

Moreover, the guide passage 22 drops the crucible R introduced from the crucible accommodation part 21 in a state in which upper and lower sides of the crucible R remain set in a right direction. The guide passage 32 has an inside diameter at which the crucible R is not installed upside down when the crucible R falls or, for example, an inside diameter smaller than a length of a longest diagonal of the crucible R.

One or a plurality of through-holes 5A of, for example, a slit shape is provided in a sidewall of a guide tube 5 for discharging foreign matters (such as fragments of the crucible R) other than the crucible R introduced from the feed port 214 to outside of the guide tube 5 without arrival at the outlet (outlet port 22b). Specifically, the through-hole 5A is provided downward of a sidewall of a bent portion 51 of the guide tube 5 which portion is provided almost perpendicularly to the inclined surface 211. The fragments are thereby discharged to the outside of the guide tube 5 through the through-hole 5A by an empty weight of each fragment. Furthermore, these through-hole 5A makes it possible to confirm whether or not the crucibles R clog in the guide passage 22.

Moreover, a tapered portion 221 is formed near the outlet of the guide passage 22 for reducing a drop velocity of the crucible R. A smallest diameter of this tapered portion 221 is slightly larger than an outside diameter of the crucible R so that the crucible R can pass through the tapered portion 221. Further, a downstream side of the tapered portion 221 of the guide passage 22 has a diameter identical to the smallest diameter of the tapered portion 221. By so forming the tapered portion 221, the drop velocity of the crucible R near the outlet port 22a of the guide passage 22 can be reduced and the crucible R can be prevented from being damaged when the crucible R grounds on the crucible installation part 23. Besides, the tapered portion 221 can prevent displacement of an installation position of the crucible R on the crucible installation part 23 and the crucible R can be installed with high accuracy.

As shown in FIGS. 22 and 23, the crucible installation part 23 is provided in a tip end portion of a driving shaft 241 of an installation part elevating mechanism 24 configured to include an air cylinder or the like and provided on a base 101. The crucible installation part 23 vertically moves between a receiving position Q1 at which the crucible installation part 23 is connected to the guide passage 22 and receives the dropped crucible R and a crucible transport position Q2 that is a distant position away from the receiving position Q1 vertically downward.

Specifically, as shown in FIG. 23, the crucible installation part 23 includes a concave portion 231x in which one crucible R can be accommodated, a crucible receiver main body 231 receiving the crucible R and a mount protrusion 232 provided in the concave portion 231x of the crucible receiver main body 331.

The crucible receiver main body 231 has a generally bottomed cylindrical shape and an interior made of visually recognizable transparent resin. An inside diameter of the concave portion 231x is larger than an outside diameter of the crucible R. Furthermore, a tapered surface 231t is formed on an outer circumferential surface of an upper end of the crucible receiver main body 231. As the crucible installation part 23 moves from the crucible transport position Q2 to the receiving position Q1, the tapered surface 231t is fitted into a tapered surface 5t provided on an outlet-side end surface of the guide tube 5 forming the guide passage 22, thereby fulfilling a positioning function of positioning the crucible receiver main body 231, the mount protrusion 232 and the guide passage 22 with respect to one another (see FIG. 23).

The mount protrusion 232 is generally cylindrical and a diameter of the mount protrusion 232 is set slightly smaller than an opening diameter of the crucible R. The mount protrusion 232 is provided coaxially with the crucible receiver main body 231 in the concave portion 231x of the crucible receiver main body 231. If the crucible R is installed with the upper and lower sides of the crucible R set in the right direction, the crucible R is mounted on an almost horizontal upper surface 232a of the mount protrusion 232. On the other hand, if the crucible R is installed upside down, the mount protrusion 23 is contained in the crucible R. By so constituting, a height position of the crucible R on the crucible installation part 23 differs between the instance of installing the crucible R with the upper and lower sides set in the right direction and the instance of installing the crucible R upside down.

A length of the mount protrusion 232 is set larger than a depth of any of various types of crucibles R to be used, thus providing a structure available irrespectively of the size of the crucible R. That is, the length of the mount protrusion 232 is set to a length at which an opening of the crucible R does not contact with a bottom of the concave portion 231x if the crucible R is installed upside down. In other words, the length of the mount protrusion 232 is set to form a space between the bottom of the concave portion 231x and an end surface of the opening of the crucible R. By so setting, even if such foreign matters as fragments of the crucible R are accumulated in the concave portion 231x, the crucible receiver main body 231 can accommodate the crucible R upside down.

As shown in FIGS. 22 and 23, this crucible feeder mechanism 2 also includes a crucible detection sensor 41 and the crucible detection sensor 41 and the crucible installation part 23 constitute an inversion detection mechanism 4.

The crucible detection sensor 41 is a sensor using light and detecting the crucible R only if the crucible R is installed on the mount protrusion 332 with the upper and lower sides thereof set in the right direction. Specifically, a photoelectric sensor is used as the crucible detection sensor 41. The photoelectric sensor 41 is configured so that an orbit of a light L1 emitted from a light emitting part of the photoelectric sensor 41 and reaching a light receiving part thereof is reflected by an outer circumferential surface of the crucible R installed on the crucible installation part 23 with the upper and lower sides thereof set in the right direction and reaches the light receiving part.

By so configuring the photoelectric sensor 41, if the crucible R is installed with the upper and lower sides thereof set in the right direction, the light L1 emitted from the light emitting part is reflected by a side surface of the crucible R and received by the light receiving part of the photoelectric sensor 41. On the other hand, if the crucible R is installed upside down, the light L1 emitted from the light emitting part is not reflected by the outer circumferential surface of the crucible R and not received by the light receiving part. In this way, the light receiving part does not receive the light L1 if the crucible R is not installed on the crucible installation part 23 or the crucible R is installed but installed upside down. Therefore, it is possible to detect whether or not the crucible R is present and whether or not the crucible R is inverted. Moreover, a detection signal of the light receiving part is output to notification means, not shown, so as to notify an operator of detection by an alarm or the like. The crucible detection sensor 41 is not limited to the reflection sensor stated above but may be a transmission sensor, a sensor using ultrasonic wave or the like.

<<Transport and Cleaning Unit 3>>

The transport and cleaning unit 3 transports one crucible R from the crucible installation part 23 on which the crucible R is installed onto the lower electrode 11 or transports the crucible R on the lower electrode 11 to a disposal box 7 and disposes of the crucible R, and cleaning the upper electrode 12 and the lower electrode 11.

Specifically, the transport and cleaning unit 3 includes an arm part 31 that includes a first cleaning body 311, a second cleaning body 312 and grip clutches 313 serving as a grip part, and a rotation drive mechanism 32 supporting this arm part 31 by a rotary shaft 322 and rotating the rotary shaft 322, thereby driving the arm part 31 to rotate about the rotary shaft 322.

A proximal end portion of the arm part 31 is connected to the rotary shaft 322 of the rotation drive mechanism 32 to be described later, holds the first cleaning body 311 on an upper electrode 12-side of a tip end portion of the arm part 31, and holds the second cleaning body 312 on a lower electrode 11-side of the arm part 311. The grip clutches 313 gripping the crucible R are provided on a side surface of the arm part 31 which surface is in a forward direction to the lower electrode 11.

As shown in FIG. 24, the first cleaning body 311 (upper electrode cleaning body) cleans the upper electrode 12 and is a rotary brush according to the present embodiment. Specifically, the first cleaning body 311 is configured to include a first electrode surface brush 311a for cleaning an electrode surface 121 of the upper electrode 12, a pass hole brush 3111b for cleaning a sample pass hole 12a of the upper electrode 12 and a first substrate 311c holding the brushes 311a and 311b.

The first electrode surface brush 311a is made of, for example, stainless brush bristles and the pass hole brush 311b is made of, for example, nylon brush bristles. The pass hole brush 311b is provided to be closer to a tip end side than the first electrode surface brush 311a. The first substrate 311c is fixed to a first driving shaft 64 of a cleaning body rotation mechanism 6 to be described later.

As shown in FIG. 24, the second cleaning body 312 (lower electrode cleaning body) cleans the lower electrode 11 and is a rotary brush similarly to the first cleaning body 311. Specifically, the second cleaning body 312 is configured to include a second electrode surface brush 312a for cleaning an electrode surface 111 of the lower electrode 11, a peripheral portion brush 312b for cleaning a peripheral portion of the electrode surface 111 of the lower electrode 11 and a second substrate 312c holding the brushes 312a and 312b.

The second electrode surface brush 312a is made of, for example, stainless brush bristles and the peripheral portion brush 312b is made of, for example, nylon brush bristles. The peripheral portion brush 312b is provided outside of the second electrode surface brush 312a. The second substrate 312c is fixed to a second driving shaft 65 of the cleaning body rotation mechanism 6 to be described later.

At least one of the grip clutches 313 is, for example, generally doglegged. Each of the grip clutches 313 employs an air-chuck mechanism and is held to be able to be driven to slide on the proximal end portion of the arm part 31. The transport and cleaning unit 3 is configured to be able to sandwich and grip a side circumferential surface of the crucible R between central portions of the grip clutches 313 by driving the clutches 313 to slide to narrow a distance between the clutches 313 in response to an instruction from a controller (not shown) provided separately.

Furthermore, the arm part 31 includes an air intake passage 31A inside (see FIG. 24). This air intake passage 31A communicates a connection port formed in a proximal end-side upper surface of the arm part 31, an upper electrode-side opening formed on a tip end-side upper surface of the arm part 31 and a lower electrode-side opening formed in a tip end-side lower surface of the arm part 31 with one another. The upper electrode-side opening is formed to be concentric with the first driving shaft 64.

Further, a hollow connection body 33 made of an elastic material is provided on the proximal end-side upper surface of the arm part 31 so as to communicate the connection body 33 with the connection port. When the arm part 31 present at an opposing position R1 rises, the connection body 33 is connected to a suction port 102A provided in a frame 102 of the base 101. The suction port 102A is connected to a suction device (not shown) provided outside of the device 1. The installation part elevating mechanism 24 drives the arm part 31 preset at the opposing position R1 to vertically move. At the opposing position R1, the arm part 31 includes a contact piece 31x in contact with a tip end of the driving shaft 241 of the installation part elevating mechanism 24. This contact piece 31X is generally L-shaped and provided on a side surface of the arm part 31. It is to be noted that the installation part elevating mechanism 24 may be configured so that the driving shaft 241 of the installation part elevating mechanism 24 contacts with a bottom of the arm part 31 to raise the arm part 31.

Moreover, the arm part 31 includes a seal member 34 that is in contact with a lower surface of the upper electrode 12 and that is provided on an opening edge of the upper electrode-side opening of the arm part 31. The lower electrode-side opening is formed by a sidewall 314 provided to be built around the second cleaning body 312. This sidewall 314 adjusts a distance between the lower electrode 11 and the second cleaning body 312, that is, a height of the second cleaning body 312 with respect to the electrode surface 111 of the lower electrode 11 when the arm part 31 is sandwiched between the upper electrode 12 and the lower electrode 11.

The arm part 31 further includes the cleaning body rotation mechanism 6 for rotating the first cleaning body 311 and the second cleaning body 312. As shown in FIG. 24, this cleaning body rotation mechanism 6 includes an actuator 61 such as a motor fixed to a proximal end-side lower surface of the arm part 31, a first pulley 62 fixed to a driving shaft of the actuator 61, a second pulley 63 provided on a tip end side of the arm part 31, a transmission belt 63 transmitting rotation drive of the first pulley 62 to the second pulley 63, the first driving shaft 64 provided on an upper surface of the second pulley 63 and connected to the first substrate 311c of the first cleaning body 311 and the second driving shaft 65 connected to the second substrate 312c of the second cleaning body 312. The actuator 61 is controlled by the controller.

As shown in FIG. 24, the rotation drive mechanism 32 supports the arm part 31 to be vertically movable by the rotary shaft 322 and drives the arm part 31 to rotate. The rotation drive mechanism 32 drives the arm part 31 to rotate and move between the opposing position R1 at which the cleaning bodies 311 and 312 oppose the electrodes 11 and 12, respectively and the retreat position R2 away from the opposing position R1. Furthermore, the rotation drive mechanism 32 can stop the arm part 31 at a plurality of rotation positions between the opposing position R1 and the retreat position R2.

Specifically, the rotation drive mechanism 32 is configured to include a fixing portion 321 to which the arm part 31 is fixed, the rotary shaft 322 inserted into a through-hole formed in the fixing portion 321 so as not to be rotatable relatively to the arm part 31 and so as to be slidable axially, and an actuator 323 connected to a lower end portion of the rotary shaft 322 and rotating the rotary shaft 322. These constituent elements of the rotation drive mechanism 32 are fixed to the device main body 11 by a bracket 324. The actuator 323 is a stepping motor and controlled by a drive pulse from the controller (not shown).

If the rotation drive mechanism 32 configured as stated above is used to cause the actuator 323 to rotate the rotary shaft 322, the arm part 31 that is non-rotatable relatively to the rotary shaft 322 also rotates. The arm part 31 thereby rotates and moves between the opposing position R1 and the retreat position R2 around the rotary shaft 322 as a rotation center.

Further, the rotary shaft 322 and the fixing part 321 are axially slidable. As the installation part elevating mechanism 24 raises the arm part 31, the arm part 31 slides on the rotary shaft 322 and rises.

Specifically, as shown in FIG. 25, the rotation drive mechanism 32 can stop the arm part 31 at the opposing position R1 at which the cleaning bodies 311 and 312 oppose the electrodes 11 and 12, respectively, the grip position R3 at which the grip clutches 313 grip the crucible R on the crucible installation part 23, the mount position R4 at which the crucible R gripped by the grip clutches 313 on the lower electrode 11, the disposal position R5 at which the crucible R gripped by the grip clutches 313 is disposed of into the disposal box 7 and the retreat position R2 away from the respective stop positions R1 and R3 to R5. It is to be noted that the retreat position R2 is located outward of the lower electrode 11 and the crucible installation part 23 with respect to the respective stop positions R1 and R3 to R5.

The transport and cleaning unit 3 according to the present embodiment also includes an arm part elevating mechanism (not shown). This arm part elevating mechanism functions to raise the arm part 31 vertically upward when the grip clutches 313 grip the crucible R present on the crucible installation part 23 in a state in which the arm part 31 is located at the grip position R3. Specifically, the arm part elevating mechanism is configured to include a driving shaft abutting on a lower surface of the arm part 31 and vertically moving and an air cylinder causes the driving shaft to vertically move. This air cylinder is controlled by the controller (not shown). If the arm part elevating mechanism is provided, it is possible to raise and take out the crucible R accommodated in the crucible receiver main body 231 of the crucible installation part 23.

<<Operation Performed By Transport and Cleaning Unit 3>>

Operation performed by the transport and cleaning unit 3 configured as stated above will next be described.

In a crucible feed stage, the crucible installation part 23 of the crucible feeder mechanism 2 rises up to the receiving position Q1, receives the crucible R dropped from the crucible accommodation part 21 to the guide passage 22 and falls to the transport position Q2. At this time, the arm part 31 of the transport and cleaning unit 3 is located at the retreat position R2 (see FIGS. 25 and 26).

In a crucible transport stage, the transport and cleaning unit 3 causes the rotation drive mechanism 32 to drive the arm part 31 located at the retreat position R2 to move and rotate to the grip position R3 (see FIGS. 25 and 27). At this time, the grip clutches 313 provided on the side surface of the arm part 31 grip the crucible R installed on the crucible installation part 23. Thereafter, the arm part elevating mechanism slightly raises the arm part 31. An amount by which the arm part 31 is raised corresponds to a degree to which the crucible R projects from the crucible receiver main body 241 of the crucible installation part 23.

Next, the rotation drive mechanism 32 drives the arm part 32 to rotate and move from the grip position R3 to the mount position R4 (see FIGS. 25 and 28). During this rotation and movement, the arm part elevating mechanism keeps slightly raising the arm part 31.

When the arm part 31 reaches the mount position R4 to mount the crucible R on the lower electrode 11, the arm part elevating mechanism moves the arm part 31 downward. At this time, in a state in which the arm part 31 moves downward and a bottom of the crucible R gripped by the grip clutches 313 surface-contacts with the electrode surface 111 of the lower electrode, the grip clutches 313 release the crucible R.

By doing so, the crucible R is mounted on the lower electrode 11 so as to be pressed onto the lower electrode 11. Due to this, the lower surface of the crucible R contacts with the electrode surface 111 of the lower electrode 11 and the crucible R turns while the crucible R is pressed onto the lower electrode 11. Therefore, even if the grip clutches 313 obliquely grip the crucible R, the crucible R can be stably mounted on the lower electrode R and it is possible to prevent the crucible R from being dropped from upward and bouncing off the lower electrode 11.

After mounting the crucible R on the lower electrode 11, the rotation drive mechanism 32 drives the arm part 31 to rotate and move to the retreat position R2 (see FIG. 25).

Thereafter, in an analysis stage, the lower electrode 11 is raised, the crucible R is sandwiched between the upper electrode 12 and the lower electrode 11, a sample is input and the sample is analyzed. After end of the analysis, the lower electrode 11 is moved downward back to a drop position.

In a crucible disposal stage, the rotation drive mechanism 32 drives the arm part 31 to rotate and move from the retreat position R2 to the mount position R4 (see FIGS. 25 and 28). The grip clutches 313 grip the crucible R present on the lower electrode 11.

The rotation drive mechanism 32 drives the arm part 31 that grips the crucible R on the lower electrode 11 to rotate and move to the disposal position R5. The arm part 31 releases the crucible R at the disposal position R5 and drops the crucible R into the disposal box 7 provided downward of the disposal position R5 (see FIGS. 25 and 29).

Figure 31:
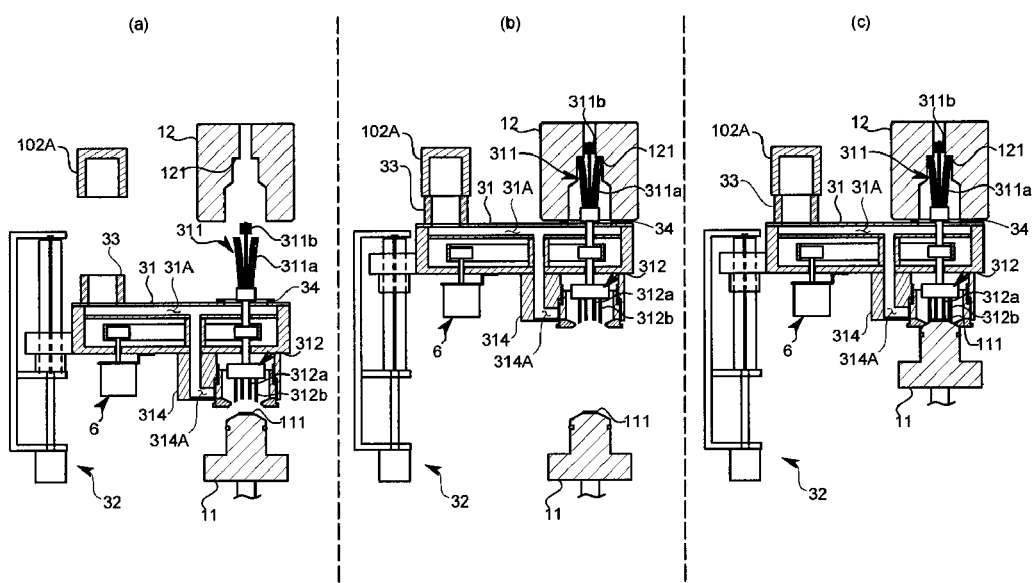
FIGS. 31A to 31C are typical diagrams showing cleaning stages according to the fourth embodiment.

In an electrode cleaning stage, the rotation drive mechanism 32 drives the arm part 31 to rotate and move from the disposal position R5 to the opposing position R1 (see FIGS. 25, 30 and 31A). At this time, the cleaning body rotation mechanism 6 rotates the first cleaning body 311 and the second cleaning body 312.

If the first cleaning body 311 and the second cleaning body 312 rotate, the tip end of the driving shaft 241 of the installation part elevating mechanism 24 contacts with the contact piece 31x to thereby raise the arm part 31. At this time, the seal member 34 provided on the tip end-side upper surface of the arm part 31 contacts with the lower surface of the upper electrode 12 (see FIG. 31B). Further, the brushes 311a and 311b of the first cleaning body 311 remain pressure-contacting with the electrode surface 121 of the upper electrode 12 and the sample pass hole 12a. Furthermore, the connection body 33 is connected to the suction port 102A provided in the frame 102 of the base 101.

At this time, dust generated on the upper electrode 12 is attracted from the upper electrode 12-side opening and discharged from the suction port 102A to the outside via the air intake passage 31A of the arm part 31.

Next, a lower electrode elevating mechanism 15 raises the lower electrode 11. At this time, the peripheral portion of the electrode surface 111 of the lower electrode 11 contacts with the sidewall 314 provided around the second cleaning body 312 (see FIG. 31C). Furthermore, the brushes 312a and 312b of the second cleaning body 312 remain pressure-contacting with the electrode surface 111 of the lower electrode 11 and the peripheral portion of the electrode surface 111 of the lower electrode 11.

At this time, dust generated on the lower electrode 11 is discharged from the suction port 102A to the outside via an air intake path 314A provided in the sidewall 314 and the air intake passage 31A of the arm part 31.

After cleaning, the lower electrode 11 is moved downward, the installation part elevating mechanism 24 drive the arm part 31 to move down to the opposing position R1, and the rotation drive mechanism 32 drives the arm part 31 to rotate and move to the retreat position R2. If a plurality of samples is continuously analyzed, the operation goes to the crucible feed stage again.

In the present embodiment, during the operation performed by the transport and cleaning unit 3 stated above, the mount position R4 is set to differ on the lower electrode 11 whenever the rotation drive mechanism 32 drives the arm part 31 gripping the crucible R using the grip clutches 313 to move to the mount position R4 so as to mount the crucible R on the lower electrode 11. That is, the position at which the crucible R is mounted on the lower electrode 11 is set to differ whenever an analysis is carried out. For example, whenever an analysis is carried out, the position at which the crucible R is mounted on the lower electrode is changed by about 0.5 millimeter (mm).

Specifically, the controller (not shown) sets the drive pulse to be output to the stepping motor serving as the actuator 323 of the rotation drive mechanism 32 to differ whenever the rotation drive mechanism 32 drives the arm part 31 to rotate and move to the mount position R4 so as to mount the crucible R on the lower electrode 11. More specifically, during each analysis, whenever the arm part 31 gripping the crucible R using the grip clutches 313 is moved to the mount position R4, the drive pulse is set at random so that a pulse amount of the drive pulse changes by as much as a few pulses. By doing so, the problem that the same parts of the lower electrode 11 and the upper electrode 12 are worn away can be solved and the service lives of the lower electrode 11 and the upper electrode 12 can be lengthened.

Advantages of Fourth Embodiment

According to the elementary analysis device 100 according to the fourth embodiment configured as stated above, the cleaning bodies 311 and 312 for cleaning the upper electrode 12 and the lower electrode 11, respectively and the arm part that includes the grip clutches 313 gripping the crucible R are driven to rotate and move to the opposing position R1, the grip position R3, the mount position R4, the disposal position R5 or the retreat position R2. It is, therefore, possible to automate transport of the crucible R, disposal of the crucible R and cleaning of the electrodes 11 and 12 by one mechanism simple in configuration and to make the elementary analysis device 100 small in size.

Furthermore, since the stepping motor is used as the actuator 323 of the rotation drive mechanism 32, it is possible to easily make an increase or a decrease of each stop position of the arm part 31, a fine adjustment of each stop position or the like. It is thereby possible to improve maintainability of the elementary analysis device 100 and improve user-friendliness of the elementary analysis device 100 and position accuracy of the mount position R4 and the like of the crucible R.

Modifications of Fourth Embodiment

The present invention is not limited to the fourth embodiment. Modifications of the fourth embodiment will be described. Constituent elements corresponding to those according to the fourth embodiment will be denoted by the same reference symbols as those used in the fourth embodiment.

For example, as the actuator of the rotation drive mechanism, an actuator such as a servo motor or a rotary air cylinder that can stop at a plurality of rotational positions can be used in place of the stepping motor. The rotation drive mechanism may be configured to convert a reciprocating motion of direct-driven type air cylinder into a rotational motion so as to rotate the rotary shaft.

In the fourth embodiment, the arm part located at the opposing position is driven to vertically move by the installation part elevating mechanism. Alternatively, a dedicated elevating mechanism different from the installation part elevating mechanism may be provided to vertically move the arm part located at the opposing position.

Needless to say, a part of or all of the embodiments and modifications may be appropriately combined and the present invention is not limited to the embodiments but can be variously changed or modified without departure from the spirit of the present invention.

What is claimed is:

1. A crucible feeder mechanism used in an elementary analysis device for heating a sample accommodated in a crucible, thereby extracting and analyzing an element contained in the sample as a gas component, comprising:
   an inclined mount surface on which a plurality of crucibles are mounted in parallel; a guide member having an outlet port formed downward of an inclination direction of the mount surface, and guiding one of the crucibles sliding down the mount surface by an empty weight of the crucible toward the outlet port; and
   a crucible moving mechanism provided to interpose between the outlet port of the guide member and a feed port for feeding the crucibles, and moving one of the crucibles sliding down to the outlet port to the feed port,
   wherein the crucible moving mechanism includes
   a crucible moving body provided at the outlet port of the guide member, having an accommodation concave portion for accommodating therein one of the crucibles sliding down the mount surface, formed on a circumferential surface portion of the crucible moving body; and
   a driving part driving the crucible moving body to move between an accommodation position at which the accommodation concave portion receives and accommodates therein one of the crucibles sliding down and a feed position at which the accommodation concave portion communicates with the feed port and the crucible accommodated in the accommodation concave portion is dropped into the feed port, wherein the inclined mount surface, the guide member and the crucible moving body are configured to be operatively detachable from the driving part.

2. The crucible feeder mechanism according to claim 1, wherein the driving part drives the crucible moving body to rotate and causes the circumferential surface portion of the crucible moving body to close the outlet port in a state in which the crucible moving body rotates from the accommodation position.

3. The crucible feeder mechanism according to claim 1, wherein the crucible moving body includes a cantilevered protrusion extending radially outward from a perimeter of the crucible moving body to enable contact with one of the crucibles present near the outlet port of the guide member while the crucible moving body is moving between the accommodation position and the feed position.

4. The crucible feeder mechanism according to claim 1 comprising a safety structure against overturning for preventing the crucibles mounted on the mount surface from overturning, wherein the safety structure against overturning is formed by an opposing surface provided to oppose the mount surface, and a distance between the mount surface and the opposing surface is smaller than a length of a longest diagonal of each of the crucibles.

5. The crucible feeder mechanism according to claim 1 further including an inversion detective mechanism that emits light that will only be reflected to a photodetector sensor if the crucible is positioned vertically, with an upright opening, to monitor alignment of the crucible as released from the feeder mechanism.

6. A crucible feeder mechanism used in an elementary analysis device for heating a sample accommodated in a crucible, thereby extracting and analyzing an element contained in the sample as a gas component, comprising:

an inclined mount surface on which a plurality of crucibles are mounted;

a guide member having an outlet port formed downward of an inclination direction of the mount surface with adjacent inclined surfaces for directing the crucibles towards the outlet port, the inclined surfaces have notch grooves at a position above the inclined mount surface and below a height of the crucibles;

a crucible moving mechanism provided to interpose between the outlet port in the guide member and a feed port for feeding the crucibles and moving one of the crucibles from the outlet port to the feed port, wherein the crucible moving mechanism includes a rotable moving body provided at the outlet port of the guide member having an accommodating concave portion at a perimeter for accommodating therein one of the crucibles and a radially outward protrusion of a configuration to contact and prevent clogging of the plurality of crucibles adjacent the outlet port and to extend through the notch grooves in the guide member as the crucible moving body rotates; and a driving part driving the crucible moving body to move between an accommodation position at which the accommodation concave portion receives and accommodates therein one of the crucibles sliding down and a feed position at which the accommodation concave portion communicates with the feed port and the crucible accommodated in the accommodation concave portion is dropped to the feed port.

7. The crucible feeder mechanism according to claim 6 further including an inversion detective mechanism that emits light that will only be reflected to a photodetector sensor if the crucible is positioned vertically, with an upright opening, to monitor alignment of the crucible as released from the feeder mechanism.

8. The crucible feeder mechanism according to claim 6, wherein the inclined mount surface, the guide member and the crucible moving body are configured to be operatively detachable from the driving part.

* * * * *